United States Patent
Nitsch et al.

(10) Patent No.: US 10,131,708 B2
(45) Date of Patent: Nov. 20, 2018

(54) METHODS OF TREATING ALZHEIMER'S DISEASE

(71) Applicant: University of Zürich, Zürich (CH)

(72) Inventors: Roger Nitsch, Zumikon (CH);
Christoph Hock, Erlenbach (CH);
Christoph Esslinger, Zurich (CH);
Marlen Knobloch, Tolochenaz (CH);
Kathrin Tissot, Neuried (DE); Jan Grimm, Duebendorf (CH)

(73) Assignee: University of Zürich, Zürich (CH)

( * ) Notice: Subject to any disclaimer, the term of this patent is extended or adjusted under 35 U.S.C. 154(b) by 0 days.

(21) Appl. No.: 15/791,632

(22) Filed: Oct. 24, 2017

(65) Prior Publication Data

US 2018/0134773 A1    May 17, 2018

Related U.S. Application Data

(62) Division of application No. 15/066,304, filed on Mar. 10, 2016, now Pat. No. 9,828,420, which is a division of application No. 14/322,096, filed on Jul. 2, 2014, now abandoned, which is a division of application No. 12/522,031, filed as application No. PCT/EP2008/000053 on Jan. 7, 2008, now Pat. No. 8,906,367.

(60) Provisional application No. 60/934,291, filed on Jun. 11, 2007, provisional application No. 60/878,831, filed on Jan. 5, 2007.

(30) Foreign Application Priority Data

Jan. 5, 2007    (EP) .................................... 07000211
Oct. 17, 2007   (EP) .................................... 07020341

(51) Int. Cl.
| | | |
|---|---|---|
| C07K 16/00 | (2006.01) | |
| C07K 16/18 | (2006.01) | |
| A61K 51/10 | (2006.01) | |
| A61K 45/06 | (2006.01) | |
| G01N 33/68 | (2006.01) | |
| A61K 39/00 | (2006.01) | |

(52) U.S. Cl.
CPC ............. *C07K 16/18* (2013.01); *A61K 45/06* (2013.01); *A61K 51/1018* (2013.01); *C07K 16/00* (2013.01); *G01N 33/6854* (2013.01); *G01N 33/6896* (2013.01); *A61K 2039/505* (2013.01); *C07K 2317/21* (2013.01); *C07K 2317/30* (2013.01); *C07K 2317/33* (2013.01); *C07K 2317/34* (2013.01); *C07K 2317/51* (2013.01); *C07K 2317/515* (2013.01); *C07K 2317/55* (2013.01); *C07K 2317/56* (2013.01); *C07K 2317/565* (2013.01); *C07K 2317/73* (2013.01); *C07K 2317/76* (2013.01); *G01N 2333/4709* (2013.01); *G01N 2800/2821* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,876,950 A | 3/1999 | Siadak et al. |
| 6,180,370 B1 | 1/2001 | Queen |
| 6,187,309 B1 | 2/2001 | McMichael et al. |
| 6,294,171 B2 | 9/2001 | McMichael |
| 6,436,401 B1 | 8/2002 | McMichael |
| 6,586,656 B2 | 7/2003 | McLonlogue et al. |
| 6,703,015 B1 | 3/2004 | Solomon et al. |
| 6,710,226 B1 | 3/2004 | Schenk |
| 6,713,058 B2 | 3/2004 | McMichael |
| 6,743,427 B1 | 6/2004 | Schenk |
| 6,750,324 B1 | 6/2004 | Schenk et al. |
| 6,761,888 B1 | 7/2004 | Shecnk |
| 6,787,637 B1 | 9/2004 | Schenk |
| 6,913,745 B1 | 7/2005 | Schenk |
| 7,582,733 B2 | 9/2009 | Basi et al. |
| 7,700,751 B2 | 4/2010 | Basi et al. |
| 7,727,957 B2 | 6/2010 | Schenk et al. |
| 7,763,249 B2 | 7/2010 | Suginura et al. |
| 7,893,214 B2 | 2/2011 | Schenk |

(Continued)

FOREIGN PATENT DOCUMENTS

| | | |
|---|---|---|
| EP | 1 033 996 | 9/2000 |
| EP | 1 172 378 | 1/2002 |

(Continued)

OTHER PUBLICATIONS

"Aducanumab" [online]. ALZFORUM, by Biomedical Research Forum, LLC, first available online Jan. 29, 2014, [Retrieved on Mar. 3, 2016], Retrieved from the Internet: URL <http://www.alzforum.org/therapeutics/aducanumab>, 6 pages.

(Continued)

*Primary Examiner* — Daniel E Kolker
*Assistant Examiner* — Aditi Dutt
(74) *Attorney, Agent, or Firm* — Fish & Richardson P.C.

(57) ABSTRACT

Provided are novel specific binding molecules, particularly human antibodies as well as fragments, derivatives and variants thereof that recognize neoepitopes of disease-associated proteins which derive from native endogenous proteins but are prevalent in the body of a patient in a variant form and/or out of their normal physiological context. In addition, pharmaceutical compositions comprising such binding molecules, antibodies and mimics thereof and methods of screening for novel binding molecules, which may or may not be antibodies as well as targets in the treatment of neurological disorders such as Alzheimer's disease are described.

88 Claims, 10 Drawing Sheets

Specification includes a Sequence Listing.

(56) References Cited

U.S. PATENT DOCUMENTS

| | | |
|---|---|---|
| 7,964,192 B1 | 6/2011 | Schenk |
| 8,003,097 B2 | 8/2011 | Schroeter et al. |
| 8,022,268 B2 | 9/2011 | Grimm et al. |
| 8,034,339 B2 | 10/2011 | Schenk |
| 8,106,164 B2 | 1/2012 | Gellerfors et al. |
| 8,128,928 B2 | 3/2012 | Basi et al. |
| 8,173,127 B2 | 5/2012 | Chain |
| 8,263,558 B2 | 9/2012 | Holzman et al. |
| 8,337,848 B2 | 12/2012 | Kidd et al. |
| 8,378,081 B2 | 2/2013 | Matsubara et al. |
| 8,389,226 B2 | 3/2013 | Ray et al. |
| 8,497,246 B2 | 7/2013 | Pardridge et al. |
| 8,753,610 B2 | 6/2014 | Pardridge et al. |
| 8,906,367 B2 | 12/2014 | Nitsch et al. |
| 9,828,420 B2 | 11/2017 | Nitsch et al. |
| 2002/0086847 A1 | 7/2002 | Chain |
| 2003/0232758 A1 | 12/2003 | St. George-Hyslop et al. |
| 2004/0219146 A1 | 11/2004 | Schenk |
| 2004/0265301 A1 | 12/2004 | Schenk et al. |
| 2005/0009150 A1 | 1/2005 | Basi et al. |
| 2005/0013815 A1 | 1/2005 | Schenk |
| 2005/0048049 A1 | 3/2005 | Schenk |
| 2005/0249725 A1 | 11/2005 | Schenk et al. |
| 2005/0249727 A1 | 11/2005 | Schenk |
| 2005/0260697 A1 | 11/2005 | Wang et al. |
| 2006/0062859 A1 | 3/2006 | Blum |
| 2006/0165682 A1 | 7/2006 | Basi et al. |
| 2006/0235207 A1 | 10/2006 | Tsuchiya et al. |
| 2006/0240485 A1 | 10/2006 | Hock |
| 2006/0257396 A1 | 11/2006 | Jacobsen |
| 2007/0031416 A1 | 2/2007 | Shoji et al. |
| 2007/0190046 A1 | 8/2007 | DeMaattos et al. |
| 2008/0050367 A1 | 2/2008 | Basi et al. |
| 2008/0281082 A1 | 11/2008 | Basi et al. |
| 2008/0292625 A1 | 11/2008 | Schroeter et al. |
| 2008/0300204 A1 | 12/2008 | Federoff et al. |
| 2009/0035295 A1 | 2/2009 | Hillen et al. |
| 2009/0041771 A1 | 2/2009 | St. George-Hyslop et al. |
| 2009/0069268 A1 | 3/2009 | Shepard et al. |
| 2009/0069544 A1 | 3/2009 | Basi et al. |
| 2009/0191190 A1 | 7/2009 | Barghorn et al. |
| 2009/0191231 A1 | 7/2009 | Schenk et al. |
| 2009/0214515 A1 | 8/2009 | Holzman et al. |
| 2009/0238831 A1 | 9/2009 | Hillen et al. |
| 2009/0246145 A1 | 10/2009 | Small |
| 2010/0120787 A1 | 5/2010 | Sutcliffe et al. |
| 2010/0202968 A1 | 8/2010 | Nitsch et al. |
| 2010/0209417 A1 | 8/2010 | Lee et al. |
| 2010/0209422 A1 | 8/2010 | Ravetch et al. |
| 2010/0221187 A1 | 9/2010 | Lieberburg et al. |
| 2010/0239591 A1 | 9/2010 | Kidd et al. |
| 2010/0266596 A1 | 10/2010 | Cox |
| 2010/0279433 A1 | 11/2010 | Holtzman et al. |
| 2010/0297108 A1 | 11/2010 | Henco et al. |
| 2011/0044985 A1 | 2/2011 | Rosenthal et al. |
| 2011/0052498 A1 | 3/2011 | Lannfelt et al. |
| 2011/0059092 A1 | 3/2011 | Vannechelen et al. |
| 2011/0044986 A1 | 4/2011 | Biere-Citron et al. |
| 2011/0135660 A1 | 6/2011 | Schenk et al. |
| 2011/0152341 A1 | 6/2011 | Schilling et al. |
| 2011/0182809 A1 | 7/2011 | Nitsch et al. |
| 2011/0200609 A1 | 8/2011 | Glabe et al. |
| 2011/0212109 A1 | 9/2011 | Barghorn et al. |
| 2011/0229413 A1 | 9/2011 | Lieberburg et al. |
| 2011/0237537 A1 | 9/2011 | Lombard et al. |
| 2011/0287005 A1 | 11/2011 | Hillen et al. |
| 2011/0306756 A1 | 12/2011 | Schenk |
| 2012/0027755 A1 | 2/2012 | Lannfelt et al. |
| 2012/0082667 A1 | 4/2012 | Yokoseki et al. |
| 2012/0156193 A1 | 6/2012 | Yokoseki et al. |
| 2012/0177664 A1 | 7/2012 | Yokoseki et al. |
| 2013/0164367 A1 | 6/2013 | Oddo et al. |
| 2013/0216555 A1 | 8/2013 | Nitsch et al. |
| 2013/0266514 A1 | 10/2013 | Nitsch et al. |
| 2013/0266585 A1 | 10/2013 | Nitsch et al. |
| 2013/0266586 A1 | 10/2013 | Nitsch et al. |
| 2014/0272950 A1 | 9/2014 | Wang et al. |
| 2014/0274764 A1 | 9/2014 | Zhu et al. |
| 2014/0323424 A1 | 10/2014 | Lombard et al. |
| 2015/0147343 A1 | 5/2015 | Nitsch et al. |
| 2015/0315267 A1 | 11/2015 | Bussiere et al. |
| 2016/0177390 A1 | 6/2016 | Feng et al. |
| 2016/0289310 A1 | 10/2016 | Nitsch et al. |

FOREIGN PATENT DOCUMENTS

| | | |
|---|---|---|
| EP | 1 185 296 | 3/2002 |
| EP | 1 185 298 | 3/2002 |
| EP | 1 212 088 | 6/2002 |
| EP | 1 358 213 | 11/2003 |
| EP | 1 613 347 | 1/2006 |
| EP | 1 679 080 | 7/2006 |
| EP | 1 690 547 | 8/2006 |
| EP | 1 720 909 | 11/2006 |
| EP | 1 741 783 | 1/2007 |
| EP | 1 766 396 | 3/2007 |
| EP | 1 861 422 | 5/2007 |
| EP | 1 994 937 | 11/2008 |
| EP | 2 045 267 | 4/2009 |
| EP | 2 108 376 | 10/2009 |
| EP | 2 204 381 | 7/2010 |
| EP | 2 210 901 | 7/2010 |
| EP | 2 305 282 | 4/2011 |
| EP | 2 305 709 | 4/2011 |
| EP | 2 361 629 | 8/2011 |
| EP | 2 364 719 | 9/2011 |
| JP | 2003-509020 | 3/2003 |
| JP | 2006-265189 | 10/2006 |
| JP | 2007-536895 | 12/2007 |
| JP | 2008-524247 | 7/2008 |
| JP | 2008-309778 | 12/2008 |
| JP | 2009-519708 | 5/2009 |
| SG | 177954 | 2/2012 |
| WO | WO 1993/014125 | 7/1993 |
| WO | WO 1999/050300 | 10/1999 |
| WO | WO 2001/018169 | 3/2001 |
| WO | WO 2001/031056 | 5/2001 |
| WO | WO 2001/098361 | 12/2001 |
| WO | WO 2003/069332 | 8/2003 |
| WO | WO 2003/074081 | 9/2003 |
| WO | WO 2003/077858 | 9/2003 |
| WO | WO 2004/032868 | 4/2004 |
| WO | WO 2004/095031 | 11/2004 |
| WO | WO 2004/108895 | 12/2004 |
| WO | WO 2005/018424 | 3/2005 |
| WO | WO 2005/025616 | 3/2005 |
| WO | WO 2005/047860 | 5/2005 |
| WO | WO 2005/060641 | 7/2005 |
| WO | WO 2005/123775 | 12/2005 |
| WO | WO 2006/020581 | 2/2006 |
| WO | WO 2006/050041 | 5/2006 |
| WO | WO 2006/066171 | 6/2006 |
| WO | WO 2006/103116 | 10/2006 |
| WO | WO 2006/116192 | 11/2006 |
| WO | WO 2006/118959 | 11/2006 |
| WO | WO 2007/011907 | 1/2007 |
| WO | WO 2007/012061 | 1/2007 |
| WO | WO 2007/021255 | 2/2007 |
| WO | WO 2007/068412 | 6/2007 |
| WO | WO 2008/081008 | 7/2008 |
| WO | WO 2008/103472 | 8/2008 |
| WO | WO 2008/110372 | 9/2008 |
| WO | WO 2008/131298 | 10/2008 |
| WO | WO 2008/148884 | 12/2008 |
| WO | WO 2009/033743 | 3/2009 |
| WO | WO 2009/040134 | 4/2009 |
| WO | WO 2009/094592 | 7/2009 |
| WO | WO 2010/004434 | 1/2010 |
| WO | WO 2010/032059 | 3/2010 |
| WO | WO 2010/069603 | 6/2010 |
| WO | WO 2011/064225 | 6/2011 |
| WO | WO 2011/072091 | 6/2011 |
| WO | WO 2012/005838 | 1/2012 |
| WO | WO 2012/021469 | 2/2012 |

(56) References Cited

FOREIGN PATENT DOCUMENTS

| WO | WO 2012/049570 | 4/2012 |
|----|----------------|--------|
| WO | WO 2012/080518 | 6/2012 |
| WO | WO 2012/174262 | 12/2012 |
| WO | WO 2013/061163 | 5/2013 |
| WO | WO 2013/140349 | 9/2013 |
| WO | WO 2014/041069 | 3/2014 |
| WO | WO 2014/089500 | 6/2014 |
| WO | WO 2015/175769 | 11/2015 |
| WO | WO 2015/191825 | 12/2015 |
| WO | WO 2016/087944 | 6/2016 |

OTHER PUBLICATIONS

"Biogen Antibody Buoyed by Phase 1 Data and Hungry Investors" [online] ALZFORUM, by Biomedical Research Forum, LLC, first available online Mar. 25, 2015, [Retrieved on Jun. 12, 2015], 9 pages.

"Human-Derived SOD1 Antibodies Show Promise in ALS Mice," [online] ALZFORUM, by Biomedical Research Forum, LLC, first available online Apr. 17, 2013, [Retrieved on Jul. 28, 2014], Retrieved from the Internet: URL <http://www.alzforum.org/news/conference-coverage/human-derived-sod1-antibodies-show-promis-als-mice> 1 pages.

"Multiple Dose Study of BIIB037 in Subjects With Prodromal or Mild Alzheimer's Disease," [online] ClinicalTrials.gov, U.S. National Library of Medicine, first available online Aug. 30, 2012, [Retrieved on Jul. 28, 2014], Retrieved from the Internet: URL <https://clinicaltrials.gov/ct2/show/study/NCT01677572> 1 page.

"The advantages of using recombinant antibodies," [online] Absolute Antibody, [Retrieved on Jun. 28, 2016], Retrieved from the Internet: URL <http://absoluteantibody.com/about-us/advantages-of-recombinant-antibodies/>, 1 page.

"The Dictionary of Immunology," Academic Press, Fourth Edition, Harcourt Brace & Company, (1995), 3 pages.

Abcam, "Anti-pan Synuclein antibody (ab6176)," Abeam Inc., United States, available online on or before Jun. 26, 2012, Retrieved from the Internet: URL <http://www.abcam.com/pan-synuclein-antibody-ab6176.html>, 2 pages.

Adderson et al., "Molecular Analysis of Polyreactive Monoclonal Antibodies from Rheumatic Carditis: Human Anti-N-Acetylglucosamine/Anti-Myosin Antibody V Region Genes," J Immunol, 161:2020-2031, Aug. 15, 1998, 13 pages.

Alloul et al., "Alzheimer's disease: a review of the disease, its epidemiology and economic impact," Arch Gerontol Geriatr, 27:198-221, Nov. 2, 1998, 33 pages.

Andreasen et al., "First Administration of the Fc-Attenuated Anti-[beta] Amyloid Antibody GSK933776 to Patients with Mild Alzheimer's Disease: A Randomized, Placebo-Controlled Study," PLOS One 10(3):e0098153 (2015).

Baba et al., "Aggregation of a-Synuclein in Lewy Bodies of Sporadic Parkinson's Disease and Dementia with Lewy Bodies," Am J Pathol 152(4):879-884, Apr. 1998, 6 pages.

Bard et al., "Epitope and isotype specificities of antibodies to β-amyloid peptide for protection against Alzheimer's disease-like neuropathology," PNAS 100(4):2023-2028, Feb. 2003, 6 pages.

Bard et al., "Peripherally administered antibodies against amyloid β-peptide enter the central nervous system and reduce pathology in a mouse model of Alzheimer disease," Nat Med 6(8):916-919, Aug. 2000, 4 pages.

Basi et al., "Structural Correlates of Antibodies Associated with Acute Reversal of Amyloid 13-related Behavioral Deficits in a Mouse Model of Alzheimer Disease," J Biol Chem, 285(5):3417-3427, Jan. 2010, 12 pages.

Bayer and Wirths, "Intraneuronal Aβ as a trigger for neuron loss: Can this be translated into human pathology?" Biochem Soc Trans, 39(4):857-861, Jan. 1, 2011, 5 pages.

BD Transduction Laboratories, "Technical Data Sheet: Purified Mouse Anti-a-Synuclein," BD Biosciences, available online on or before Jun. 27, 2012, [Retrieved on Mar. 3, 2016], Retrieved from the Internet: URL<http://www.bdbiosciences.com/ds/pm/tds/610787.pdf>, 2 pages.

Becker et al., "Stimulation of endogenous neurogenesis by anti-EFRH immunization in a transgenic mouse model of Alzheimer's disease," Proc. Natl. Acad. Sci. USA 104(5):1691-1696, Jan. 2007, 6 pages.

Bernasconi et al., "Maintenance of Serological Memory by Polyclonal Activation of Human Memory B Cells," Science 298:2199-2202, Dec. 2002, 3 pages.

Biscaro et al., "Aβ immunotherapy Protects Morphology and Survival of Adult-Born Neurons in Doubly Transgenic APP/PSI Mice," J Neurosci 29(45): 14108-14119, Nov. 2009, 12 pages.

Bohrmann et al., "Gantenerumab: A Novel Human Anti-A13 Antibody Demonstrates Sustained Cerebral Amyloid-13 Binding and Elicits Cell-Mediated Removal of Human Amyloid-β," J Alzheimer's Dis, 28(1):49-69, 2012, 21 pages.

BusinessWire [online], "Biogen Presents New Data from Phase 1B Study of Investigational Alzheimer's Disease Treatment Aducanumab (BIIB037) at Alzheimer's Association International Conference® 2015," Jul. 22, 2015, [Retrieved on Mar. 3, 2016], Retrieved from the Internet: URL<http://www.businesswire.com/news/home/20150722005352/en/Biogen-Presents-Data-Phase-1B-Study-Investigational>, 5 pages.

Buttini et al., "β-Amyloid Immunotherapy Presents Synaptic Degeneration in a Mouse Model of Alzheimer's Disease," J Neurosci 25:9096-9101, Oct. 2005, 6 pages.

Buxbaum et al. "Molecular dissection of NRG1-ERBB4 signaling implicates PTPRZ1 as a potential schizophrenia susceptibility gene," Mol. Psychiatry 2008;13:162-172.

Buxbaum, "The systemic amyloidosis," Current Opinion in Rheumatology, 16:67-75 (2004).

Campbell, "β-amyloid: friend or foe," Med Hypot, 56(3):388-391, Mar. 2001, 4 pages.

Casset et al., "A peptide mimetic of an anti-CD4 monoclonal antibody by rational design," Biochem and Biophys Res Comm 307:198-205, Jul. 2003, 8 pages.

Chen et al., "Selection and Analysis of an Optimized Ant-VEGF Antibody: Crystal Structure of an Affinity-matured Fab in Complex with Antigen," J Mol Biol 293:965-881, Nov. 1999, 17 pages.

Choi et al. "Fine epitope mapping of monoclonal antibodies specific to human alpha-synuclein," Neuroscience Letters, 397(1-2):53-58, Apr. 2006, 6 pages.

Cohn, "Introduction to Surrogate Markers," Circulation, 109[suppl IV]: IV-20-IV-21 (2004).

Das et al. "Amyloid-β Immunization Effectively Reduces Amyloid Deposition in FcRy Knock-Out Mice," J Neurosci, 23(24):8532-8538, Sep. 2003, 7 pages.

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol 169:3076-3084, Sep. 2002, 9 pages.

DeMattos et al., "Peripheral anti-Aβ antibody alters CNS and plasma Aβ clearance and decreases brain Aβ burden in a mouse model of Alzheimer's disease," Proc Natl Acad Sci USA, 98:8850-8855, Jul. 2001, 6 pages.

Department of Health and Human Services, Food and Drug Administration, Memorandum of Meeting Minutes with Biogen Idec, with cover letter and signature page by Director Russell G. Katz, dated Nov. 19, 2009; received Dec. 2, 2009, 9 pages.

Du et al., "Human anti-β-amyloid antibodies block β-amyloid fibril formation and prevent β-amyloid-induced neurotoxicity," Brain 126:1935-1939, Sep. 2003, 5 pages.

Dunn et al., "The Immunobiology of Cancer Immunosurveillance and Immunoediting," Immunity 21:137-1498, Aug. 2004, 12 pages.

Dunstan et al., "The role of brain macrophages on the clearance of amyloid plaques following the treatment of Tc2576 with BIIB037," Alzheimer's & Dementia: The Journal of the Alzheimer's Association, 7(4):S700, Jul. 2011, 3 pages.

El-Agnaf et al., "a-Synuclein implicated in Parkinson's disease is present in extracellular biological fluids, including human plasma," FASEB J., 17( 13): 1945-1947, Oct. 2003, 3 pages.

(56) References Cited

OTHER PUBLICATIONS

El-Agnaf et al., "Detection of oligomeric forms of a-synuclein protein in human plasma as a potential biomarker for Parkinson's disease," FASEB J., 20:419-425, 2006, 7 pages.
Emadi et al., "Inhibiting Aggregation of a-Synuclein with Human Single Chain Antibody Fragments," Biochem, 43(10):2871-2878, Mar. 2004, 10 pages.
Emadi et al., "Isolation of a human single chain antibody fragment against oligomeric a-synuclein that inhibits aggregation and prevents a-synuclein-induced toxicity" J. Mol Biol, 368(4):1132-1144, May 2007, 13 pages.
Email from Edward Stuart, CEO of Neurimmune Therapeutics AG, to Leslie Coney, Biogen IDEC, dated Nov. 1, 2007, 1 page.
Email from Jan Grimm of Neurimmune, to Ken Rhodes of Biogen IDEC, dated Oct. 13, 2009, 1 page.
Emmanouilidou et al., "Assessment of a-Synuclein Secretion in Mouse and Human Brain Parenchyma," PLoS One, 6(6):e22225, doi: 10.1371/journal.pone.0022225, Jul. 2011, 9 pages.
Esposito et al., "Neuronal Differentiation in the Adult Hippocampus Recapitulates Embryonic Development," J. Neurosci. 25(44):10074-10086, Nov. 2005, 13 pages.
European Office Action in European Application No. 09786187.6, dated Nov. 11, 2016, 8 pages.
European Search Report and Written Opinion in European Application No. 11185486, dated Mar. 7, 2012, 11 pages.
European Search Report and Written Opinion in European Application No. 12802721, dated Feb. 2, 2015, 16 pages.
European Search Report in European Application No. 17169749.3, dated Aug. 1, 2017, 14 pages.
Extended Search Report and Written Opinion in European Application No. 12846452, dated May 21, 2015, 4 pages.
Ge et al., "GABA regulates synaptic integration of newly generated neurons in the adult brain," Nature 439(2):589-593, Jul. 2006, 10 pages.
Gelfanova et al., "Quantitative analysis of amyloid-beta peptides in cerebrospinal fluid using immunoprecipitation and MALDI-Tof mass spectrometry," Briefings in Functional Genomics and Proteomics, 6(2):149-158, Jun. 1, 2007, 10 pages.
GenBank Accession No. P37840.1, GI Number: 586067, "RecName: Full=Alpha-synuclein; AltName: Full=Non-A beta component of AD amyloid; AltName: Full=Non-A4 component of amyloid precursor; Short=NACP," dated Jun. 15, 2012, 11 pages.
GenBank Accession No. S56746, GI Number: 1362748, "alpha-synuclein, NAC—human(fragment)," dated Jul. 17, 2007, 1 page.
George et al., "a-Synuclein transgenic mice exhibit reduced anxiety-like behavior," Exp Neural, 210:788-792, Apr. 2008, 5 pages.
George, "The Synucleins," Genome Biol, 3(1):reviews 3002.1-3002. 6, Dec. 2001, 6 pages.
Geylis and Steinitz, "Immunotherapy of Alzheimer's disease (AD): From murine models to anti-amyloid beta (Aβ) human monoclonal antibodies," Autoimmunity Reviews 5:33-39, Jan. 2006, 7 pages.
Geylis et al., "Human monoclonal antibodies against amyloid-beta from healthy adults," Neurobiol of Aging, 26:597-606, May 2005, 10 pages.
Giasson et al., "A Panel of Epitope-Specific Antibodies Detects Protein Domains Distributed Throughout Human a-Synuclein in Lewy Bodies of Parkinson's Disease," J Neurosci Res, 59:528-533, 2000, 6 pages.
Giasson et al., "Neuronal a-Synucleinopathy with Severe Movement Disorder in Mice Expressing A53T Human a-Synuclein," Neuron, 34:521-533, May 2002, 13 pages.
Giraudon et al., "Semaphorin CD100 from Activated T Lymphocytes Induces Process Extension Collapse in Oligodendrocytes and Death of Immature Neural Cells," J Immunol, 172:1246-1255, Jan. 2004, 11 pages.
Gupta et al., "A Novel human-derived antibody against NY-ESO-1 improves the efficacy of chemotherapy," Cancer Immunity, 13:1-9 (Jan. 2013).

Haass et al., "Amyloid β-peptide is produced by cultured cells during normal metabolism," Nature, 359:322-325, Sep. 1992, 4 pages.
Hantman and Perl, "Molecular and Genetic Features of a Labeled Class of Spinal Substantia Gelatinosa Neurons in a Transgenic Mouse," J Comp Neurol, 492:90-100, Wiley-Liss, Inc., 2005, 11 pages.
Hasan Mohajeri et al., "Passive immunization against beta-amyloid peptide protects central nervous system (CNS) neurons from increased vulnerability associated with an Alzheimer's disease-causing mutation," Journal of Biological Chemistry, American Society for Biochemistry and Molecular Biology U.S., 277(36):33012-33017 (Sep. 2002).
Hashimoto et al., "A novel approach for Aβ1-40 quantification using immuno-PCR," J Neurosci Meth, 205(2):364-367, Jan. 25, 2012, 4 pages.
Ho et al., "In vivo imaging of adult human hippocampal neurogenesis: progress, pitfalls and promise," Mol Psychiatry, 18(4):404-416, Nature Publishing Group, Feb. 2013, 14 pages.
Hock and Nitsch, "Clinical Observations with AN-1792 Using TAPIR Analyses," Neurodeg Dis 2:273-276, 2005, 4 pages.
Hock et al., "Antibodies against β-Amyloid Slow Cognitive Decline in Alzheimer's Disease," Neuron, 38(4):547-554, May 2003, 8 pages.
Hock et al., "Generation of antibodies specific for β-amyloid by vaccination of patients with Alzheimer disease," Nat Med, 8(11):1270-1275, 2002, 6 pages.
Holcomb et al., "Accelerated Alzheimer-type phenotype in transgenic mice carrying both mutant amyloid precursor protein and presenilin I transgenes," Nat. Med. 4(1):97-100, Nature Publishing Group, Jan. 1998, 4 pages.
Holm et al., "Functional mapping and single chain construction of the anti-cytokeratin 8 monoclonal antibody TS1," Mol Immunol 44:1075-1084, 2007, 10 pages.
Hsiao et al., "Correlative Memory Deficits, Aβ Elevation, and Amyloid Plaques in Transgenic Mice," Science 274(5284):99-102, American Associate for the Advancement of Science, Oct. 1996, 4 pages.
Hyman et al., "Autoantibodies to Amyloid-β and Alzheimer's Disease," Ann Neurol 49:808-810, 2001, 5 pages.
International Preliminary Report on Patentability and Written Opinion in International Application No. PCT/EP2008/000053, dated Jul. 7, 2009, 10 pages.
International Preliminary Report on Patentability and Written Opinion in International Application No. PCT/IB2009/006666, dated Jan. 11, 2011, 10 pages.
International Preliminary Report on Patentability and Written Opinion in International Application No. PCT/US2013/073700, dated Jun. 9, 2015, 10 pages.
International Preliminary Report on Patentability and Written Opinion in International Application No. PCT/US2014/045994, dated Jan. 12, 2016, 15 pages.
International Search Report and Written Opinion in International Application No. PCT/US2012/062430, dated Jan. 24, 2013, 10 pages.
International Search Report and Written Opinion in International Application No. PCT/EP2009/009186, dated Mar. 12, 2010, 11 pages.
International Search Report and Written Opinion in International Application No. PCT/IB2009/006666, dated Feb. 22, 2010, 16 pages.
International Search Report and Written Opinion in International Application No. PCT/US2012/043701, dated Sep. 26, 2012, 11 pages.
International Search Report and Written Opinion in International Application No. PCT/US2013/073700, dated Mar. 3, 2014, 13 pages.
International Search Report and Written Opinion in International Application No. PCT/US2014/045994, dated Nov. 3, 2014, 19 pages.
International Search Report and Written Opinion in International Application No. PCT/US2015/030753, dated Aug. 27, 2015, 11 pages.

(56) References Cited

OTHER PUBLICATIONS

International Search Report and Written Opinion in International Application No. PCT/US2015/035282, dated Sep. 29, 2015, 18 pages.
International Search Report and Written Opinion in International Application No. PCT/IB2015/002465, dated Jun. 9, 2016, 18 pages.
Invitrogen Corp, "Mouse anti-a-Synuclein: For In Vitro Diagnostic Use," Product information, revision date Aug. 2008, accessed on Jul. 2, 2012, 3 pages.
Iwai et al., "Non-Aβ Component of Alzheimer's Disease Amyloid (NAG) Is Amyloidogenic," Biochemistry, 34:10139-10145, 1995, 8 pages.
Jakes et al., "Epitope mapping of LB509, a monoclonal antibody directed against human a-synuclein," Neurosci Lett, 269:13-16, 1999, 4 pages.
Janus et al., "Aβ peptide immunization reduces behavioural impairment and plaques in a model of Alzheimer's disease," Nature 408: 979-982, Dec. 2000, 4 pages.
Janus et al., "Spatial learning in transgenic mice expressing human presenilin 1 (PS1) transgenes," Neurobiol Aging, 21(4):541-549, 2000, 9 pages.
Jawhar et al., "Pyroglutamate amyloid-β (Aβ): a hatchet man in Alzheimer disease," J Biol Chem, 286(45):38825-38832, Nov. 11, 2011, 9 pages.
Jensen et al., "Residues in the synuclein consensus motif of the a-synuclein fragment, NAG, participate in transglutaminase-catalysed cross-linking to Alzheimer-disease amyloid 13A4 peptide," Biochem J, 310:91-94, Aug. 1995, 4 pages.
Jin et al., "Vascular endothelial growth factor (VEGF) stimulates neurogenesis in vitro and in vivo," Proc Natl Acad Sci USA 99(18): 11946-11950, National Academy of Sciences, Sep. 2002, 5 pages.
Kadir et al., "Positron emission tomography imaging and clinical progression in relation to molecular pathology in the first Pittsburgh Compound B positron emission tomography patient with Alzheimer's disease," Brain, 134(1):301-317, Jan. 1, 2011, 17 pages.
Kahle et al., "Selective Insolubility of a-Synuclein in Human Lewy Body Diseases Is Recapitulated in a Transgenic Mouse Model," Am J Pathol, 159(6):2215-2225, Dec. 2001, 11 pages.
Kahle et al., "Subcellular Localization of Wild-Type and Parkinson's Disease-Associated Mutant a-Synuclein in Human and Transgenic Mouse Brain," J Neurosci, 20(17):6365-6373, Sep. 2000, 9 pages.
Kastanenka et al., "Amelioration of calcium dyshomeostasis by immunotherapy with BIIB037 in Tg2576 mice," Alzheimer's & Dementia: The Journal of the Alzheimer's Association, 9(4):P508, Jul. 2013.
Kawarabayashi et al., "Age-Dependent Changes in Brain, CSF, and Plasma Amyloid 13 Protein in the Tg2576 Transgenic Mouse Model of Alzheimer's Disease," J Neurosci, 21 (2):372-381, Jan. 2001, 10 pages.
Knobloch et al., "Intracellular Aβ and cognitive deficits precede β-amyloid deposition in transgenic arcAβ mice," Neurobiol Aging 28(9):1297-1306, Sep. 2007, 10 pages.
Kohler and Milstein, "Continuous cultures of fused cells secreting antibody of predefined specificity," Nature 256:495-497, 1975, 5 pages.
Kumanogoh et al., "Requirement for the Lymphocyte Semaphorin, CD100, in the Induction of Antigen-Specific T Cells and the Maturation of Dendritic Cells," J Immunol, 169:1175-1181, Aug. 2002, 7 pages.
Larrick et al., "Recombinant antibodies," Hum Antibod Hybridoma, 2:172-189 (1991), abstract.
Laske et al., "Higher BDNF serum levels predict slower cognitive decline in Alzheimer's disease patients," International Journal of Neuropsychopharmacology, 14(3):399-404 (Apr. 2011).
Laurén et al., "Cellular prion protein mediates impairment of synaptic plasticity by amyloid-beta oligomers," Nature 457: 1128-1132, Macmillan Publishers Limited, 2009, 13 pages.
Lee et al., "Enzyme-linked immunosorbent assays for alpha-synuclein with species and multimeric state specificities," J Neurosci Meth, 199(2):249-257, 2011, 9 pages.
Lee et al., "Stereological analysis of microvascular parameters in a double transgenic model of Alzheimer's disease," Brain Res Bull 65(4) :3 17-322, Elsevier Science, 2005, 6 pages.
Lee et al., "Targeting Amyloid-beta Peptide (Abeta) Oligomers by Passive Immunization with a Conformation-selective Monoclonal Antibody Improves Learning and Memory in abeta Precursor Protein (APP) Transgenic Mice," Journal of Biological Chemistry, American Society for Biochemistry and Molecular Biology, 281(7):4292-4299, Feb. 2006.
Lehman et al., "Amino acid sequence of the variable region of a humanμ chain: Location of a possible JH segment," Proc Natl Acad Sci USA, 77(6):3239-3243, Jun. 1980, 5 pages.
Lewczuk et al., "Amyloid β peptides in cerebrospinal fluid as profiled with surface enhanced laser desorption/ionization time-of-flight mass spectrometry: evidence of novel biomarkers in Alzheimer's disease," Biol Psych, 55(5):524-530, Mar. 1, 2004, 7 pages.
Lim et al., "APOE and BDNF polymorphisms moderate amyloid β-related cognitive decline in preclinical Alzheimer's disease," Mol Psychi, 1-7, Oct. 7, 2014, 7 pages.
Lim et al., "BDNF Va166Met, Ab amyloid, and cognitive decline in preclinical Alzheimer's disease," Neurobiol of Aging, 34(11):2457-2464, Jun. 13, 2013, 8 pages.
Lim et al., "Effect of BDNF Va166Met on Memory Decline and Hippocampal Atrophy in Prodromal Alzheimer's Disease: A Preliminary Study," PLoS One, 9(1):1-5, Jan. 27, 2014, 5 pages.
Lippa et al., "Antibodies to a-Synuclein Detect Lewy Bodies in Many Down's Syndrome Brains with Alzheimer's Disease," Ann Neural, 45(3):353-357, Mar. 1999, 7 pages.
Liu et al., "Amyloid β peptide alters intracellular vesicle trafficking and cholesterol homeostasis," Proc Natl Acad Sci USA, 95:13266-13271, Oct. 1998, 6 pages.
Lobello et al., "Targeting Beta Amyloid: A Clinical Review of Immunotherapeutic Approaches in Alzheimer's Disease," International Journal of Alzheimer's Disease 6(4):S305-14 (2012).
Lopez-Toledano and Shelanksi, "Neurogenic Effect of β-Amyloid Peptide in the Development of Neural Stem Cells," J Neurosci, 24:5439-5444, Jun. 2004, 6 pages.
Lu et al., "BDNF-based synaptic repair as a disease-modifying strategy for neurodegenerative diseases," Nature Reviews Neuroscience, 14:401-416 (May 2013).
Lynch et al., "An ScFv Intrabody Against the Non-Amyloid Component of Alpha Synuclein Reduces Intracellular Aggregation and Toxicity," NIH Public Access Author Manuscript; final publication in J. Mol Biol. 377(1):136-147, Mar. 2008, 17 pages.
MacCallum et al., "Antibody-antigen Interactions: Contact Analysis and Binding Site Topography," J Mol Biol 262:732-745, 1996, 14 pages.
Maguire-Zeiss et al., "Identification of human alpha-synuclein specific single chain antibodies," Biochem Biophys Res Commun, 349(4):1198-1205, 2006, 25 pages.
Masliah et al., "Dopaminergic loss and inclusion body formation in alpha-synuclein mice: implications for neurodegenerative disorders," Science, 287(5456):1265-1269, Feb. 2000, 5 pages.
Masliah et al., "Effects of a-Synuclein Immunization in a Mouse Model of Parkinson's Disease," Neuron, 46:857-868, 2005, 12 pages.
Masters et al., "Amyloid plaque core protein in Alzheimer disease and Down syndrome," Proc Natl Acad Sci USA 82:4245-4249, Jun. 1985, 5 pages.
Masuda et al., "Inhibition of a-synuclein fibril assembly by small molecules: Analysis using epitopespecific antibodies," FEBS Lett, 583(4):787-791, Feb. 2009, 5 pages.
Mcheyzer-Williams and Ahmed, "B cell memory and the long-lived plasma cell," Curr Opin Immunol, 11:172-179, Apr. 1999, 10 pages.
McLaurin et al., "Therapeutically effective antibodies against amyloid-13 peptide target amyloid-β residues 4-10 and inhibit cytotoxicity and fibrillogenesis," Nat Med, 8: 1263-1269, Oct. 2002, 7 pages.
Miller and Messer, "Intrabody Applications in Neurological Disorders: Progress and Future Prospects," Molecular Therapy, 12(3):394-401, Sep. 2005, 8 pages.

(56) References Cited

OTHER PUBLICATIONS

Mollenhauer et al., "Direct quantification of CSF a-synuclein by ELISA and first cross-sectional study in patients with neurodegeneration," Exp Neural, 213(2):315-325, Oct. 2008, 11 pages.

Mollenhauer et al., "Quantification of alpha-synuclein in cerebrospinal fluid as a biomarker candidate: review of the literature and considerations for future studies," Biomarkers in Medicine, 4(5):683-699, 2010, 17 pages.

Moreth et al., "Passive anti-amyloid immunotherapy in Alzheimer's disease: What are the most promising targets?," Immunity and Ageing, Biomed Central, London, GB, 10(1):18, May 2013.

Morgan et al., "Aβ peptide vaccination prevents memory loss in an animal model of Alzheimer's disease," Nature, 408:982-985, Dec. 2000, 13 pages.

Mougenot et al., "Production of a monoclonal antibody, against human a-synuclein, in a subpopulation of C57BL/6J mice, presenting a deletion of the a-synuclein locus," J Neurosci Meth, 192(2):268-276, 2010, 9 pages.

Mruthinti et al., "Autoimmunity in Alzheimer's disease: increased levels of circulating IgGs binding Aβ and RAGE peptides," Neurobiol Aging, 25:1023-1032, 2004, 10 pages.

Mueggler et al., "Compromised Hemodynamic Response in Amyloid Precursor Protein Transgenic Mice," J Neurosci, 22:7218-7224, Aug. 2002, 7 pages.

Muller et al., "TransMabs: cell penetrating antibodies, the next generation," Expert Opin Biol Ther, 5(2):237-241, Apr. 2005, 5 pages.

Racke et al., "Exacerbation of Cerebral Amyloid Angiopathy-Associated Microhemorrhage in Amyloid Precursor Protein Transgenic Mice by Immunotherapy is Dependent on Antibody Recognition of Deposited Forms of Amyloid β," J Neurosci 25:629-636, Jan. 2005, 8 pages.

Robert et al., "Engineered antibody intervention strategies for Alzheimer's disease and related dementias by targeting amyloid and toxic oligomers" Protein Eng Des Sel, 22(3):199-208, 2009, 10 pages.

Rudikoff et al., "Single amino acid substitution altering antigen-binding specificity," Proc Natl Acad Sci, 79:1979-1983, Mar. 1982, 5 pages.

Ruszczycki et al., "Sampling issues in quantitative analysis of dendritic spines morphology," BMC Bioinformatics, 13:213, 2012, 12 pages.

Ryu and Chen, "Development of Alzheimer's disease imaging agents for clinical studies," Front Biosci, 13:777-789, Jan. 2008, 13 pages.

Schenk et al., "Amyloid-β immunotherapy for Alzheimer's disease: the end of the beginning," Nat Rev Neurosci, 3(10):824-828, Oct. 2002, 6 pages.

Schenk et al., "Immunization with amyloid-beta attenuates Alzheimer-disease-like pathology in the PDAPP mouse," Nature, 400:173-177, Jul. 1999, 5 pages.

Seitz et al., "Isolation and Charakterisierung eines physiologisch vorkommenden Autoantikorpers gegen humanes alpha-Synuclein," 35:S86, Abstract P528, Sep. 2008, 6 pages.

Serrano-Pozo et al., "Neuropathological Alterations in Alzheimer Disease," Cold Spring Harb. Perspect. Med., 1:a006189, 23 pages, 2011, 23 pages.

Sevigny, et al., "Randomized double-blind, placebo-controlled, phase 1b study of aducanumab (BIIB037), an anti-Ab monoclonal antibody, in patients with prodromal or mild Alzheimer's disease; interim results by disease stage and ApoE4 status," Neurology 85(4):E44 (2015).

Shankar et al., "Natural oligomers of the Alzheimer amyloid-beta protein induce reversible synapse loss by modulating an NMDA-type glutamate receptor-dependent signaling pathway," J Neurosci, 27(11):2866-2875, Mar. 2007, 10 pages.

Shi et al., "The Class IV Semaphorin CD100 Plays Non redundant Roles in the Immune System: Defective Band T Cell Activation in CD100-Deficient Mice," Immunity, 13:633-642, Nov. 2000, 10 pages.

Sierra et al., "Adult human neurogenesis: from microscopy to magnetic resonance imaging," Front Neurosci, 5(47):1-18, Apr. 2011, 18 pages.

Sigma-Aldrich, Inc., "Monoclonal Anti-a-Synuclein. Clone Syn211. Purified mouse immunoglobulin. Product No. S 5566," Product Information, updated Jan. 2003, accessed on Mar. 3, 2016, 2 pages.

Sigmund, C., "Viewpoint: Are studies in genetically altered mice out of control?" Arterioscler. Thromb. Vasc. Biology 20:1425-1429 (2000).

Simpson et al., "Antibodies to normal and Alzheimer human brain structures from non-immunised mice of various ages," FEBS Letters 217:62-64, Jun. 1987, 3 pages.

Simpson et al., "Autoantibodies to Alzheimer and Normal Brain Structures from Virus-Transformed Lymphocytes," J Neuroimmunol, 13:1-8, 1986, 4 pages.

Singapore Patent Application No. 201200075-8, filed Jan. 7, 2008, 127 pages.

Skovronsky et al., "Neurodegenerative Diseases: New Concepts of Pathogenesis and Their Therapeutic Implications," Annu. Rev. Pathol. Mech. Disease, 1:151-170 (2006).

SNP Cluster Report: rs6946211, [accessed: Apr. 19, 2017], retrieved from the internet: URL <https://www.ncbi.nlm.nih.gov/SNP/snp_ref.cgi?rs=6946211&pt=1V7XNyo5DVBB_0NHALSkRXG4eofetRo6uOUrVB6VklwEM4a5d>, 3 pages.

Sorra and Harris, "Overview on the Structure, Composition, Function, Development and Plasticity of Hippocampal Dendritic Spines," Hippocampus 10:501-511, 2000, 11 pages.

Supplementary European Search Report in European Application No. 13860755, dated Sep. 20, 2016, 13 pages.

Supplementary European Search Report in European Application No. 14822788, dated Dec. 16, 2016, 8 pages.

Thakker et al., "Intracerebroventricular amyloid-β antibodies reduce cerebral amyloid angiopathy and associated micro-hemorrhages in aged Tg2576 mic,e" Proc Natl Acad Sci USA, 106(11):4501-4506, Mar. 2009, 6 pages.

Traggiai et al., "An efficient method to make human monoclonal antibodies from memory B cells: potent neutralization of SARS coronavirus," Nat Med, 10:871-875, Aug. 2004, 5 pages.

Turner et al., "Roles of amyloid precursor protein and its fragments in regulating neural activity, plasticity and memory," Prog Neurobiol 70(1):1-32, 2003, 32 pages.

Ueda et al., "Molecular cloning of cDNA encoding an unrecognized component of amyloid in Alzheimer's disease," Proc Natl Acad Sci, 90:11282-11286, Dec. 1993, 5 pages.

United States Office Action in U.S. Appl. No. 12/522,031, dated Dec. 10, 2012, 20 pages.

United States Office Action in U.S. Appl. No. 12/522,031, dated Jun. 26, 2013, 6 pages.

United States Office Action in U.S. Appl. No. 13/003,245, dated Apr. 23, 2013, 13 pages.

United States Office Action in U.S. Appl. No. 13/003,245, dated Aug. 28, 2012, 33 pages.

United States Office Action Summary in U.S. Appl. No. 12/522,031, dated May 23, 2012, 10.

U.S. Appl. No. 09/724,319, filed Nov. 27, 2012, 111 pages.

Vajdos et al., "Comprehensive Functional Maps of the Antigen-binding Site of an Anti-ErbB2 Antibody Obtained with Shotgun Scanning Mutagenesis," J Mol Biol 320:415-428, 2002, 14 pages.

Van Der Putten et al., "Neuropathology in Mice Expressing Human a-Synuclein," J Neurosci, 20(16):6021-6029, Aug. 2000, 9 pages.

Van Praag et al., "Functional neurogenesis in the adult hippocampus," Nature 415:1030-1034, Feb. 2002, 5 pages.

Wall, RJ, "Transgenic livestock: Progress and prospects for the future," Theriogenology 45:57-68 (1996).

Wang et al., "A subpopulation of precursor cells in the mouse dentate gyrus receives synaptic GABAergic input," Mol Cell Neurosci, 29:181-189, Jun. 2005, 9 pages.

Wang et al., "Clearance of amyloid-beta in Alzheimer's disease: progress, problems and perspectives," Drug Disc. Today, 11 (19-20):931-938, Oct. 2006, 9 pages.

Wang et al., "Functional soluble CD1 OO/Sema4D released from activated lymphocytes: possible role in normal and pathologic immune responses," Blood, 97(11):3498-3504, Jun. 2001, 7 pages.

(56) References Cited

OTHER PUBLICATIONS

Watanabe et al., "Enhanced Immune Responses in Transgenic Mice Expressing a Truncated Form of the Lymphocyte Semaphorin CD100," J Immunol, 167(8):4321-4328, Oct. 2001, 9 pages.
Waxman and Giasson, "Characterization of antibodies that selectively detect a-synuclein in pathological inclusions," Acta Neuropathol, 116(1):37-46, Jul. 2008, 17 pages.
Weksler et al., "Patients with Alzheimer disease have lower levels of serum anti-amyloid peptide antibodies than healthy elderly individuals," Experimental Gerontology, 37:43-948, 2002, 8 pages.
Wilcock et al., "Amyloid-β vaccination, but Not Nitro-Nonsteroidal Anti-Inflammatory Drug Treatment, Increases Vascular Amyloid and Microhemorrhage While Both Reduce Parenchymal Amyloid," Neuroscience 144:950-960, Feb. 2007, 11 pages.
Wilcock et al., "Intracranially Administered Anti-A13 Antibodies Reduce β-Amyloid Deposition by Mechanisms Both Independent of and Associated with Microglial Activation," J Neurosci, 23(9):3745-3751, May 2003, 7 pages.
Wilcock et al., "Passive immunotherapy against Aβ in aged APP= transgenic mice reverses cognitive deficits and depletes parenchymal amyloid deposits in spite of increased vascular amyloid and microhemorrhate," J Neuroinfmallation, 1:24, Dec. 8, 2004, 11 pages.
Wilcock et al., "Quantification of cerebral amyloid angiopathy and parenchymal amyloid plaques with Congo red histochemical stain," Nat Protoc 1(3):1591-1595, 2006, 5 pages.
Wittnam et al., "Pyroglutamate amyloid β (Aβ) aggravates behavioral deficits in transgenic amyloid mouse model for Alzheimer disease," J Biol Chem, 287(11):8154-8162, Mar. 9, 2012, 15 pages.
Woulfe et al., "Absence of elevated anti-a-synuclein and anti-EBV latent membrane protein antibodies in PD," Neurology, 58: 1435-1436, May 2002, 4 pages.
Wu et al., "Humanization of a Murine Monoclonal Antibody by Simultaneous Optimization of Framework and CDR Residues," J Mol Biol 294:151-162, 1999, 12 pages.
Zhang et al., "Semi-quantitative analysis of a-synuclein in subcellular pools of rat brain neurons: An immunogold electron microscopic study using a C-terminal specific monoclonal antibody," Brain Res, 1244:40-52, 2008, 13 pages.
Zhao et al., "Distinct Morphological Stages of Dentate Granule Neuron Maturation in the Adult Mouse Hippocampus," J Neurosci. 26(1):3-11, Society for Neuroscience, Jan. 2006, 9 pages.
Neff et al., "Immunotherapy and naturally occurring autoantibodies in neurodegenerative disorders," Autoimmunity Reviews, 7:501-507, Jun. 2008, 7 pages.
O'Nuallain et al., "Conformational Abs recognizing a generic amyloid fibril epitope," Proceedings Nationa Academy of Sciences, 99(3):1485-1490, Feb. 2002.

Orgogozo et al., "Subacute meningoencephalitis in a subset of patients with AD after Aβ 42 immunization," Neurology, 61 (1 ):46-54, Jul. 2003, 11 pages.
Padlan et al., "Structure of an antibody-antigen complex: Crystal structure of the HyHEL-10 Fab-lysozyme complex," Proc Natl Acad Sci USA, 86(15):5938-5942, Aug. 1989, 5 pages.
Palop et al., "Aberrant Excitatory Neuronal Activity and Compensatory Remodeling of Inhibitory Hippocampal Circuits in Mouse Models of Alzheimer's Disease," Neuron 55(5):697-711, Cell Press, Sep. 2007, 15 pages.
Pang, "Mass Spectrometry-Based Structural Probing of Amyloid β-Protein," http://gradworks.umi.com/34/97/3497449.html, 202 pages.
Papachroni et al., "Autoantibodies to alpha-synuclein in inherited Parkinson's disease," J Neurochem, 101 :749-756, May 2007, 8 pages.
Patrias et al., "Specific antibodies to soluble alpha-synuclein conformations in intravenous immunoglobulin preparations," Clin. Exp. Immunol., 161 :527-535, Sep. 2010, 9 pages.
Paul, Editor, Fundamental Immunology, Third Edition, Raven Press, New York, pp. 292-295, 1993, 6 pages.
Perrin et al., "Epitope mapping and specificity of the anti-a-synuclein monoclonal antibody Syn-1 in mouse brain and cultured cell lines," Neurosci. Lett., 349(2):133-135, 2003, 3 pages.
Peters and Kaiserman-Abramof, "The Small Pyramidal Neuron of the Rat Cerebral Cortex. The Perikaryon, Dendrites and Spines," Am J Anat, 127:321-356, 1970, 35 pages.
Pfeifer et al., "Cerebral Hemorrhage After Passive Anti-Aβ Immunotherapy," Science, 298:1379, 2002, 3 pages.
Piantadosi et al., "Abstracts from the Program of the Second Annual Meeting of the American Society for Experimental Neurotherapeutics, Washington, DC, Mar. 23-25, 2000." American Society for Experimental Neurotherapeutics Abstracts, Arch Neurol., 57:1233-1239 (2000).
Plant et al., "The production ofamyloid beta peptide is a critical requirement for the viability of central neurons," J Neurosci, 23(13):5531-5535, Society for Neuroscience, Jul. 2003, 5 pages.
Plümpe et al., "Variability of doublecortin-associated dendrite maturation in adult hippocampal neurogenesis is independent of the regulation of precursor cell proliferation," BMC Neurosci, 7:77, Nov. 2006, 14 pages.
Portelius et al., "Characterization of Amyloid β Peptides in Cerebrospinal Fluid by an Automated Immunoprecipitation Procedure Followed by Mass Spectrometry," J Proteome Res, 6(11):4433-4439, Nov. 1, 2007, 7 pages.
Portelius et al., "Determination of β-Amyloid Peptide Signatures in Cerebrospinal Fluid Using Immunoprecipitation-Mass Spectrometry," J Proteome Res, 5(4):1535-3893, Apr. 1, 2006, 7 pages.
Priller et al., "Synapse Formation and Function Is Modulated by the Amyloid PrecursorProtein," J Neurosci, 26(27):7212-7221, Jul. 2006, 10 pages.
Qui et al., "Small antibody mimetics comprising two complementarity-determining regiions and a framework region for tumor targeting," Nature Biotech 25:921-929, Aug. 2007, 9 pages.

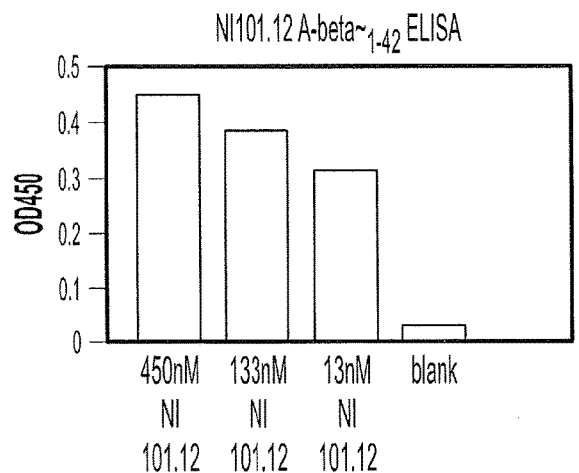
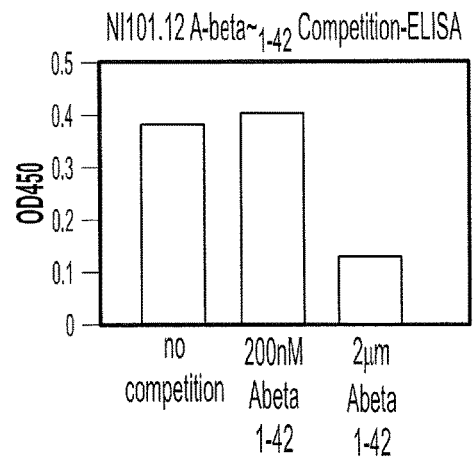
FIG. 14A  FIG. 14B
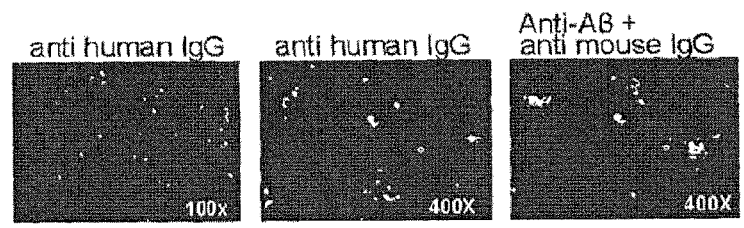
FIG. 15

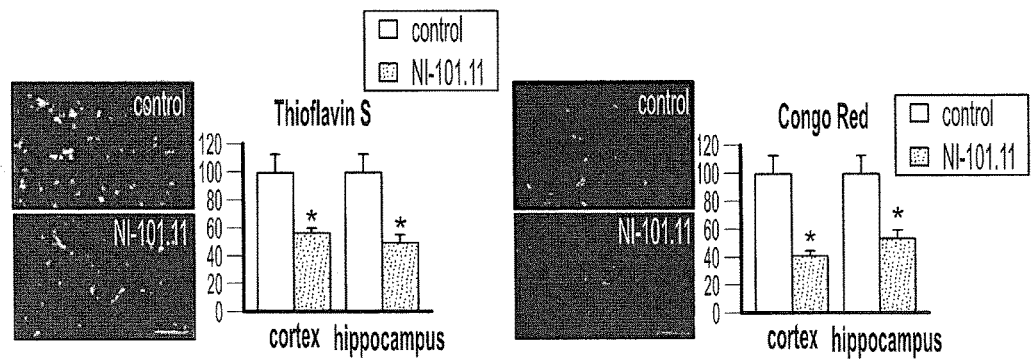
FIG. 18A  FIG. 18B
FIG. 18C  FIG. 18D  FIG. 18E
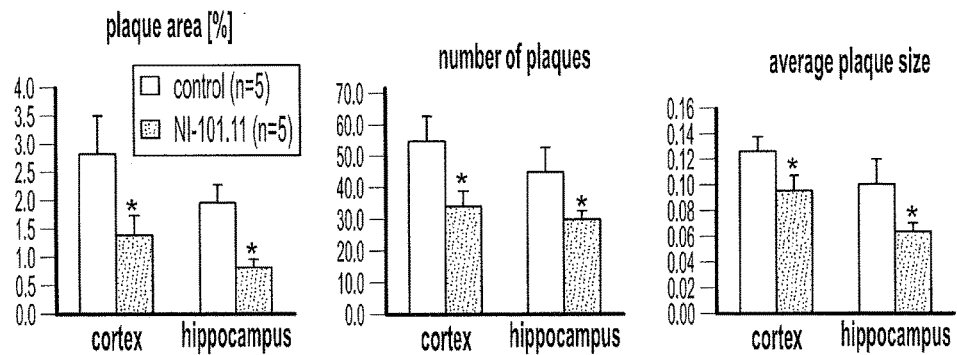
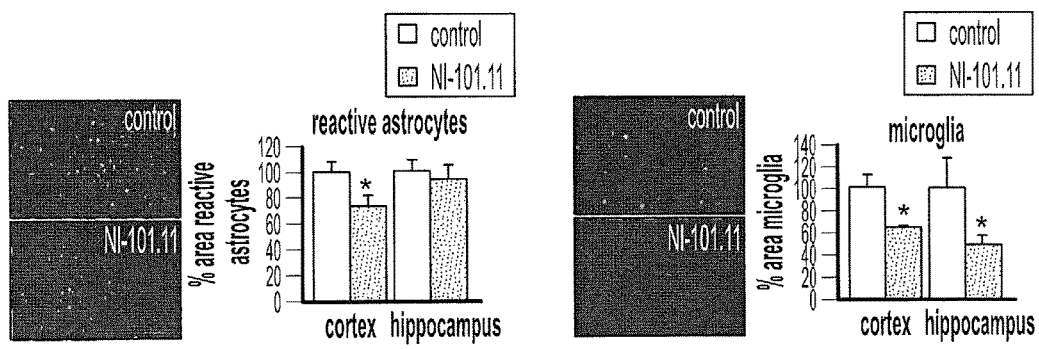
FIG. 19A  FIG. 19B

METHODS OF TREATING ALZHEIMER'S DISEASE

CROSS-REFERENCE TO RELATED APPLICATIONS

This application is a divisional of U.S. patent application Ser. No. 15/066,304, filed on Mar. 10, 2016 (now U.S. Pat. No. 9,828,420), which is a divisional of U.S. patent application Ser. No. 14/322,096, filed on Jul. 2, 2014 (abandoned), which is a divisional of U.S. patent application Ser. No. 12/522,031, filed on Mar. 1, 2010 (now U.S. Pat. No. 8,906,367), which is the U.S. National Stage of International Application No. PCT/EP2008/000053, filed on Jan. 7, 2008, which claims the benefit of U.S. Provisional Application No. 60/934,291, filed on Jun. 11, 2007, U.S. Provisional Application No. 60/878,831, filed on Jan. 5, 2007, EP Application No. 07020341.9, filed on Oct. 17, 2007, and EP Application No. 07000211.8, filed on Jan. 5, 2007. The contents of each of these applications are incorporated herein by reference in their entirety.

FIELD OF THE INVENTION

The present invention relates to novel specific binding molecules, particularly human antibodies as well as fragments, derivatives and variants thereof that recognize disease-associated epitopes, including neoepitopes, of proteins which derive from native endogenous proteins, and which are prevalent in the body of a patient in a variant form and/or out of their normal physiological context. In addition, the present invention relates to pharmaceutical compositions comprising such binding molecules, antibodies and mimics thereof, and to methods of screening for novel binding molecules, which may or may not be antibodies, targets and drugs in the treatment of various disorders, in particular neurological disorders such as Alzheimer's disease, amyloidoses and beta-amyloid pathology.

BACKGROUND OF THE INVENTION

The success in generating monoclonal antibodies rests on the efficient and selective fusion of antigen-stimulated B cells with a murine myeloma cell line followed by selection of stable antibody producing hybrids as originally described by Köhler and Milstein, Nature 256 (1975), 495-497. However, the therapeutic utility of murine based antibodies in human is hampered by the human anti-mouse antibody (HAMA) response in view of their non-human origin. Approaches for making human or human-like monoclonal antibodies became available through genetic engineering. However, the methods hitherto available suffer from the drawback that they are not suitable to produce antibodies with the characteristics of those produced in the course of a physiological human immune response. Furthermore, such antibodies may not be specific enough because of cross-reactivity with other proteins and/or the target protein in context with normal physiological function. In case of Alzheimer's or Parkinson's disease, for example, antibodies that also cross-react with high affinity with physiological derivatives of amyloid precursor protein (APP) or alpha synuclein are considered to exhibit side effects related to the normal functions of the physiologic target structures. In this respect, an undesired autoimmune disease would downrightly be induced—a hardly calculable risk in the conceptual design of active immunization experiments employing protein structures that, in variant form, also occur physiologically. Side effects not related to the target structure are, for example, anaphylactic reactions, as are to be expected as undesired and dreaded side effects of the systemic administration of exogenous proteins. According to recent findings, this can also be the case in so-called humanized antibodies, which originally stem from non-human organisms, usually from mice. On the other hand, active immunization with pathological relevant antigens bears the considerable risk of patients developing antibodies and T cell responses which also recognize physiological variants of such proteins and in consequence lead to a dangerous and uncontrollable autoimmune response.

Thus, there is a need of providing agents which are specific for a target involved in a disorder and which are tolerated by the human body.

SUMMARY OF THE INVENTION

An object of the present invention is a method for identifying, validating and producing diagnostically and therapeutically useful binding molecules, in particular antibodies that are directed against pathologic variants of endogenous proteins. More specifically, the present invention relates to a method of isolating a disease-associated protein-specific binding molecule comprising:

(a) subjecting a sample obtained from a patient who is symptom-free, or who is clinically unusually stable, but who is affected with or at risk of developing a disorder to a specimen of pathologically altered cells or tissues with predetermined pathological characteristics; and (b) identifying and optionally isolating a binding molecule which binds to said specimen but not to corresponding cells or tissues without such pathological characteristics as it may be derived from a healthy subject.

Known is the fact that, in case of autoimmune diseases, antibodies are directed against autologous cells and proteins or other compounds such as glycolipids expressed by said cells while evading the known tolerance mechanisms. Also known is the fact that, in case of endogenous neoplastic developments, a cellular and humoral immunity to the neoplastic cells can develop and can thus effect an endogenous immunological protection mechanism against neoplastic tissue degeneration.

The present invention makes use of the surprising finding that antibodies can also be directed against pathophysiologically relevant variants of endogenous proteins, in particular against neoepitopes, which are formed due to pathologically altered transcription, translation, or post-transcriptional or post-translational modification, or proteolytic processing, or aggregation. Such antibodies are directed against endogenous proteins which, owing to their new structure that deviates from the normal physiology, become pathophysiologically relevant by means of developing pathological effects. For reasons of immune tolerance, the antibodies connected with the corresponding immune response to neoepitopes in such pathological variants do not normally exhibit any cross reactions against the physiologically functional proteins, however, as opposed to the case of autoimmune diseases. This is because the formation of potentially cross-reactive antibodies is specifically suppressed by the known tolerance mechanisms, whereas the development of an immune response to pathological neoepitopes can escape tolerance.

Hence, the present invention relates to a novel approach of identifying diagnostically, therapeutically, and preventively active binding molecules, especially antibodies and antibody fragments from clinically preselected human subjects by means of interaction with identifiable pathological structures.

The present invention is thus directed to antibodies or antigen-binding fragments and similar antigen binding molecules which are capable of recognizing epitopes, including neoepitopes, of disease-associated proteins which derive from native endogenous proteins and are prevalent in the body of a patient in a variant form, e.g. as a pathological protein and/or out of their normal physiological context. Furthermore, the present invention relates to compositions comprising said antibodies and to immunotherapeutic and immunodiagnostic methods using the same.

Furthermore, in antibody identification, the method according to the present invention can do without previous hypothesis on the identity of its molecular target structure, solely by means of its association with pathologically relevant structures. Besides the possibility of thus identifying molecular target structures hitherto unknown for specific diseases, a further advantage of antibodies that are exclusively directed against pathological structures is based on the fact that their pharmacodynamic availability is not negatively influenced by binding to non-diseased tissues in such a way that the antibody is buffered with respect to its concentration and sink effects thus hampering the determination of therapeutically effective concentrations. Furthermore, the antibody and binding molecules of the present invention are preferably characterized in that they react with the variant form of the disease-associated protein in vivo or with a cell or cell membrane, and on a section of the pathologically characterized diseased tissue, respectively, but not or to a significantly lesser extent with the physiological variant of the cognate protein; see also, e.g., Example 2.

Since the present invention enables identifying and isolating molecular target structures in diseased cells and tissues, a further embodiment concerns the antigen and pathological protein, i.e. disease-associated protein, respectively, which is bound by the neoepitope-specific antibody of the present invention.

A particularly preferred embodiment is a human antibody or antigen-binding fragment thereof which demonstrates the immunological binding characteristics of any of the antibody characterized by the variable regions $V_H$ and/or $V_L$ as set forth in Tables 2 and 3, infra. Alternatively, the antibody is a humanized, xenogeneic, or a chimeric human-murine antibody, the latter being particularly useful for diagnostic methods and studies in animals. Therapeutic compositions including the antibody or active fragments thereof, or agonists and cognate molecules, or alternately, antagonists of the same, and methods of use of such compositions in the prevention, diagnosis or treatment of a disease using these compositions are also included, wherein an effective amount of the composition is administered to a patient in need of such treatment.

The antigen-binding fragment of the antibody can be a single chain Fv fragment, an F(ab') fragment, an F(ab) fragment, and an F(ab')$_2$ fragment, or any other antigen-binding fragment. In a specific embodiment, infra, the antibody or fragment thereof is a human IgG isotype antibody.

Naturally, the present invention extends to the immortalized human B memory lymphocyte and B cell, respectively, that produces the antibody having the distinct and unique characteristics as defined below.

The present invention also relates to polynucleotides encoding at least a variable region of an immunoglobulin chain of the antibody of the invention. Preferably, said variable region comprises at least one complementarity determining region (CDR) of the $V_H$ and/or $V_L$ of the variable region as set forth in Tables 2 and 3, infra. A corresponding set of CDRs is given in Table 4, infra.

Accordingly, the present invention also encompasses vectors comprising said polynucleotides and host cells transformed therewith as well as their use for the production of an antibody and equivalent binding molecules which are specific for neoepitopes that are indicative and/or causative for a disorder, in particular for a disorder of the brain such as Alzheimer's disease and Parkinson disease.

The antibody, immunoglobulin chain(s), binding fragments thereof and antigen binding to said antibody can be used in pharmaceutical and diagnostic compositions for immunotherapy and diagnosis, respectively. The use of the foregoing compositions in the preparation of a medicament is however preferred.

Hence, it is a particular object of the present invention to provide methods for treating or preventing a neurological disorder characterized by abnormal accumulation and/or deposition of a protein in the central nervous system without interfering with the natural function of the respective protein. The methods comprise administering an effective concentration of an antibody or antibody derivative to the subject where the antibody binds to the pathological form of the protein or the protein deposit with a substantially higher affinity than to the normal physiological form of the protein. In a preferred embodiment, the present invention provides methods for treating or preventing or slowing the onset of diseases associated with the accumulation and deposition of the amyloid beta peptide in a subject, such as Alzheimer's disease, Down's syndrome, mild cognitive impairment, cerebral amyloid angiopathy, vascular dementia, multi-infarct dementia. The methods comprise administering an effective concentration of an antibody or antibody derivative to the subject where the antibody binds to the pathological form of the protein or the protein deposit with higher affinity than to the normal physiological form of the protein. Similar therapeutic approaches are envisaged for the treatment of Parkinson's disease, Huntington's disease, Creutzfeldt-Jakob disease, cystic fibrosis, Gaucher's disease and the like.

Further embodiments of the present invention will be apparent from the description that follows.

BRIEF DESCRIPTION OF THE DRAWINGS

FIG. 14A: shows the binding of recombinant NI-101.12 to synthetic Abeta1-42 peptide via ELISA. FIG. 14B: shows NI-101.12 binding was competed by excess Abeta1-42 peptide.

FIG. 15: Recombinant human NI-101.11 antibody against brain beta-amyloid crosses the blood brain barrier in a transgenic mouse model of Alzheimer's disease, and binds to brain beta-amyloid plaques in vivo.

FIG. 18A: shows that passive immunization with NI-101.11 reduces beta-amyloid load in arcAbeta mice. Thioflavin S plaque load analyses reveal significant reductions of more than 50% compared to the control antibody treated animals (Mann-Whitney U; $p=0.02$ for cortex, $p=0.009$ for hippocampus for ThioS). Scale bar: 200 µm. FIG. 18B: shows that passive immunization with NI-101.11 reduces beta-amyloid load in arcAbeta mice. Congo Red plaque load analyses reveal significant reductions of more than 50% compared to the control antibody treated animals (Mann-Whitney U; $p=0.009$ for cortex and $p=0.04$ for hippocampus for Congo Red analysis). Scale bar: 200 µm. FIG. 18C: shows that Thioflavin S analysis reveals a significant reduction in beta-amyloid burden in NI-101.11 treated arcAbeta mice compared to control treated animals. FIG. 18D: shows that Thioflavin S analysis reveals a significant reduction in number of beta-amyloid plaques in NI-101.11 treated arcAbeta mice compared to control treated animals. FIG. 18E: shows that Thioflavin S analysis reveals a significant reduction in average plaque size in NI-101.11 treated arcAbeta mice compared to control treated animals. Mann-Whitney U statistics: p=0.02 for plaque area cortex; p=0.009 for plaque area hippocampus; p=0.047 for plaque number cortex; p=0.047 for plaque number hippocampus; p=0.009 for plaque size cortex; p=0.009 for plaque number hippocampus.

FIG. 19A: shows anti-GFAP staining in the cortex of NI-101.11 treated arcAbeta mice compared to control treated transgenics. Scale bar: 200 µm. Quantification of anti-GFAP staining revealed a significant reduction in the number of reactive astrocytes in the cortex of NI-101.11 treated arcAbeta mice when compared to control treated transgenics. FIG. 19B: shows Iba-1 staining in NI-101.11 treated mice in cortex and hippocampus. Quantification of Iba-1 staining showed a trend towards a reduced number of activated microglia in NI-101.11 treated mice in cortex and hippocampus. Scale bar: 200 µm. Thus, reduced beta-amyloid load is accompanied by decreased astrocytosis and microgliosis.

DETAILED DESCRIPTION OF THE INVENTION

I. Definitions

Figure 1A:
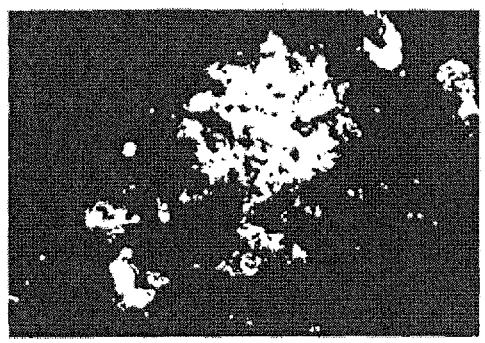
FIG. 1A: provides the results of immunohistochemical staining with human antibodies against beta-amyloid. Clinically unusually stable patients with Alzheimer's disease contain antibodies to beta-amyloid plaques. Immunohistochemical staining with antibodies from clinically unusually stable patients on brain sections obtained from patients with pathologically confirmed Alzheimer's disease reveals antibodies that bind to beta-amyloid plaques confirmed by a known antibody against human beta-amyloid.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non-naturally occurring Non-naturally occurring variants may be produced using art-known mutagenesis techniques. Variant polypeptides may comprise conservative or non-conservative amino acid substitutions, deletions or additions.

Derivatives of neoepitope-specific binding molecules, e.g., antibodies and antibody polypeptides of the present invention, are polypeptides which have been altered so as to exhibit additional features not found on the native polypeptide. Examples include fusion proteins. Variant polypeptides may also be referred to herein as "polypeptide analogs." As used herein a "derivative" of a binding molecule or fragment thereof, an antibody, or an antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refer to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

Unless stated otherwise, the terms "disorder" and "disease" are used interchangeably herein. A "binding molecule" as used in the context of the present invention relates primarily to antibodies, and fragments thereof, but may also refer to other non-antibody molecules that bind to a neoepitope including but not limited to hormones, receptors, ligands, major histocompatibility complex (MHC) molecules, chaperones such as heat shock proteins (HSPs) as well as cell-cell adhesion molecules such as members of the cadherin, intergrin, C-type lectin and immunoglobulin (Ig) superfamilies. Thus, for the sake of clarity only and without restricting the scope of the present invention most of the following embodiments are discussed with respect to antibodies and antibody-like molecules which represent the preferred binding molecules for the development of therapeutic and diagnostic agents.

The terms "antibody" and "immunoglobulin" are used interchangeably herein. An antibody or immunoglobulin is an antigen-binding molecule which comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. Any antibody or immunoglobulin fragment which contains sufficient structure to specifically bind to an antigen is denoted herein interchangeably as an "antigen binding fragment" or an "immunospecific fragment."

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a n-sheet conformation and the CDRs form loops which connect, and in some cases form part of, the n-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, *J. Mol. Biol.,* 196:901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

| CDR Definitions[1] | | |
|---|---|---|
| | Kabat | Chothia |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system.

Antibodies or antigen-binding fragments, immunospecific fragments, variants, or derivatives thereof of the invention include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity.

Antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. Antibodies or immunospecific fragments thereof of the present invention may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks). As used herein, "human" antibodies include antibodies having the amino acid sequence of a human immunoglobulin and include antibodies isolated from human patients, human immunoglobulin libraries or from animals transgenic for one or more human immunoglobulins and that do not express endogenous immunoglobulins, as described infra and, for example in, U.S. Pat. No. 5,939,598 by Kucherlapati et al. A human antibody is still "human" even if amino acid substitutions are made in the antibody, e.g., to improve binding characteristics.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a VL or CL domain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, peptide or polypeptide epitope recognized by antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of Aβ.

The term "neoepitope" in accordance with the present invention denotes an epitope which is unique for a disease pattern and contained in or formed by a disorder-associated protein which is a pathological variant from an otherwise non-pathological protein and/or deviating from the physiology of the healthy state. Said pathophysiological variants can be formed by means of pathologically altered transcription, pathologically altered translation, post-translational modification, pathologically altered proteolytic processing, pathologically altered complex formation with physiological or pathophysiological interaction partners or cellular structures in the sense of an altered co-localization, or pathologically altered structural conformation—like for example aggregation, oligomerization or fibrillation—whose three- or four-dimensional structure differs from the structure of the physiologically active molecule. Moreover, a pathophysiological variant can also be characterized in that it is not located in its usual physiological environment or sub-cellular compartment. As an example, neoepitopes may be located in the pathologically conspicuous structures in the areas of brain tissues that obviously experience or have already experienced functional damage. Whether a given structure, for example cell or tissue, or protein displays a neoepitope can be verified by reversing the method described below for isolating and characterizing a disorder-associated protein specific binding molecule in that a binding molecule, for example antibody identified by said method is used to screen a sample for binding to the antibody, thereby determining the presence of a neoepitope.

The phrases "disease-associated protein specific" and "neoepitope specific" are used interchangeably herein with the term "specifically recognizing a neoepitope". As used herein terms such as "absence of cross-reactivity", "specific," "specifically recognizing," "specifically binding," "preferentially binding," and the like refer to the binding molecule's ability to discriminate between the neoepitope of a disorder-associated protein and the native protein in its wild type form and natural context. Thus, the binding molecule of the present invention has a preferential binding affinity to the neoepitope over the native protein antigen by a factor of at least two, preferably at least 5, usually more than by a factor of 10, particularly preferred by a factor of 50 and even more preferred higher than 100. Furthermore, the relative $K_D$ of the binding molecule, e.g., antibody for the specific target epitope, e.g. neoepitope is preferably at least 10-fold less, more preferably at least 100-fold less or more than the $K_D$ for binding that antibody to other ligands or to the native counterpart of the disease-associated protein.

By "specifically binds," or "specifically recognizes," used interchangeably herein, it is generally meant that a binding molecule, e.g., an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, a binding molecule, e.g., an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

A binding molecule, e.g., an antibody or antigen-binding fragment, variant, or derivative disclosed herein may be said to bind a target polypeptide disclosed herein or a fragment or variant thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. More preferably, an antibody of the invention may be said to bind a target polypeptide disclosed herein or a fragment or variant thereof with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

A binding molecule, e.g., an antibody or antigen-binding fragment, variant, or derivative disclosed herein may be said to bind a target polypeptide disclosed herein or a fragment or variant thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. More preferably, an antibody of the invention may be said to bind a target polypeptide disclosed herein or a fragment or variant thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$M$^{-1}$ sec$^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Binding molecules, e.g., antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof of the invention may also be described or specified in terms of their binding affinity to a polypeptide of the invention. Preferred binding affinities include those with a dissociation constant or Kd less than $5 \times 10^{-2}$M, $10^{-2}$M, $5 \times 10^{-3}$M, $10^{-3}$M, $5 \times 10^{-4}$ M, $10^{-4}$M, $5 \times 10^{-5}$M, $10^{-5}$M, $5 \times 10^{-6}$ M, $10^{-6}$ M, $5 \times 10^{-7}$M, $10^{-7}$M, $5 \times 10^{-8}$ M, $10^{-8}$ M, $5 \times 10^{-9}$M, $10^{-9}$M, $5 \times 10^{-10}$ M, $10^{-10}$ M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, or $10^{-15}$M.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit. The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., *J. Immunol.* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "properly folded polypeptide" includes polypeptides in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

By "subject" or "individual" or "animal" or "patient" or "mammal," is meant any subject, particularly a mammalian subject, e.g., a human patient, for whom diagnosis, prognosis, prevention, or therapy is desired.

II. Methods to Identify Binding Molecules

The present invention generally relates to means and methods for discovering therapeutically efficient antibodies from clinically preselected human subjects. As demonstrated in the examples, human antibodies against abnormal structures in human brain diseases can be isolated from phenotypically healthy, or clinically unusually stable patients and corresponding recombinant antibodies can be successfully used for the treatment, amelioration of pathology and prevention of impairment of brain function without substantial side effects. Clinical stability or non-progression of disease can be identified by way of example by measurement over time of clinical, e.g., cognitive, status (by neuropsychological testing, for example); assessment of the global functional level; evaluation of the daily living capacities or behavioral deficits; volumetric analysis of brain structures; in vivo measurement of pathological deposits of abnormal proteins in brain (e.g. PET beta-amyloid imaging) or biochemical variables in body fluids (e.g. tau proteins, or Abeta peptides); and by comparison to the natural course/history of the disease. Thus, the present invention provides antibodies and binding molecules which are capable of recognizing neoepitopes of disease-associated proteins which derive from native endogenous proteins, and are prevalent in the body of a patient in a variant form, e.g. as a pathological protein and/or out of their normal physiological context. In particular, antibodies and antigen-binding fragments thereof are provided, which demonstrate the immunological binding characteristics and/or biological properties as outlined for the antibody illustrated in the Examples. Where present, the term "immunological binding characteristics," or other binding characteristics of an antibody with an antigen, in all of its grammatical forms, refers to the specificity, affinity, cross-reactivity, and other binding characteristics of an antibody. Naturally, the present invention extends to the antibody producing cell lines and recombinant cells as well. The present invention further relates to diagnostic assays and kits that comprise the binding molecule of the present invention and to therapeutic methods and therapeutic evaluations based thereon.

The present invention is based on the observation that in human subjects and patients preselected according to specific clinical criteria, who bear a risk of developing a neurological disorder like Alzheimer's disease due to their age, as related to the humoral defense, antibodies to endogenous pathophysiological variants like Abeta peptide aggregates, neurofibrillary tangles, dystrophic neurites and further cellular structures can also be found, which are neuropathologically characteristic for the disorder. These structures can be found alone or in combination with other pathological structures and can, as in case of the Abeta aggregates and the precursors of the neurofibrillary tangles, develop pathological effects. However, those antibodies specifically recognizing said structures exhibit no or significantly lower cross-reactivity to the normal physiologically functional forms of the proteins underlying the pathological structures, contrary to the known case of an autoimmune response.

Without intending to be bound by theory it is, based on the experiments performed in accordance with the present invention, believed that a disorder does not have to become manifest and phenotypically perceivable, as in case of an infection, in order to result in an experimentally measurable activity of the humoral immune system like the generation or activation of specific B cells or B memory cells. In case of tumor cells or differentiated cells, which have to be physiologically disposed of, mechanisms are already known, wherein partners like T4 helper cells and cytotoxic T cells and natural killer cells of the cellular immune system cooperate in the induction of apoptosis. It has to be assumed that, also in a healthy human, tumor cells or precursors thereof are formed on a daily basis by means of mutation.

However, these are immediately driven to apoptosis by means of humoral and cellular mechanisms, so that a tumor is not detectable. In this sense, a "healthy, or clinically unusually stable, patient" is not understood to denote an individual in whom no disease events take place, but an individual in whom the diverse disease events are controlled by blocking or defense mechanisms before they phenotypically manifest themselves.

In view of the above, it was hypothesized in accordance with the present invention that it should be possible to identify an antibody or an antibody-producing cell from specific patient collectives or healthy subjects, which have been preselected according to clinical criteria, without precognition of the molecular nature of a target structure epitope, e.g. neoepitope, wherein the antibody, in case of already prevailing tolerance in the donor organism—which is, for example, proved by the absence of autoimmunity—could successfully be employed against a disease in form of a recombinantly produced agent. Identifying such an antibody can thus be conducted without precognition of the molecular epitope of the target structure, but rather solely by means of binding to neoepitopes of pathologically conspicuous structures in clinico-pathologically well characterized tissue sections derived from human patients or from animal models of the respective disease.

Accordingly, in a first aspect the present invention relates to a method of isolating a disorder-associated protein-specific binding molecule comprising:

(a) subjecting a sample obtained from a patient who is symptom-free, or who is clinically unusually stable, but who is affected with or at risk of developing a disorder or effectively suppressing the manifestation or outbreak of a disorder to a specimen of pathologically or physiologically altered cells or tissue of predetermined clinical characteristics; and (b) identifying and optionally isolating a binding molecule which preferentially binds to said specimen but not or with significantly lower affinity to corresponding cells or tissues without such pathological characteristics as it may be derived from a healthy subject.

The method of the present invention can be performed as outlined in the Examples section with means well known to a person skilled in the art. For example, a liquid sample obtained from the patient can be passed through a first aperture of a duct which is in contact with the specimen target structure firmly held in an object holder, thereby allowing putative binding molecules present in the sample, either in a soluble form or expressed on the cell surface and membrane, respectively, to bind to said target structure. The liquid sample may contain for example lymphocytes and/or antibodies while the specimen may be a tissue section or a membrane coated with molecules or molecular combinations which are distinct for a pathological target structure.

Any non-binding matter can be removed via the second duct aperture. At the same time, the temperature of the object holder may be controlled by an object holder thermostat, for example at a temperature at which natural binding of the putative binding molecule to the neoepitope of the antigen specific for the specimen takes place in the human body. By way of the flowing motion, e.g. passing the liquid sample containing binding molecules, preferably at body temperature over the target structure natural systems of binding interactions can be simulated. However, other methods of incubating the sample with the specimen such as by means of a shaker or rotating table may be used as well. A particular advantage of the above-mentioned system is that it allows an interruption of metabolic processes at any time by decreasing the temperature of the object holder by means of the object holder thermostat. In doing so, the temperature of the object holder can be decreased to for example 2-10° C., in particular 4° C. A corresponding device that can be used in accordance with the method of the present invention is described in European patent application EP 1 069 431 A2. Hence, the method of the present invention will allow identification and characterization of the binding partners as well as at the same time to identify and characterize the molecular classes, molecular groups and/or molecular parts required for the binding process, i.e. the target structures of the specimen, which hitherto may be unknown. This will not only open up new possible ways of diagnosis, but will also provide a new test system for therapeutic approaches on a molecular level.

As a patient may qualify in accordance with the present invention a pool of healthy volunteers if specific surrogate markers predict a high probability of a status of a disease, which has surprisingly—and possibly due to a specific endogenous immune response—not become clinically manifest, however. In this sense, as related to diverse diseases, a healthy elderly human would be an individual, in which a neurodegenerative disease like Alzheimer's disease or Parkinson's disease is not yet clinically manifest, but in which the preclinical development of pathophysiological protein variants, i.e. disorder-associated proteins, and in the above-mentioned sense by means of early intervention of the humoral immune system with or without involvement of cellular components of the immune system, has been restricted or delayed to such an extent that, until the moment when the healthy, but not preclinical patient participated in the study, the clinical manifestation of the disease had not yet occurred. Preferably, inconspicuous volunteers in whom neither autoimmunological processes have been diagnosed nor other possible pathological conditions occur as side effects are recruited as donors for the sample in the first instance.

In principle samples from patients may be used, who have undergone an active immunization with variants of physiological proteins or peptides, wherein the antibody development has been boosted by the immunization. Antibodies, for example, can be identified and isolated from Alzheimer's disease patients that have been vaccinated with Abeta peptide. See for e.g., Hock et al., *Nature Medicine* 8:1280-1275 (2002), Hock et al., *Neuron* 38:547-554 (2003), and WO 2004/095031, each incorporated herein by reference in their entireties. However, it may be preferred to use samples from volunteers which have not received such immunization or corresponding medication concerning the disorder the variant pathological protein is associated with and/or causative of.

According to the present invention, samples of a patient, e.g. of individuals that have been clinically preselected are analyzed for the presence of binding molecules specifically recognizing specimen of pathologically conspicuous structures, for example in ex vivo tissue from clinico-pathologically characterized human patients or animal models like, for example, transgenic mice, or in vitro cell structures, or in pathological allogenic or xenogenic tissue. Preferably, said patient and/or as said subject providing the specimen are human, most preferably both.

The characteristic pathologically or physiologically altered sample, cell or tissue specimen is preferably displayed by optical detection after reaction with a binding molecule, e.g. antibody of the present invention. The specimen may be obtained as/from a cell sample, tissue section, cellular smear test, cell or tissue sample of an animal model of a human disease or in vitro cultured cell and tissue material. Preferably, at least one of said specimen is present in an object holder in form of a scan positions, wherein each scan position corresponds to a specific pathological structure and at least two of the scan positions are concomitantly exposed to detection of a reaction with the antibody. By way of example, antibodies to the neuropathological hallmarks of such neurodegenerative diseases as Alzheimer's disease, Parkinson's disease or tauopathies—including beta-amyloid plaques, Lewy bodies, neurofibrillary tangles and dystrophic neuritis can be detected on sections obtained from human post-mortem brain tissues with clinico-pathologically confirmed diagnoses of the respective disease entities. This is done by mounting small rods of paraffin embedded tissue on to glass slides which are then probed with samples of a patient or healthy donor. The detection of a reaction with the antibody is done following standard procedures of immunohistochemistry and microscopical scanning.

Multiple tissue microsections containing various human disease tissues can be assembled on the glass slide to form a multiple tissue microarray. Similarly, additional specimens from tissue samples of animal models of human disease, cellular smear or cells can be embedded in paraffin and mounted on glass slides alone or in combination with above described human post-mortem Alzheimer's disease brain tissue or tissue arrays. Thus, a single test position on the glass slide can comprise mixed arrays of tissue and other specimen displaying pathologically conspicuous structures.

In order to increase the throughput of the assay, more than one test position is mounted on a glass slide. Preferably, eight test positions are mounted onto glass slides in a two by four format fitting the 96 well or microtiter format. A more detailed description of this microtiter-compatible tissue microarray can be found infra in the supplementary methods section below.

As mentioned the sample to be analyzed may comprise a body fluid, a cell sample or the supernatant of a cell sample or a derivative thereof. Body fluids such as lumbar cerebrospinal fluid (CSF), plasma or urine can be collected following standard clinical procedures after informed consent of the patients. Most preferably, the sample comprises or is derived from B-cells or memory B-cells and/or comprises antibodies.

Preferably, said patient has been determined to be affected with a not yet manifested disorder or at risk to develop the disorder by the presence or absence of a surrogate marker, or by an unusually stable disease course. Clinical criteria are to be considered in connection with surrogate markers having either an increased probability of the occurrence or the manifestation of a disease according to the present invention in the sense of a preclinical condition, or, vice versa, proving the improbability of such a disease already having occurred as, for example, a genetic constellation promoting the disease is existent or an extreme exposition or way of living renders the phenotypical development of a disease probable. In the case of Alzheimer's disease this means that, according to the present invention, such human volunteers are searched for B cells or memory B cells against neuropathology-associated protein complexes like Abeta aggregates, oligomeric Abeta species and beta-amyloid fibrils in beta-amyloid plaques, for tau filaments in neurofibrillary tangles, for alpha synuclein in Lewy bodies or components hitherto not molecularly identified that, with respect to age, belong to a group of individuals in whom either the prevalence of Alzheimer's disease is particularly high or who originate genetically from a population bearing a high risk for Alzheimer's disease. These are, for example, persons older than 75 years having no or only marginal neuropsychologically measurable cognitive impairments, or in case of tumor indications, persons having highly indicative tumor markers, for example genetic tumor markers, but not suffering from the disease (Alloul et al., Arch. Gerontology Geriatrics 27 (1998), 189; Dunn et al., Immunity 21 (2004) 137-148). In case of mild cognitive impairment, these are patients that have remained clinically, neuropsychologically, or cognitively stable for years in spite of their annual statistical risk of more than 20% for developing a neurodegenerative disease that is clinically manifest and progressive in the further course. Thus, in one embodiment said surrogate marker is selected from the group consisting of old age, brain amyloid load, ApoE genotype, APP genotype, PS1 genotype, levels in body fluids of Abeta peptide, isoprostanes, Tau, and phospho-Tau.

A particular approach in employing the method according to the present invention is testing samples of B cells and B memory cells from clinically preselected volunteers against arrays of specimen of pathologically conspicuous tissues of entirely different or related primary diseases. In particular, such pathological tissues originate from human patients suffering from neurodegenerative diseases, protein-misfolding diseases, tissue amyloidoses and other diseases related to pathological deposits, autoimmune disorders, inflammatory diseases, hyperproliferative and neoplastic diseases, e.g., tumors, storage diseases and inclusion diseases as well as from animal models of human diseases, in particular from mice altered with pathologically relevant human genes.

In one particularly preferred embodiment, the present invention focuses on Alzheimer's disease. In this embodiment, the sample is obtained from a subject preferably fulfilling the following criteria:
 a) being 65, preferably 70 and more preferably 75 years of age or older;
 b) having full cognitive capacity and good health; and
 c) having no clinical signs of dementia; or
 d) having unusually slow rates of progression of disease despite the presence of an established clinical diagnosis of probable Alzheimer's disease; or
 e) having unusually low conversion rates from Mild Cognitive Impairment (MCI) to full blown Alzheimer's disease.

In a further embodiment, the method of the present invention further comprises the steps of:
 a) purifying B cells or B memory cells from a sample which has been identified to contain binding molecules, e.g. antibodies which preferentially bind to said specimen but not or with significantly lower affinity to corresponding cells or tissue of a healthy subject;
 b) obtaining the immunoglobulin gene repertoire encoding said antibodies from said B cells or B memory cells; and
 c) using said repertoire to express said antibodies, and optionally wherein step (b) comprises the steps of:
 d) obtaining mRNA from said B cells or memory B cells;
 e) obtaining cDNA from the mRNA of step (iv); and
 f) using a primer extension reaction to amplify from said cDNA the fragments corresponding to the heavy chains (HC) and the kappa/lambda light chains (LC) of said antibodies.

Methods of producing clones of an immortalized human B cell and B memory lymphocyte, comprising the step of transforming human B memory lymphocytes using Epstein Barr Virus (EBV) in the presence of a polyclonal B cell activator are summarized in international application WO2004/076677. This international application also describes methods for obtaining a nucleic acid sequence that encodes an antibody of interest, comprising the steps of preparing an immortalized B cell clone and obtaining/sequencing nucleic acid from the B cell clone that encodes the antibody of interest and further inserting the nucleic acid into or using the nucleic acid to prepare an expression host that can express the antibody of interest, culturing or subculturing the expression host under conditions where the antibody of interest is expressed and, optionally, purifying the antibody of interest. It goes without saying that the nucleic acid may be manipulated in between to introduce restriction sites, to change codon usage, and/or to add or optimize transcription and/or translation regulatory sequences. For example, nucleic acid sequences can be generated by back-translation of the polypeptide sequences of the present invention using software such as vector NTI software to generate nucleic acid sequences that are codon-optimized and optimized for RNA stability. All this techniques are state of the art and can be performed by the person skilled in the art without undue burden. Additional methods of immortalizing human B cells are well known in the art, e.g., the construction of human hybridomas or human-murine chimeric hybridomas.

In a further aspect, the present invention relates to a binding molecule which is capable of selectively recognizing an epitope of a disease-associated protein including a neoepitope of a disease-associated protein, which preferably can be obtained or validated by the method of the present invention described hereinbefore and illustrated in the examples. Advantageously, the binding molecule of the present invention does not substantially recognize said protein in its non-disorder-associated form; see also supra.

Means and methods for the recombinant production of binding molecules, in particular antibodies and mimics thereof as well as methods of screening for competing binding molecules, which may or may not be antibodies, are known in the art and are summarized, for example, in international application WO2006/103116 with respect to antibodies against beta-amyloid and the treatment/diagnosis of Alzheimer's disease, the disclosure content of which is incorporated herein by reference for this purpose of antibody engineering and administration for therapeutic or diagnostic applications.

However, as described herein, in particular with respect to therapeutic applications in human the antibody of the present invention is a human antibody. In this context, the variant pathological protein recognized by the antibody is preferably associated with a neurological disorder, preferably a disorder of the brain.

Moreover, as demonstrated in Examples 3 to 5 the binding molecule of the present invention, in particular an antibody has several advantageous biological properties one or more of which have been accomplished by the present invention for the first time, e.g. it is capable of:
 (i) crossing the blood brain barrier, for example at the site of the pathological event;
 (ii) binding beta-amyloid plaques, cerebrovascular amyloid, diffuse Abeta deposits, neurofibrillary tangles, hyperphosphorylated tau, alpha-synuclein positive Lewy-bodies or protein aggregates associated with dystrophic neurites;
 (iii) removing beta-amyloid plaques in the brain and/or preventing the formation of amyloid plaques in the brain;
 (iv) substantially restoring normal behavior; and/or
 (v) causing no microhemorrhages.

In a particular preferred embodiment, the antibody or equivalent binding molecule of the present invention may be distinguished from other antibodies by one or more of the following properties, e.g. they are able to:
 1. pass, at least in small amounts, the blood-brain barrier at the site of the pathological events;
 2. bind to one or more pathophysiologically relevant extracellular or cellular structure;
 3. lead to reduction of the pathophysiologically relevant structure in vitro or in vivo;
 4. lead to reduction of the pathophysiologically relevant structure and to the reduction of a toxicity associated therewith;
 5. lead to blocking or delaying a disease process;
 6. lead to regeneration of cellular and organ-specific and organismic functions and possibly to a secondary prevention of the recurrence of the original pathophysiology after degradation of the toxicity connected with the pathophysiologically relevant structure; and/or
 7. is not associated with increased microhemorrhages Furthermore, the absence of cross-reactivity with physiological precursors or derivatives leads to the consequence that, firstly, the concentrations are predictable as sink effects in healthy tissue structures are avoided and, secondly, that autoimmune responses in the sense of undesired side effects are substantially missing. In addition, previous reports suggested an association of cerebral amyloid angiopathy (CAA) with compromised vascular reactivity in a transgenic mouse model with CAA (Mueggler et al., J Neurosci 22 (2002), 7218-24.). The severe CAA occurring in old arcAβ mice (Knobloch et al., Neurobiol. Aging 28:1297-1306 (2007) epub Jul. 31, 2006) might thus constrain the vasodilative flexibility of affected blood vessels. In accordance with the present invention it is prudent to expect that treatment with the antibodies of the present invention can improve vasoreactivity and cerebral blood flow in aged APP transgenic mice. This may be validated by using the arcAβ mice model described in Knobloch et al. (2006), supra, and disclosed in US application "Transgenic animal model for Alzheimer's disease" by Grimm et al., Ser. No. 60/934,291 filed on Jun. 11, 2007, the disclosure content of which is incorporated herein by reference.

III. Antibodies

The present invention is further directed to the binding molecules e.g. antibodies and binding fragments, variants, and derivatives thereof shown in Table 2 and 3. The present invention is more specifically directed to an antibody, or antigen-binding fragment, variant or derivatives thereof, where the antibody specifically binds to the same neoepitope of a disorder-associated protein as a reference antibody selected from the group consisting of NI-101.10, NI-101.11, NI-101.12, NI-101.13, NI-101.12F6A, NI-101.13A, and NI-101.13B.

The invention is further drawn to an antibody, or antigen-binding fragment, variant or derivatives thereof, where the antibody competitively inhibits a reference antibody selected from the group consisting of NI-101.10, NI-101.11, NI-101.12, NI-101.13, NI-101.12F6A, NI-101.13A, and NI-101.13B from binding to the neoepitope of a disorder-associated protein.

The invention is also drawn to an antibody, or antigen-binding fragment, variant or derivatives thereof, where the antibody comprises an antigen binding domain identical to that of an antibody selected from the group consisting of NI-101.10, NI-101.11, NI-101.12, NI-101.13, NI-101.12F6A, NI-101.13A, and NI-101.13B.

The present invention further exemplifies several such binding molecules, e.g. antibodies and binding fragments thereof, which may be characterized by comprising in their variable region, e.g. binding domain at least one complementarity determining region (CDR) of the $V_H$ and/or $V_L$ variable region comprising any one of the amino acid sequences depicted in Table 2 ($V_H$) and Table 3 ($V_L$).

The corresponding nucleotide sequences encoding the above-identified variable regions are set forth in the attached sequence listing. An exemplary set of CDRs of the above amino acid sequences of the $V_H$ and/or $V_L$ region as depicted in Tables 2 and 3 are given in Table 4. However, as discussed in the following the person skilled in the art is well aware of the fact that in addition or alternatively CDRs may be used, which differ in their amino acid sequence from those set forth in Table 4 by one, two, three or even more amino acids in case of CDR2 and CDR3.

TABLE 2

Amino acid sequences of the $V_H$ region of neoepitope specific antibodies.

| Antibody | Variable heavy chain sequence |
| --- | --- |
| NI-101.10 | EVQLVQSGGGVVQPGRSLRLSCAASGFAFSSYGIHWVRQAPGKGLEWVAVIWFDGTKKY YTDSVKGRFTISRDNSKNTLYLQMNTLRAEDTAVYYCARDRGIGARRGPYYMDVWGKGTTVTVSS (SEQ ID NO: 4) |
| NI-101.11 | EVQLVQSGGGVVQPGRSLRLSCAASGFAFSSYGMHWVRQAPGKGLEWVAVIWFDGTKK YYTDSVKGRFTISRDNSKNTLYLQMNTLRAEDTAVYYCARDRGIGARRGPYYMDVWGKGT TVTVSS (SEQ ID NO: 6) |
| NI-101.12 | EVQLVESGPGLVKPAETLSLTCTVSGGSIRSGSICWYWIRQPPGKGLEWIGYFCYSGATFY TPSLRGRLTISVDASKNQLSLSLSSVTAADTAVYYCARRAGENSGGIEPYYGMDVWGQGT TVTVSS (SEQ ID NO: 10) |
| NI-101.13 | QVQLQESGPGLVKPSETLSLTCTVSGGSISRRSYYWGWIRQSPGKGLEWSGSIHYSGSTY YNPSLKSRVTISVDTSKNQFSLKLSSVTAADTAVYYCARSRWGSSWVFDYWGQGTLVTVSS (SEQ ID NO: 14) |
| NI-101.12F 6A | QVQLVESGGGVVQPGRSLRLSCAASGFAFSSYGMHWVRQAPGKGLEWVAVIWFDGTKK YYTDSVKGRFTISRDNSKNTLYLQMNTLRAEDTAVYYCARDRGIGARRGPYYMDVWGKGT TVTVSS (SEQ ID NO: 39) |
| NI-101.13A | QVQLQESGPGLVKPSETLSLTCTVSGGSISRRSYYWGWIRQSPGKGLEWSGSIHYSGSTYYNPSL KSRVTISVDTSKNQFSLKLSSVTAADTAVYYCARSRWGSSWVFDYWGQGTLVTVSS (SEQ ID NO: 42) |
| NI-101.13B | QVQLQESGPGLVKPSETLSLTCTVSGGSISRRSYYWGWIRQSPGKGLEWSGSIHYSGSTYYNPSL KSRVTISVDTSKNQFSLKLSSVTAADTAVYYCARSRWGSSWVFDYWGQGTLVTVSS (SEQ ID NO: 43) |

TABLE 3

Amino acid sequences of the $V_L$ region of neoepitope specific antibodies.

| Antibody | Variable light chain sequence (kappa or lambda) |
| --- | --- |
| NI-101.10 | EIVLTQSPSSLSASVGDRVTITCRASQSISSYLNWYQQKPGKAPKLLIYAASSLQSGVPSRF SGSGSGTDFTLTISSLQPEDFATYYCQQSYSTPLTFGGGTKLEIKR (SEQ ID NO: 8) |
| NI-101.11 | EIVLTQSPSSLSASVGDRVTITCRASQSISSYLNWYQQKPGKAPKLLIYAASSLQSGVPSRF SGSGSGTDFTLTISSLQPEDFATYYCQQSYSTPLTFGGGTKLEIKR (SEQ ID NO: 8) |
| NI-101.12 | DEIVLTQSPSSLSASIGDRVTITCRASESINKYVNWYQQKPGKAPKLLIYAASSLQSGAPSRV SGSGFGRDFSLTISGLQAEDFGAYFCQQSYSAPYTFGQGTKVEIKRT (SEQ ID NO: 12) |
| NI-101.13 | QSVLTQPPSASGTPGQRVTISCSGSSSNIGSNYVYWYQQPPGTAPKWYRNNQRPSGVP DRFSGSKSGTSASLAISGLRSEDEADYYCAAWDDSLSGYVFGTGTKVTVLG (SEQ ID NO: 16) |
| NI-101.12F 6A | DIQMTQSPSSLSASVGDRVTITCRASQSISSYLNWYQQKPGKAPKLLIYAASSLQSGVPSRF SGSGSGTDFTLTISSLQPEDFATYYCQQSYSTPLTFGGGTKVEIKR (SEQ ID NO: 41) |
| NI-101.13A | DIQLTQSPSSLSASVGDRVTITCRASQSISSYLNWYQQKPGKAPKLLIYAASSLQSGVPSRFSGSGS GTDFTLTISSLQPEDFATYYCQQSYSTRTFGQGTKVEIKR (SEQ ID NO: 44) |
| NI-101.13B | DIQLTQSPSTLSASVGDRVTITCRASQSISSWLAWYQQIPGKAPKWYKASSLESGVPSRFSGSGS GTEFTLTISSLQPDDFATYYCQQYNSYSRTFGQGTKLEIKR (SEQ ID NO: 45) |

TABLE 4

Denomination of CDR protein sequences in Kabat Nomenclature of $V_H$ and $V_L$ regions of neoepitope specific antibodies.

| Antibody | Variable heavy chain | Variable light chain |
|---|---|---|
| NI-101.10 | | |
| CDR1 | SYGIH (SEQ ID NO: 17) | RASQSISSYLN (SEQ ID NO: 23) |
| CDR2 | VIWFDGTKKYYTDSVKG (SEQ ID NO: 18) | AASSLQS (SEQ ID NO: 24) |
| CDR3 | DRGIGARRGPYYMDV (SEQ ID NO: 19) | QQSYSTPLT (SEQ ID NO: 25) |
| NI-101.11 | | |
| CDR1 | SYGMH (SEQ ID NO: 20) | RASQSISSYLN (SEQ ID NO: 23) |
| CDR2 | VIWFDGTKKYYTDSVKG (SEQ ID NO: 21) | AASSLQS (SEQ ID NO: 24) |
| CDR3 | DRGIGARRGPYYMDV (SEQ ID NO: 22) | QQSYSTPLT (SEQ ID NO: 25) |
| NI-101.12 | | |
| CDR1 | SGSIC (SEQ ID NO: 26) | RASESINKYVN (SEQ ID NO: 29) |
| CDR2 | WIGYFCYSGATFYTPSLRG (SEQ ID NO: 27) | AASSLQS (SEQ ID NO: 30) |
| CDR3 | RAGENSGGIEPYYGMDV (SEQ ID NO: 28) | QQSYSAPYT (SEQ ID NO: 31) |
| NI-101.13 | | |
| CDR1 | RRSYYWG (SEQ ID NO: 32) | SGSSSNIGSNYVY (SEQ ID NO: 35) |
| CDR2 | SIHYSGSTYYNPSLKS (SEQ ID NO: 33) | RNNQRPS (SEQ ID NO: 36) |
| CDR3 | SRWGSSWVFDY (SEQ ID NO: 34) | AAWDDSLSGYV (SEQ ID NO: 37) |
| NI-101.12F6A | | |
| CDR1 | SYGMH (SEQ ID NO: 20) | RASQSISSYLN (SEQ ID NO: 23) |
| CDR2 | VIWFDGTKKYYTDSVKG (SEQ ID NO: 21) | AASSLQS (SEQ ID NO: 24) |
| CDR3 | DRGIGARRGPYYMDV (SEQ ID NO: 22) | QQSYSTPLT (SEQ ID NO: 25) |
| NI-101.13A | | |
| CDR1 | RRSYYWG (SEQ ID NO: 32) | RASQSISSYLN (SEQ ID NO: 46) |
| CDR2 | SIHYSGSTYYNPSLKS (SEQ ID NO: 33) | AASSLQS (SEQ ID NO: 47) |
| CDR3 | SRWGSSWVFDY (SEQ ID NO: 34) | QQSYSTRT (SEQ ID NO: 48) |
| NI-101.13B | | |
| CDR1 | RRSYYWG (SEQ ID NO: 32) | RASQSISSWLA (SEQ ID NO: 49) |
| CDR2 | SIHYSGSTYYNPSLKS (SEQ ID NO: 33) | KASSLES (SEQ ID NO: 50) |
| CDR3 | SRWGSSWVFDY (SEQ ID NO: 34) | QQYNSYSRT (SEQ ID NO: 51) |

In one embodiment, the antibody of the present invention is any one of the antibodies comprising an amino acid sequence of the $V_H$ and/or $V_L$ region as depicted in Tables 2 and 3. Alternatively, the antibody of the present invention is an antibody or antigen-binding fragment thereof, which competes for binding to the neoepitope with at least one of the antibodies having the $V_H$ and/or $V_L$ region as depicted in Tables 2 and 3. Those antibodies may be murine as well, however, humanized, xenogeneic, or chimeric human-murine antibodies being preferred, in particular for therapeutic applications. An antigen-binding fragment of the antibody can be, for example, a single chain Fv fragment (scFv), a F(ab') fragment, a F(ab) fragment, and an F(ab')$_2$ fragment. For some applications only the variable regions of the antibodies are required, which can be obtained by treating the antibody with suitable reagents so as to generate Fab', Fab, or F(ab")$_2$ portions. Such fragments are sufficient for use, for example, in immunodiagnostic procedures involving coupling the immunospecific portions of immunoglobulins to detecting reagents such as radioisotopes.

The present invention is further directed to isolated polypeptides which make up the antibodies of the present invention. Antibodies of the present invention comprise polypeptides, e.g., amino acid sequences encoding specific antigen binding regions derived from immunoglobulin molecules. A polypeptide or amino acid sequence "derived from" a designated protein refers to the origin of the polypeptide having a certain amino acid sequence. In certain cases, the polypeptide or amino acid sequence which is derived from a particular starting polypeptide or amino acid sequence has an amino acid sequence that is essentially identical to that of the starting sequence, or a portion thereof, wherein the portion consists of at least 10-20 amino acids, at least 20-30 amino acids, at least 30-50 amino acids, or which is otherwise identifiable to one of ordinary skill in the art as having its origin in the starting sequence.

In another embodiment, the present invention provides an isolated polypeptide comprising, consisting essentially of, or consisting of an immunoglobulin heavy chain variable region (VH), where at least one of VH-CDRs of the heavy chain variable region or at least two of the VH-CDRs of the heavy chain variable region are at least 80%, 85%, 90% or 95% identical to reference heavy chain VH-CDR1, VH-CDR2 or VH-CDR3 amino acid sequences from the antibodies disclosed herein. Alternatively, the VH-CDR1, VH-CDR2 and VH-CDR3 regions of the VH are at least 80%, 85%, 90% or 95% identical to reference heavy chain VH-CDR1, VH-CDR2 and VH-CDR3 amino acid sequences from the antibodies disclosed herein. Thus, according to this embodiment a heavy chain variable region of the invention has VH-CDR1, VH-CDR2 and VH-CDR3 polypeptide sequences related to the groups shown in Table 4, supra.

While Table 4 shows VH-CDRs defined by the Kabat system, other CDR definitions, e.g., VH-CDRs defined by the Chothia system, are also included in the present invention, and can be easily identified by a person of ordinary skill in the art using the data presented in Tables 2 and 3.

In another embodiment, the present invention provides an isolated polypeptide comprising, consisting essentially of, or consisting of an immunoglobulin heavy chain variable region (VH) in which the VH-CDR1, VH-CDR2 and VH-CDR3 regions have polypeptide sequences which are identical to the VH-CDR1, VH-CDR2 and VH-CDR3 groups shown in Table 4.

In another embodiment, the present invention provides an isolated polypeptide comprising, consisting essentially of, or consisting of an immunoglobulin heavy chain variable region (VH) in which the VH-CDR1, VH-CDR2 and VH-CDR3 regions have polypeptide sequences which are identical to the VH-CDR1, VH-CDR2 and VH-CDR3 groups shown in Table 4, except for one, two, three, four, five, or six amino acid substitutions in any one VH-CDR. In certain embodiments the amino acid substitutions are conservative.

In another embodiment, the present invention provides an isolated polypeptide comprising, consisting essentially of, or consisting of an immunoglobulin light chain variable region (VL), where at least one of the VL-CDRs of the light chain variable region or at least two of the VL-CDRs of the light chain variable region are at least 80%, 85%, 90% or 95% identical to reference light chain VL-CDR1, VL-CDR2 or VL-CDR3 amino acid sequences from antibodies disclosed herein. Alternatively, the VL-CDR1, VL-CDR2 and VL-CDR3 regions of the VL are at least 80%, 85%, 90% or 95% identical to reference light chain VL-CDR1, VL-CDR2 and VL-CDR3 amino acid sequences from antibodies disclosed herein. Thus, according to this embodiment a light chain variable region of the invention has VL-CDR1, VL-CDR2 and VL-CDR3 polypeptide sequences related to the polypeptides shown in Table 4, supra. While Table 4 shows VL-CDRs defined by the Kabat system, other CDR definitions, e.g., VL-CDRs defined by the Chothia system, are also included in the present invention.

In another embodiment, the present invention provides an isolated polypeptide comprising, consisting essentially of, or consisting of an immunoglobulin light chain variable region (VL) in which the VL-CDR1, VL-CDR2 and VL-CDR3 regions have polypeptide sequences which are identical to the VL-CDR1, VL-CDR2 and VL-CDR3 groups shown in Table 4.

In another embodiment, the present invention provides an isolated polypeptide comprising, consisting essentially of, or consisting of an immunoglobulin heavy chain variable region (VL) in which the VL-CDR1, VL-CDR2 and VL-CDR3 regions have polypeptide sequences which are identical to the VL-CDR1, VL-CDR2 and VL-CDR3 groups shown in Table 4, except for one, two, three, four, five, or six amino acid substitutions in any one VL-CDR. In certain embodiments the amino acid substitutions are conservative.

An immunoglobulin or its encoding cDNAs may be further modified. Thus, in a further embodiment the method of the present invention comprises any one of the step(s) of producing a chimeric antibody, humanized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-A1 0 239 400 and international application WO90/07861. A further source of antibodies to be utilized in accordance with the present invention are so-called xenogeneic antibodies. The general principle for the production of xenogeneic antibodies such as human antibodies in mice is described in, e.g., international applications WO91/10741, WO94/02602, WO96/34096 and WO 96/33735. As discussed above, the antibody of the invention may exist in a variety of forms besides complete antibodies; including, for example, Fv, Fab and F(ab)$_2$, as well as in single chains; see e.g. international application WO88/09344.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO00/30680 for corresponding technical details.

Additionally, the present invention encompasses small peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides may easily be synthesized or produced by recombinant means to produce a binding agent useful according to the invention. Such methods are well known to those of ordinary skill in the art. Peptides can be synthesized for example, using automated peptide synthesizers which are commercially available. The peptides can be produced by recombinant techniques by incorporating the DNA expressing the peptide into an expression vector and transforming cells with the expression vector to produce the peptide.

Hence, the present invention relates to any binding molecule, e.g., an antibody or binding fragment which is obtainable in accordance with above described means and display the mentioned properties, i.e. which specifically recognize a neoepitope. Such antibodies and binding molecules can be tested for their binding specificity and affinity by for example by using the method of isolating neoepitope specific binding molecules described hereinbefore.

As an alternative to obtaining immunoglobulins directly from the culture of immortalized B cells or B memory cells, the immortalized cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the de-sired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells may be used; for efficient processing, however, mammalian cells are preferred. Typical mammalian cell lines useful for this purpose include, but are not limited to, CHO cells, HEK 293 cells, or NSO cells.

The production of the antibody or analog is then undertaken by culturing the modified recombinant host under culture conditions appropriate for the growth of the host cells and the expression of the coding sequences. The antibodies are then recovered by isolating them from the culture. The expression systems are preferably designed to include signal peptides so that the resulting antibodies are secreted into the medium; however, intracellular production is also possible.

Once the target structure, e.g. the disease-associated protein has been tagged by the sample and respective binding molecule therein it may be identified by means and methods well known in the art, for example using mass spectrometric (MS) techniques such as those described in international application WO00/11208 and specifically those described in Hock et al., Nat Med 8 (2002), 1270-1275; Hock et al., Neuron 38 (2003), 547-554. Thus, in case the antibody identified in accordance with present invention produced in vitro binds to pathological structures, for example to beta-amyloid plaques in pathological brain area sections, but not significantly to healthy tissues, a promising antibody candidate has been identified whose molecular target structure can subsequently be enriched and purified via its binding properties to the antibody from pathological tissues and, as a result, can be identified and characterized by means of protein analytical and mass spectrometric methods, like for example MALDI/TOF (Williams, Methods Cell. Biol. 62 (2000), 449-453; Yates, J. Mass. Spectrum. 33 (1998), 1-19).

Accordingly, in another embodiment the present invention relates to an antigen which is recognized by the binding molecule, especially antibody of the present invention described hereinbefore, and which preferably is at least part of a disorder-associated protein.

In accordance with the above, the present invention also relates to a polynucleotide encoding the antigen or binding molecule of the present invention, in case of the antibody preferably at least a variable region of an immunoglobulin chain of the antibody described above. Typically, said variable region encoded by the polynucleotide comprises at least one complementarity determining region (CDR) of the $V_H$ and/or $V_L$ of the variable region of the said antibody. The person skilled in the art knows that each variable domain (the heavy chain $V_H$ and light chain $V_L$) of an antibody comprises three hypervariable regions, sometimes called complementarity determining regions or "CDRs" flanked by four relatively conserved framework regions or "FRs" and refer to the amino acid residues of an antibody which are responsible for antigen-binding. The hypervariable regions or CDRs of the human IgG subtype of antibody comprise amino acid residues from residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed Public Health Service, National Institutes of Health, Bethesda, Md. (1991) and/or those residues from a hypervariable loop, e.g. residues 26-32 (L1), 50-52 (L2) and 91-96 (L3) in the light chain variable domain and 26-32 (H1), 53-55 (H2) and 96-101 (H3) in the heavy chain variable domain as described by Chothia et al., J. Mol. Biol. 196 (1987), 901-917. Framework or FR residues are those variable domain residues other than and bracketing the hypervaribale regions. The term "specific binding" refers to antibody binding to a predetermined antigen. Typically, the antibody binds with a dissociation constant ($K_D$) of $10^{-7}$ M or less, and binds to the predetermined antigen with a $K_D$ that is at least twofold less than its $K_D$ for binding to a nonspecific antigen (e.g., BSA, casein, or any other specified polypeptide) other than the predetermined antigen. The phrases "an antibody recognizing an antigen" and "an antibody specific for an antigen" are used interchangeably herein with the term "an antibody which binds specifically to an antigen". As used herein "highly specific" binding means that the relative $K_D$ of the antibody for the specific target epitope, e.g. neoepitope is at least 10-fold less than the $K_D$ for binding that antibody to other ligands or to the native counterpart of the disease-associated protein.

The affinity or avidity of an antibody for an antigen can be determined experimentally using any suitable method; see, for example, Berzofsky et al., "Antibody-Antigen Interactions" In Fundamental Immunology, Paul, W. E., Ed., Raven Press New York, N.Y. (1984), Kuby, Janis Immunology, W. H. Freeman and Company New York, N.Y. (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art will readily appreciate that using the variable domains or CDRs described herein antibodies can be constructed according to methods known in the art, e.g., as described in European patent applications EP 0 451 216 A1 and EP 0 549 581 A1. Furthermore, the person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the variable regions as set forth in Table 4.

Binding molecules, e.g., antibodies, or antigen-binding fragments, variants, or derivatives thereof of the invention, as known by those of ordinary skill in the art, can comprise a constant region which mediates one or more effector functions. For example, binding of the C1 component of complement to an antibody constant region may activate the complement system. Activation of complement is important in the opsonisation and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the invention include an antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have a constant region, e.g., an IgG heavy chain constant region, which is altered to eliminate glycosylation, referred to elsewhere herein as aglycosylated or "agly" antibodies. Such "agly" antibodies may be prepared enzymatically as well as by engineering the consensus glycosylation site(s) in the constant region. While not being bound by theory, it is believed that "agly" antibodies may have an improved safety and stability profile in vivo. Methods of producing aglycosylated antibodies, having desired effector function are found for example in WO 2005/018572, which is incorporated by reference in its entirety.

In certain antibodies, or antigen-binding fragments, variants, or derivatives thereof described herein, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well know immunological techniques without undue experimentation.

Modified forms of antibodies, or antigen-binding fragments, variants, or derivatives thereof of the invention can be made from whole precursor or parent antibodies using techniques known in the art. Exemplary techniques are discussed in more detail herein.

In certain embodiments both the variable and constant regions of the antibodies, or antigen-binding fragments, variants, or derivatives thereof of the invention are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human antibodies can likewise be produced by various display technologies, e.g., phage display or other viral display systems, as described in more detail elsewhere herein.

Antibodies, or antigen-binding fragments, variants, or derivatives thereof of the invention can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

Antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In certain embodiments, antibodies, or antigen-binding fragments, variants, or derivatives thereof of the invention will not elicit a deleterious immune response in the animal to be treated, e.g., in a human. In certain embodiments, binding molecules, e.g., antibodies, or antigen-binding fragments thereof of the invention are derived from a patient, e.g., a human patient, and are subsequently used in the same species from which they are derived, e.g., human, alleviating or minimizing the occurrence of deleterious immune responses.

De-immunization can also be used to decrease the immunogenicity of an antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of binding polypeptides, e.g., neo-epitope-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, Cold Spring Harbor Laboratory Press, 2nd ed. (1988); Hammerling et al., in: *Monoclonal Antibodies and T-Cell Hybridomas* Elsevier, N.Y., 563-681 (1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art. In certain embodiments, antibodies of the present invention are derived from human B cells which have been immortalized via transformation with Epstein-Barr virus, as described herein.

In the well known hybridoma process (Kohler et al., *Nature* 256:495 (1975)) the relatively short-lived, or mortal, lymphocytes from a mammal, e.g., B cells derived from a human subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies, which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELISA), or neoepitope binding assays as described herein. After hybridoma cells are identified that produce antibodies of the desired specificity, affinity and/or activity, the clones may be subcloned by limiting dilution procedures and grown by standard methods (Goding, *Monoclonal Antibodies: Principles and Practice*, Academic Press, pp 59-103 (1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Antibody fragments that recognize specific epitopes may be generated by known techniques. For example, Fab and F(ab')$_2$ fragments may be produced recombinantly or by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain.

Completely human antibodies, such as described herein, are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. Human antibodies of the present invention are isolated, e.g., from patients who are symptom free but affected with the risk of developing a disorder, e.g., Alzheimer's disease, or a patient with the disorder but with an unusually stable disease course.

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as, but not limited to, E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

In one embodiment, an antibody of the invention comprises at least one heavy or light chain CDR of an antibody molecule. In another embodiment, an antibody of the invention comprises at least two CDRs from one or more antibody molecules. In another embodiment, an antibody of the invention comprises at least three CDRs from one or more antibody molecules. In another embodiment, an antibody of the invention comprises at least four CDRs from one or more antibody molecules. In another embodiment, an antibody of the invention comprises at least five CDRs from one or more antibody molecules. In another embodiment, an antibody of the invention comprises at least six CDRs from one or more antibody molecules. Exemplary antibody molecules comprising at least one CDR that can be included in the subject antibodies are described herein.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions. The framework regions may be naturally occurring or consensus framework regions, and preferably human framework regions (see, e.g., Chothia et al., *J. Mol. Biol.* 278:457-479 (1998) for a listing of human framework regions). In certain embodiments, the polynucleotide generated by the combination of the framework regions and CDRs encodes an antibody that specifically binds to at least one epitope of a desired polypeptide. In certain embodiments, one or more amino acid substitutions may be made within the framework regions, to, e.g., improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

Alternatively, techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be adapted to produce single chain antibodies. Single chain antibodies are formed by linking the heavy and light chain fragments of the Fv region via an amino acid bridge, resulting in a single chain antibody. Techniques for the assembly of functional Fv fragments in E. coli may also be used (Skerra et al., *Science* 242:1038-1041 (1988)).

In another embodiment, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibodies of the present invention can be produced by any method known in the art for the synthesis of antibodies, in particular, by chemical synthesis or preferably, by recombinant expression techniques as described herein.

In one embodiment, an antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an $IgG_1$ human constant domain (see, e.g., WO 02/060955A2 and WO02/096948A2). This vector is engineered to delete the CH2 domain and provide a synthetic vector expressing a domain deleted $IgG_1$ constant region.

In certain embodiments, antibodies, or antigen-binding fragments, variants, or derivatives thereof of the present invention are minibodies. Minibodies can be made using methods described in the art (see, e.g., U.S. Pat. No. 5,837,821 or WO 94/09817A1).

In one embodiment, an antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of antibody molecules (e.g., the VH regions and/or VL regions) described herein, which antibodies or fragments thereof immunospecifically bind to a disorder-associated polypeptide or fragment or variant thereof. Standard techniques known to those of skill in the art can be used to introduce mutations in the nucleotide sequence encoding an antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VH-CDR1, VH-CDR2, VH-CDR3, VL region, VL-CDR1, VL-CDR2, or VL-CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an disorder-associated polypeptide).

For example, it is possible to introduce mutations only in framework regions or only in CDR regions of an antibody molecule. Introduced mutations may be silent or neutral missense mutations, e.g., have no, or little, effect on an antibody's ability to bind antigen, indeed some such mutations do not alter the amino acid sequence whatsoever. These types of mutations may be useful to optimize codon usage, or improve a hybridoma's antibody production. Codon-optimized coding regions encoding antibodies of the present invention are disclosed elsewhere herein. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a disorder-associated polypeptide) can be determined using techniques described herein or by routinely modifying techniques known in the art.

IV. Polynucleotides Encoding Antibodies

In accordance with the above, the present invention also relates to a polynucleotide encoding a binding molecule of the present invention, e.g., an antibody. In case of the antibody the polynucleotide may encode at least a variable region of an immunoglobulin chain of the antibody described above. The polynucleotide of the invention encoding the above described antibody may be, e.g., DNA, cDNA, RNA or synthetically produced DNA or RNA or a recombinantly produced chimeric nucleic acid molecule comprising any of those polynucleotides either alone or in combination. Preferably said polynucleotide is part of a vector. Such vectors may comprise further genes such as marker genes which allow for the selection of said vector in a suitable host cell and under suitable conditions. Preferably, the polynucleotide of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally associated or heterologous promoter regions.

A polynucleotide encoding an antibody, or antigen-binding fragment, variant, or derivative thereof can be composed of any polyribonucleotide or polydeoxribonucleotide, which may be unmodified RNA or DNA or modified RNA or DNA. For example, a polynucleotide encoding an antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an antibody, or antigen-binding fragment, variant, or derivative thereof can be composed of triple-stranded regions comprising RNA or DNA or both RNA and DNA. A polynucleotide encoding an antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

In one embodiment, the present invention provides an isolated polynucleotide comprising, consisting essentially of, or consisting of a nucleic acid encoding an immunoglobulin heavy chain variable region (VH), where at least one of the CDRs of the heavy chain variable region or at least two of the VH-CDRs of the heavy chain variable region are at least 80%, 85%, 90% or 95% identical to reference heavy chain VH-CDR1, VH-CDR2, or VH-CDR3 amino acid sequences from the antibodies disclosed herein. Alternatively, the VH-CDR1, VH-CDR2, and VH-CDR3 regions of the VH are at least 80%, 85%, 90% or 95% identical to reference heavy chain VH-CDR1, VH-CDR2, and VH-CDR3 amino acid sequences from the antibodies disclosed herein. Thus, according to this embodiment a heavy chain variable region of the invention has VH-CDR1, VH-CDR2, or VH-CDR3 polypeptide sequences related to the polypeptide sequences shown in Table 4.

In another embodiment, the present invention provides an isolated polynucleotide comprising, consisting essentially of, or consisting of a nucleic acid encoding an immunoglobulin light chain variable region (VL), where at least one of the VL-CDRs of the light chain variable region or at least two of the VL-CDRs of the light chain variable region are at least 80%, 85%, 90% or 95% identical to reference light chain VL-CDR1, VL-CDR2, or VL-CDR3 amino acid sequences from the antibodies disclosed herein. Alternatively, the VL-CDR1, VL-CDR2, and VL-CDR3 regions of the VL are at least 80%, 85%, 90% or 95% identical to reference light chain VL-CDR1, VL-CDR2, and VL-CDR3 amino acid sequences from the antibodies disclosed herein. Thus, according to this embodiment a light chain variable region of the invention has VL-CDR1, VL-CDR2, or VL-CDR3 polypeptide sequences related to the polypeptide sequences shown in Table 4.

In another embodiment, the present invention provides an isolated polynucleotide comprising, consisting essentially of, or consisting of a nucleic acid encoding an immunoglobulin heavy chain variable region (VH) in which the VH-CDR1, VH-CDR2, and VH-CDR3 regions have polypeptide sequences which are identical to the VH-CDR1, VH-CDR2, and VH-CDR3 groups shown in Table 4.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

TABLE 5

Polynucleotide sequences of the $V_H$ region of neoepitope specific antibodies.

| Antibody | Variable heavy chain sequence |
| --- | --- |
| NI-101.10 (SEQ ID NO: 3) | GAGGTGCAGCTAGTGCAGTCTGGGGGAGGCGTGGTCCAGCCTGGGAGGTCCCTGAGACTCTCC<br>TGTGCAGCGTCTGGATTCGCCTTCAGTAGCTATGGCATACACTGGGTCCGCCAGGCTCCAGGCA<br>AGGGGCTGGAGTGGGTGGCAGTTATATGGTTTGATGGAACTAAAAAATACTATACAGACTCCGTG<br>AAGGGCAGATTCACCATCTCCAGAGACAATTCCAAGAACACACTGTATCTGCAAATGAACACCCT<br>GAGAGCCGAGGACACGGCTGTGTATTACTGTGCGAGAGATAGGGGTATAGGAGCTCGGCGGGG<br>GCCGTACTACATGGACGTCTGGGGCAAAGGGACCACGGTCACCGTCTCCTCA |

TABLE 5-continued

Polynucleotide sequences of the V_H region of neoepitope specific antibodies.

| Antibody | Variable heavy chain sequence |
|---|---|
| NI-101.11 (SEQ ID NO: 56) | GAGGTGCAGCTGGTGCAGTCTGGGGGAGGCGTGGTCCAGCCTGGGAGGTCCCTGAGACTCTCC TGTGCAGCGTCTGGATTCGCCTTCAGTAGCTATGGCATGCACTGGGTCCGCCAGGCTCCAGGCA AGGGGCTGGAGTGGGTGGCAGTTATATGGTTTGATGGAACTAAAAAATACTATACAGACTCCGTG AAGGGCAGATTCACCATCTCCAGAGACAATTCCAAGAACACACTGTATCTGCAAATGAACACCCT GAGAGCCGAGGACACGGCTGTGTATTACTGTGCGAGAGATAGGGGTATAGGAGCTCGGCGGGG GCCGTACTACATGGACGTCTGGGGCAAAGGGACCACGGTCACCGTCTCCTCA |
| NI-101.11 (SEQ ID NO: 5) (codon-optimized) | GAGGTGCAGCTGGTGCAGAGCGGCGGCGGCGTGGTGCAGCCCGGCCGGAGCCTGCGGCTGAG CTGCGCCGCCAGCGGCTTCGCCTTCAGCAGCTACGGCATGCACTGGGTGCGGCAGGCCCCCGG CAAGGGCCTGGAGTGGGTGGCCGTGATCTGGTTCGACGGCACCAAGAAGTACTACACCGACAGC GTGAAGGGCCGGTTCACCATCAGCCGGGACAACAGCAAGAACACCCTGTACCTGCAGATGAACA CCCTGCGGGCCGAGGACACCGCCGTGTACTACTGCGCCCGGGACCGGGGCATCGGCGCCCGG CGGGGCCCCTACTACATGGACGTGTGGGGCAAGGGCACCACCGTGACCGTGAGCAGC |
| NI-101.12 (SEQ ID NO: 9) | GAGGTGCAGCTGGTGGAGAGCGGCCCCGGCCTGGTGAAGCCCGCCGAGACCCTGAGCCTGACC TGCACCGTGAGCGGCGGCAGCATCCGGAGCGGCAGCATCTGCTGGTACTGGATCCGGCAGCCC CCCGGCAAGGGCCTGGAGTGGATCGGCTACTTCTGCTACAGCGGCGCCCACCTTCTACACCCCA GCCTGCGGGCCGGCTGACCATCAGCGTGGACGCCAGCAAGAACCAGCTGAGCCTGAGCCTGA GCAGCGTGACCGCCGCCGACACCGCCGTGTACTACTGCGCCCGGCGGGCCGGCGAGAACAGC GGCGGCATCGAGCCCTACTACGGCATGGACGTGTGGGGCCAGGGCACCACCGTGACCGTGAGC AGC |
| NI-101.13 (SEQ ID NO: 13) | CAGGTACAGCTGCAGGAGTCAGGCCCAGGACTGGTGAAGCCTTCGGAGACCCTGTCCCTCACCT GCACTGTCTCTGGTGGCTCCATCAGCAGAAGAAGTTACTACTGGGGCTGGATCCGCCAGTCCCC AGGGAAGGGGCTGGAGTGGAGTGGAAGTATCCATTATAGCGGGCAGCACCTACTACAACCCGTCC CTCAAGAGTCGAGTCACCATATCTGTAGACACGTCCAAGAACCAGTTCTCCCTGAAACTGAGCTC TGTTACCGCCGCAGACACGGCTGTCTATTACTGTGCGAGATCACGTTGGGGCAGCAGCTGGGTA TTTGACTACTGGGGCCAGGGCACACTGGTCACCGTCTCTTCG |
| NI-101.12F 6A (SEQ ID NO: 38) | CAGGTGCAGCTGGTGGAGTCTGGGGGAGGCGTGGTCCAGCCTGGGAGGTCCCTGAGACTCTCC TGTGCAGCGTCTGGATTCGCCTTCAGTAGCTATGGCATGCACTGGGTCCGCCAGGCTCCAGGCA AGGGGCTGGAGTGGGTGGCAGTTATATGGTTTGATGGAACTAAAAAATACTATACAGACTCCGTG AAGGGCAGATTCACCATCTCCAGAGACAATTCCAAGAACACACTGTATCTGCAAATGAACACCCT GAGAGCCGAGGACACGGCTGTGTATTACTGTGCGAGAGATAGGGGTATAGGAGCTCGGCGGGG GCCGTACTACATGGACGTCTGGGGCAAAGGGACCACGGTCACCGTCTCCTCA |
| NI-101.13A (SEQ ID NO: 52) | CAGGTGCAGCTGCAGGAGTCGGGCCCAGGACTGGTGAAGCCTTCGGAGACCCTGTCCCTCACCT GCACTGTCTCTGGTGGCTCCATCAGCAGAAGAAGTTACTACTGGGGCTGGATCCGCCAGTCCCC AGGGAAGGGGCTGGAGTGGAGTGGAAGTATCCATTATAGCGGGAGCACCTACTACAACCCGTCC CTCAAGAGTCGAGTCACCATATCTGTAGACACGTCCAAGAACCAGTTCTCCCTGAAACTGAGCTC TGTTACCGCCGCAGACACGGCTGTCTATTACTGTGCGAGATCACGTTGGGGCAGCAGCTGGGTA TTTGACTACTGGGGCCAGGGAACCCTGGTCACCGTCTCCTCG |
| NI-101.13B (SEQ ID NO: 53) | CAGGTGCAGCTGCAGGAGTCGGGCCCAGGACTGGTGAAGCCTTCGGAGACCCTGTCCCTCACCT GCACTGTCTCTGGTGGCTCCATCAGCAGAAGAAGTTACTACTGGGGCTGGATCCGCCAGTCCCC AGGGAAGGGGCTGGAGTGGAGTGGAAGTATCCATTATAGCGGGAGCACCTACTACAACCCGTCC CTCAAGAGTCGAGTCACCATATCTGTAGACACGTCCAAGAACCAGTTCTCCCTGAAACTGAGCTC TGTTACCGCCGCAGACACGGCTGTCTATTACTGTGCGAGATCACGTTGGGGCAGCAGCTGGGTA TTTGACTACTGGGGCCAGGGAACCCTGGTCACCGTCTCCTCG |

TABLE 6

Polynucleotide sequences of the V_L region of neoepitope specific antibodies.

| Antibody | Variable light chain sequence (kappa or lambda) |
|---|---|
| NI-101.10 and NI-101.11 (SEQ ID NO: 7) | GAAATTGTGCTGACTCAGTCTCCATCCTCCCTGTCTGCATCTGTAGGAGACAGAGTCACCATCACT TGCCGGGCAAGTCAGAGCATTAGCAGCTATTTAAATTGGTATCAACAGAAACCAGGGAAAGCCCC TAAGCTCCTGATCTATGCTGCATCCAGTTTGCAAAGTGGGGTCCCATCAAGGTTCAGTGGCAGTG GATCTGGGACAGATTTCACTCTCACCATCAGCAGTCTGCAACCTGAAGATTTTGCAACTTATTACT GTCAGCAGAGTTACAGTACCCCTCTCACTTTCGGCGGAGGGACCAAGCTCGAGATCAAACGTAC G |
| NI-101.12 (SEQ ID NO: 11) | GACGAGATCGTGCTGACCCAGAGCCCCAGCAGCCTGAGCGCCAGCATCGGCGACCGGGTGACC ATCACCTGCCGGGCCAGCGAGAGCATCAACAAGTACGTGAACTGGTACCAGCAGAAGCCCGGCA AGGCCCCCAAGCTGCTGATCTACGCCGCCAGCAGCCTGCAGAGCGGCGCCCCCAGCCGGGTGA GCGGCAGCGGCTTCGGCCGGGACTTCAGCCTGACCATCAGCGGCCTGCAGGCCGAGGACTTCG GCGCCTACTTCTGCCAGCAGAGCTACAGCGCCCCCTACACCTTCGGCCAGGGCACCAAGGTGGA GATCAAGCGGACC |

TABLE 6-continued

Polynucleotide sequences of the V_L region of neoepitope specific antibodies.

| Antibody | Variable light chain sequence (kappa or lambda) |
|---|---|
| NI-101.13 (SEQ ID NO: 15) | CAGAGCGTGCTGACCCAGCCGCCGAGCGCGAGCGGCACCCCGGGCCAGCGCGTGACCATTAGC TGCAGCGGCAGCAGCAGCAACATTGGCAGCAACTATGTGTATTGGTATCAGCAGCCGCCGGGCA CCGCGCCGAAACTGCTGATTTATCGCAACAACCAGCGCCCGAGCGGCGTGCCGGATCGCTTTAG CGGCAGCAAAAGCGGCACCAGCGCGAGCCTGGCGATTAGCGGCCTGCGCAGCGAAGATGAAGC GGATTATTATTGCGCGGCGTGGGATGATAGCCTGAGCGGCTATGTGTTTGGCACCGGCACCAAA GTGACCGTGCTG |
| NI-101.12F 6A (SEQ ID NO: 40) | GACATCCAGATGACCCAGTCTCCATCCTCCCTGTCTGCATCTGTAGGAGACAGAGTCACCATCAC TTGCCGGGCAAGTCAGAGCATTAGCAGCTATTTAAATTGGTATCAACAGAAACCAGGGAAAGCCC CTAAGCTCCTGATCTATGCTGCATCCAGTTTGCAAAGTGGGGTCCCATCAAGGTTCAGTGGCAGT GGATCTGGGACAGATTTCACTCTCACCATCAGCAGTCTGCAACCTGAAGATTTTGCAACTTATTAC TGTCAGCAGAGTTACAGTACCCCTCTCACTTTCGGCGGAGGGACCAAGGTGGAGATCAAACGT |
| NI-101.13A (SEQ ID NO: 54) | GACATCCAGTTGACCCAGTCTCCATCCTCCCTGTCTGCATCTGTAGGAGACAGAGTCACCATCAC TTGCCGGGCAAGTCAGAGCATTAGCAGCTATTTAAATTGGTATCAGCAGAAACCAGGGAAAGCCC CTAAGCTCCTGATCTATGCTGCATCCAGTTTGCAAAGTGGGGTCCCATCAAGGTTCAGTGGCAGT GGATCTGGGACAGATTTCACTCTCACCATCAGCAGTCTGCAACCTGAAGATTTTGCAACTTACTAC TGTCAACAGAGTTACAGTACCAGAACGTTCGGCCAAGGGACCAAGGTGGAGATCAAACGTACG |
| NI-101.13B (SEQ ID NO: 55) | GACATCCAGTTGACCCAGTCTCCTTCCACCCTGTCTGCATCTGTAGGAGACAGAGTCACCATCAC TTGCCGGGCCAGTCAGAGTATTAGTAGCTGGTTGGCCTGGTATCAGCAGATTCCAGGGAAAGCC CCTAAGCTCCTGATCTATAAGGCGTCTAGTTTAGAAAGTGGGGTCCCATCAAGGTTCAGCGGCAG TGGATCTGGGACAGAATTCACTCTCACCATCAGCAGCCTGCAGCCTGATGATTTTGCAACTTATTA CTGCCAACAGTATAATAGTTATTCTCGAACGTTCGGCCAAGGGACCAAGCTGGAGATCAAACGTA CG |

In this respect, the person skilled in the art will readily appreciate that the polynucleotides encoding at least the variable domain of the light and/or heavy chain may encode the variable domains of both immunoglobulin chains or only one. Likewise, said polynucleotides may be under the control of the same promoter or may be separately controlled for expression. Possible regulatory elements permitting expression in prokaryotic host cells comprise, e.g., the PL, lac, trp or tac promoter in *E. coli*, and examples for regulatory elements permitting expression in eukaryotic host cells are the AOX1 or GAL1 promoter in yeast or the CMV-, SV40-, RSV-promoter, CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including a C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogen), or pSPORT1 (GIBCO BRL). Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the immunoglobulin light chains, heavy chains, light/heavy chain dimers or intact antibodies, binding fragments or other immunoglobulin forms may follow; see, Beychok, Cells of Immunoglobulin Synthesis, Academic Press, N.Y., (1979).

The present invention also includes fragments of the polynucleotides of the invention, as described elsewhere. Additionally polynucleotides which encode fusion polynucleotides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody, or antigen-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably poly A+RNA, isolated from, any tissue or cells expressing the neoantigen-specific antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning, A Laboratory Manual*, 2d Ed., Cold Spring Harbor Laboratory, Cold Spring Harbor, N.Y. (1990) and Ausubel et al., eds., *Current Protocols in Molecular Biology*, John Wiley & Sons, NY (1998), which are both incorporated by reference herein in their entireties), to generate antibodies having a different amino acid sequence, for example to create amino acid substitutions, deletions, and/or insertions.

V. Expression of Antibody Polypeptides

The present invention also involves a method for producing cells capable of expressing an antibody of the invention or its corresponding immunoglobulin chain(s) comprising genetically engineering cells with the polynucleotide or with the vector of the invention. The cells obtainable by the method of the invention can be used, for example, to test the interaction of the antibody of the invention with its antigen.

Following manipulation of the isolated genetic material to provide antibodies, or antigen-binding fragments, variants, or derivatives thereof of the invention, the polynucleotides encoding the antibodies are typically inserted in an expression vector for introduction into host cells that may be used to produce the desired quantity of antibody.

Recombinant expression of an antibody, or fragment, derivative or analog thereof, e.g., a heavy or light chain of an antibody which binds to a target molecule described herein. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The present invention relates to vectors, particularly plasmids, cosmids, viruses and bacteriophages used conventionally in genetic engineering that comprise a polynucleotide encoding the antigen or preferably a variable domain of an immunoglobulin chain of an antibody of the invention; optionally in combination with a polynucleotide of the invention that encodes the variable domain of the other immunoglobulin chain of the antibody of the in-vention. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells. The vectors containing the polynucleotides of the invention (e.g., the heavy and/or light variable domain(s) of the immunoglobulin chains encoding sequences and expression control sequences) can be transferred into the host cell by well known methods, which vary depending on the type of cellular host. For example, calcium chloride transfection is commonly utilized for prokaryotic cells, whereas calcium phosphate treatment or electroporation may be used for other cellular hosts; see Sambrook, supra.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) synthetic as discussed above. In one embodiment, this is effected using a proprietary expression vector of Biogen IDEC, Inc., referred to as NEOSPLA (disclosed in U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6N5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the antibodies, or antigen-binding fragments, variants, or derivatives thereof of the invention may be expressed using polycistronic constructs such as those disclosed in United States Patent Application Publication No. 2003-0157641 A1, filed Nov. 18, 2002 and incorporated herein in its entirety. In these novel expression systems, multiple gene products of interest such as heavy and light chains of antibodies may be produced from a single polycistronic construct. These systems advantageously use an internal ribosome entry site (IRES) to provide relatively high levels of antibodies. Compatible IRES sequences are disclosed in U.S. Pat. No. 6,193,980 which is also incorporated herein. Those skilled in the art will appreciate that such expression systems may be used to effectively produce the full range of antibodies disclosed in the instant application.

More generally, once the vector or DNA sequence encoding a monomeric subunit of the antibody has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Vectors, Rodriguez and Denhardt, Eds., Butterworths, Boston, Mass., Chapter 24.2, pp. 470-472 (1988). Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

The present invention furthermore relates to host cells transformed with a polynucleotide or vector of the invention. Said host cell may be a prokaryotic or eukaryotic cell. The polynucleotide or vector of the invention which is present in the host cell may either be integrated into the genome of the host cell or it may be maintained extrachromosomally. The host cell can be any prokaryotic or eukaryotic cell, such as a bacterial, insect, fungal, plant, animal or human cell. Preferred fungal cells are, for example, those of the genus *Saccharomyces*, in particular those of the species *S. cerevisiae*. The term "prokaryotic" is meant to include all bacteria which can be transformed or transfected with a DNA or RNA molecules for the expression of an antibody of the invention or the corresponding immu-noglobulin chains. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells, most preferably HEK 293, NSO and CHO cells. Depending upon the host employed in a recombinant production procedure, the antibodies or immunoglobulin chains encoded by the polynucleotide of the present invention may be glycosylated or may be non-glycosylated. Antibodies of the invention or the corresponding immunoglobulin chains may also include an initial methionine amino acid residue. A polynucleotide of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, Molecular Cloning: A Laboratory Manual, Cold Spring Harbor Laboratory, Cold Spring Harbor, NY, 1989). The genetic constructs and methods described therein can be utilized for expression of the antibody of the invention or the corresponding immunoglobulin chains in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A., which is incorporated herein by reference). Furthermore, transgenic animals, preferably mammals, comprising cells of the invention may be used for the large scale production of the antibody of the invention.

Thus, in a further embodiment, the present invention relates to a method for the production of a disorder-associated protein specific binding molecule, e.g., an antibody or a binding fragment or immunoglobulin chain(s) thereof, said method comprising
  (a) culturing a cell as described above; and
  (b) isolating said antigen, binding molecule, antibody or binding fragment or immunoglobulin chain(s) thereof from the culture.

The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or its corresponding immunoglobulin chain(s) of the invention can then be isolated from the growth medium, cellular lysates, or cellular membrane fractions. The isolation and purification of the, e.g., recombinantly expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention. It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

Substantially pure immunoglobulins of at least about 90 to 95% homogeneity are preferred, and 98 to 99% or more homogeneity most preferred, for pharmaceutical uses. Once purified, partially or to homogeneity as desired, the antibodies may then be used therapeutically (including extracorporally) or in developing and performing assay procedures.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3×63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 1980) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); TIB TECH 11(5):155-215 (May, 1993); and hygro, which confers resistance to hygromycin (Santerre et al., Gene 30:147 (1984). Methods commonly known in the art of recombinant DNA technology which can be used are described in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, *The use of vectors based on gene amplification for the expression of cloned genes in mammalian cells* in DNA cloning, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding antibodies, or antigen-binding fragments, variants, or derivatives thereof of the invention can also be expressed non-mammalian cells such as bacteria or insect or yeast or plant cells. Bacteria which readily take up nucleic acids include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO02/096948A2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO 1 2:1791 (1983)), in which the antibody coding sequence may be ligated individually into the vector in frame with the lacZ coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., Nature 282:39 (1979); Kingsman et al., Gene 7:141 (1979); Tschemper et al., Gene 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics 85:12 (1977)). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in US 2002 0123057 A1.

VI. Fusion Proteins and Conjugates

The antibodies of the present invention can comprise a further domain, said domain being linked by covalent or non-covalent bonds. The linkage can be based on genetic fusion according to the methods known in the art and described above or can be performed by, e.g., chemical cross-linking as described in, e.g., international application WO94/04686. The additional domain present in the fusion protein comprising the antibody of the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the antibody of the invention or vice versa. The therapeutically or diagnostically active agent can be coupled to the antibody of the invention or an antigen-binding fragment thereof by various means. This includes, for example, single-chain fusion proteins comprising the variable regions of the antibody of the invention coupled by covalent methods, such as peptide linkages, to the therapeutically or diagnostically active agent. Further examples include molecules which comprise at least an antigen-binding fragment coupled to additional molecules covalently or non-covalently include those in the following non-limiting illustrative list. Traunecker, Int. J. Cancer Surp. SuDP 7 (1992), 51-52, describe the bispecific reagent janusin in which the Fv region directed to CD3 is coupled to soluble CD4 or to other ligands such as OVCA and IL-7. Similarly, the variable regions of the antibody of the invention can be constructed into Fv molecules and coupled to alternative ligands such as those illustrated in the cited article. Higgins, J. Infect Disease 166 (1992), 198-202, described a hetero-conjugate antibody composed of OKT3 cross-linked to an antibody directed to a specific sequence in the V3 region of GP120. Such hetero-conjugate antibodies can also be constructed using at least the variable regions contained in the antibody of the invention methods. Additional examples of specific antibodies include those described by Fanger, Cancer Treat. Res. 68 (1993), 181-194 and by Fanger, Crit. Rev. Immunol. 12 (1992), 101-124.

In a further embodiment of the present invention, the binding molecule, antibody, immunoglobulin chain or a binding fragment thereof or the antigen is detectably labeled. Labeling agents can be coupled either directly or indirectly to the antibodies or antigens of the invention. One example of indirect coupling is by use of a spacer moiety.

Hence, the biological activity of the binding molecules, e.g. antibodies identified here suggests that they have sufficient affinity to make them potential candidates for drug localization to cells expressing the appropriate surface structures of the diseased cell and tissue, respectively. This targeting and binding to cells could be useful for the delivery of therapeutically or diagnostically active agents and gene therapy/gene delivery. Molecules/particles with an antibody of the invention would bind specifically to cells/tissues expressing the variant form of the pathological protein, and therefore could have diagnostic and therapeutic use. Thus, the binding molecule, e.g., antibody or antigen binding fragment thereof of the present invention can be labeled (e.g., fluorescent, radioactive, enzyme, nuclear magnetic, heavy metal) and used to detect specific targets in vivo or in vitro including "immunochemistry" like assays in vitro. In vivo they could be used in a manner similar to nuclear medicine imaging techniques to detect tissues, cells, or other material expressing the neoepitope. Thus, in a further embodiment the present invention relates to the use of a binding molecule or an antibody of the present invention or binding fragment thereof for the preparation of a composition for in vivo detection of or targeting a therapeutic and/or diagnostic agent to a disorder-associated protein in the brain, detecting, suppressing formation of or reducing pathological protein aggregates or conformations in a subject, for improving cognition or slowing or reversing cognitive decline associated with diseases, or for extra-corporal extraction of pathological compounds or their precursors from body fluids.

In certain embodiments, antibody polypeptide comprises an amino acid sequence or one or more moieties not normally associated with an antibody. Exemplary modifications are described in more detail below. For example, a single-chain fv antibody fragment of the invention may comprise a flexible linker sequence, or may be modified to add a functional moiety (e.g., PEG, a drug, a toxin, or a label).

An antibody polypeptide of the invention may comprise, consist essentially of, or consist of a fusion protein. Fusion proteins are chimeric molecules which comprise, for example, an immunoglobulin antigen-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. Antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification may be present in the same or varying degrees at several sites in a given antibody. Also, a given antibody may contain many types of modifications. Antibodies may be branched, for example, as a result of ubiquitination, and they may be cyclic, with or without branching. Cyclic, branched, and branched cyclic antibodies may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, e.g., *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

The present invention also provides for fusion proteins comprising an antibody, or antigen-binding fragment, variant, or derivative thereof, and a heterologous polypeptide. In one embodiment, a fusion protein of the invention comprises, consists essentially of, or consists of, a polypeptide having the amino acid sequence of any one or more of the VH regions of an antibody of the invention or the amino acid sequence of any one or more of the VL regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the VH-CDRs of an antibody, or fragments, variants, or derivatives thereof, or the amino acid sequence of any one, two, three of the VL-CDRs of an antibody, or fragments, variants, or derivatives thereof, and a heterologous polypeptide sequence. In one embodiment, the fusion protein comprises a polypeptide having the amino acid sequence of a VH-CDR3 of an antibody of the present invention, or fragment, derivative, or variant thereof, and a heterologous polypeptide sequence, which fusion protein specifically binds to at least one neoepitope of a disorder-associated protein. In another embodiment, a fusion protein comprises a polypeptide having the amino acid sequence of at least one VH region of an antibody of the invention and the amino acid sequence of at least one VL region of an antibody of the invention or fragments, derivatives or variants thereof, and a heterologous polypeptide sequence. Preferably, the VH and VL regions of the fusion protein correspond to a single source antibody (or scFv or Fab fragment) which specifically binds at least one neoepitope of a disorder-associated protein. In yet another embodiment, a fusion protein for use in the diagnostic and treatment methods disclosed herein comprises a polypeptide having the amino acid sequence of any one, two, three or more of the VH CDRs of an antibody and the amino acid sequence of any one, two, three or more of the VL CDRs of an antibody, or fragments or variants thereof, and a heterologous polypeptide sequence. Preferably, two, three, four, five, six, or more of the VH-CDR(s) or VL-CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., *Proc. Natl. Acad. Sci. USA* 84:2936-2940 (1987)); CD4 (Capon et al., *Nature* 337:525-531 (1989); Traunecker et al., *Nature* 339:68-70 (1989); Zettmeissl et al., *DNA Cell Biol. USA* 9:347-353 (1990); and Byrn et al., *Nature* 344:667-670 (1990)); L-selectin (homing receptor) (Watson et al., *J. Cell. Biol.* 110:2221-2229 (1990); and Watson et al., *Nature* 349:164-167 (1991)); CD44 (Aruffo et al., *Cell* 61:1303-1313 (1990)); CD28 and B7 (Linsley et al., *J. Exp. Med.* 173:721-730 (1991)); CTLA-4 (Lisley et al., *J. Exp. Med.* 174:561-569 (1991)); CD22 (Stamenkovic et al., *Cell* 66:1133-1144 (1991)); TNF receptor (Ashkenazi et al., *Proc. Natl. Acad. Sci. USA* 88:10535-10539 (1991); Lesslauer et al., *Eur. J. Immunol.* 27:2883-2886 (1991); and Peppel et al., *J. Exp. Med.* 174:1483-1489 (1991)); and IgE receptor a (Ridgway and Gorman, *J. Cell. Biol. Vol.* 115, Abstract No. 1448 (1991)).

As discussed elsewhere herein, antibodies, or antigen-binding fragments, variants, or derivatives thereof of the invention may be fused to heterologous polypeptides to increase the in vivo half life of the polypeptides or for use in immunoassays using methods known in the art. For example, in one embodiment, PEG can be conjugated to the antibodies of the invention to increase their half-life in vivo. Leong, S. R., et al., *Cytokine* 16:106 (2001); *Adv. in Drug Deliv. Rev.* 54:531 (2002); or Weir et al., *Biochem. Soc. Transactions* 30:512 (2002).

Moreover, antibodies, or antigen-binding fragments, variants, or derivatives thereof of the invention can be fused to marker sequences, such as a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

Fusion proteins can be prepared using methods that are well known in the art (see for example U.S. Pat. Nos. 5,116,964 and 5,225,538). The precise site at which the fusion is made may be selected empirically to optimize the secretion or binding characteristics of the fusion protein. DNA encoding the fusion protein is then transfected into a host cell for expression.

Antibodies of the present invention may be used in non-conjugated form or may be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof of the invention can be labeled or conjugated either before or after purification, when purification is performed.

In particular, antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

The above described fusion protein may further comprise a cleavable linker or cleavage site for proteinases. These spacer moieties, in turn, can be either insoluble or soluble (Diener et al., Science 231 (1986), 148) and can be selected to enable drug release from the antigen at the target site. Examples of therapeutic agents which can be coupled to the antibodies and antigens of the present invention for immunotherapy are drugs, radioisotopes, lectins, and toxins. The drugs with which can be conjugated to the antibodies and antigens of the present invention include compounds which are classically referred to as drugs such as mitomycin C, daunorubicin, and vinblastine. In using radioisotopically conjugated antibodies or antigens of the invention for, e.g., immunotherapy, certain isotopes may be more preferable than others depending on such factors as leukocyte distribution as well as stability and emission. Depending on the autoimmune response, some emitters may be preferable to others. In general, a and B particle emitting radioisotopes are preferred in immunotherapy. Preferred are short range, high energy a emitters such as $^{212}$Bi. Examples of radioisotopes which can be bound to the antibodies or antigens of the invention for therapeutic purposes include, but are not limited to $^{125}$I, $^{151}$I, $^{90}$Y, $^{67}$Cu, $^{64}$Cu, $^{212}$Bi, $^{212}$At, $^{211}$Pb, $^{47}$Sc, $^{109}$Pd and $^{188}$Re. Other therapeutic agents which can be coupled to the binding molecule, e.g., antibody or antigen binding fragment thereof of the invention, as well as ex vivo and in vivo therapeutic protocols, are known, or can be easily ascertained, by those of ordinary skill in the art. Wherever appropriate the person skilled in the art may use a polynucleotide of the invention encoding any one of the above described antibodies, antigens or the corresponding vectors instead of the proteinaeous material itself.

Those skilled in the art will appreciate that conjugates may also be assembled using a variety of techniques depending on the selected agent to be conjugated. For example, conjugates with biotin are prepared e.g. by reacting a binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the antibodies, or antigen-binding fragments, variants, or derivatives thereof of the invention are prepared in an analogous manner.

The present invention further encompasses antibodies, or antigen-binding fragments, variants, or derivatives thereof of the invention conjugated to a diagnostic or therapeutic agent. The antibodies can be used diagnostically to, for example, monitor the development or progression of a neurological disease as part of a clinical testing procedure to, e.g., determine the efficacy of a given treatment and/or prevention regimen. Detection can be facilitated by coupling the antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, e.g., U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

An antibody, or antigen-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., *Diagnostic Horizons* 2:1-7 (1978)); Voller et al., *J. Clin. Pathol.* 31:507-520 (1978); Butler, J. E., *Meth. Enzymol.* 73:482-523 (1981); Maggio, E. (ed.), *Enzyme Immunoassay*, CRC Press, Boca Raton, Fla., (1980); Ishikawa, E. et al., (eds.), *Enzyme Immunoassay*, Kgaku Shoin, Tokyo (1981). The enzyme, which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibody, or antigen-binding fragment, variant, or derivative thereof, it is possible to detect the antibody through the use of a radioimmunoassay (RIA) (see, for example, Weintraub, B., *Principles of Radioimmunoassays, Seventh Training Course on Radioligand Assay Techniques*, The Endocrine Society, (March 1986)), which is incorporated by reference herein). The radioactive isotope can be detected by means including, but not limited to, a gamma counter, a scintillation counter, or autoradiography.

An antibody, or antigen-binding fragment, variant, or derivative thereof can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an antibody, or antigen-binding fragment, variant, or derivative thereof are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in *Controlled Drug Delivery* (2nd Ed.), Robinson et al. (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody-Toxin Conjugates", *Immunol. Rev.* 62:119-58 (1982).

In certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong, S. R., et al., *Cytokine* 16:106 (2001); *Adv. in Drug Deliv. Rev.* 54:531 (2002); or Weir et al., *Biochem. Soc. Transactions* 30:512 (2002).

VII. Compositions and Methods of Use

Moreover, the present invention relates to compositions comprising the aforementioned binding molecule, e.g., antibody or antigen binding fragment thereof of the present invention or chemical derivatives thereof, or the polynucleotide, vector or cell of the invention. The composition of the present invention may further comprise a pharmaceutically acceptable carrier. The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Furthermore, the pharmaceutical composition of the present invention may comprise further agents such as interleukins or interferons depending on the intended use of the pharmaceutical composition. For example, for use in the treatment of Alzheimer's disease the additional agent may selected from the group consisting of small organic molecules, anti-Abeta antibodies, and combinations thereof. Hence, in a particular preferred embodiment the present invention relates to the use of the binding molecule, e.g., antibody or antigen binding fragment thereof of the present invention or of a binding molecule having substantially the same binding specificities of any one thereof, the polynucleotide, the vector or the cell of the present invention for the preparation of a pharmaceutical or diagnostic composition for treating or preventing the progression of Alzheimer's disease; for the amelioration of symptoms associated with Alzheimer's disease; for diagnosing or screening a subject for the presence of Alzheimer's disease or for determining a subject's risk for developing Alzheimer's disease. Said pharmaceutical composition can be designed to be administered intravenously, intramuscularly, subcutaneously, intraperitoneally, intranasally, parenterally or as an aerosol; see also infra.

Hence, in one embodiment the present invention relates to a method of treating a neurological disorder characterized by abnormal accumulation and/or deposition of a protein in the central nervous system, which method comprises administering to a subject in need thereof a therapeutically effective amount of any one of the afore-described binding molecules, antibodies, antigens, polynucleotides, vectors or cells of the instant invention. The term "neurological disorder" includes but is not limited to Alzheimer's Disease, mild cognitive impairment, fronto-temporal dementia, Lewy-body disease, Parkinson's disease, Pick's disease, Binswanger's disease; congophilic amyloid angiopathy, cerebral amyloid angiopathy, Down's syndrome, multi-infarct dementia, Huntington's Disease, Creutzfeldt-Jakob Disease, AIDS dementia complex, depression, anxiety disorder, phobia, Bell's Palsy, epilepsy, encephalitis, multiple sclerosis; neuromuscular disorders, neurooncological disorders, brain tumors, neurovascular disorders including stroke, neuroimmunological disorders, neurootological disease, neurotrauma including spinal cord injury, pain including neuropathic pain, pediatric neurological and neuropsychiatric disorders, sleep disorders, Tourette syndrome, mild cognitive impairment, vascular dementia, multi-infarct dementia, cystic fibrosis, Gaucher's disease other movement disorders and disease of the central nervous system (CNS) in general. Unless stated otherwise, the terms neurodegenerative, neurological or neuropsychiatric are used interchangeably herein.

In the sense of the present invention, a method is disclosed for characterizing human antibodies for a large number of diseases and to also produce said antibodies subsequently in order to employ them diagnostically, therapeutically, or preventively in such patients whose immune system did not react with a corresponding immune response to the development of the pathology of the disease. In particular, this will have to be expected in diseases occurring at an advanced age because, as is known, the reactivity of the immune system continuously and significantly decreases as the age increases. In these cases, therapeutically or preventively active antibodies could compensate the age-related restrictions of the immune system with respect to blocking the enrichment of endogenous pathophysiological protein variants and could thus contribute to a better state of health at an advanced age. Thus, the medical uses of the present invention are particularly applicable for the above-described patient group, for example at the age of 60, 65, 70, 75, 80 or older and in principle concern all diseases manifesting themselves in form of derailment of any kind, like for example endoproteolysis, conformation alterations, alterations of the post-translational modifications, somatic mutations, or combinations thereof, phenotypically by means of developing pathophysiological variants of endogenous protein.

In the sense of the present invention, pathophysiological variants are considered to be variants containing pathological neoepitopes that deviate from the physiology, see supra. In particular, the therapeutic applications include tumor diseases, inflammatory diseases and diseases of the central nervous system, like Alzheimer's disease, Parkinson's disease, Pick's disease, Dementia with Lewy Bodies, Prion diseases including Creutzfeldt-Jakob disease, progressive supranuclear palsy, multiple system atrophy, corticobasal degeneration, frontotemporal degeneration with Parkinsonism liked to chromosome 17 Huntington's disease, frontotemporal dementia, cerebral amyloid angiopathy, mild cognitive impairment, Down's syndrome, hereditary cerebral hemorrhage with amyloidosis Dutch type and Icelandic type, spinocerebellar ataxia and amyotrohic lateral sclerosis as well as glaucoma, inclusion body myositis, familial amyloid polyneuropathy and amyloidoses comprising fibrillary proteins derived from at least one of the following precursor proteins SAA (Serum-Amyloid-Protein A), AL (k or l-light chains of Immunoglobulins), AH (gl Ig-heavy chains), ATTR (Transthyretin, Serum-Prealbumin), AApo-A-1 (Apolipoprotein A1), AApoA2 (Apolipoprotein A2), AGel (Gelsolin), ACys (Cystatin C), ALys (Lysozyme), AFib (Fibrinogen), Beta-amyloid (Amyloid precursor protein), Beta-amyloid2M (beta2-microglobulin), APrP (Prion protein), ACal (Procalcitonin), AIAPP (islet amyloid polypeptide); APro (Prolactin), AIns (Insulin); AMed (Lactadherin); Aker (Kerato-epithelin); ALac (Lactoferrin), Abri (AbriPP), ADan (ADanPP); or AANP (Atrial natriuretical peptide), (Skovronsky at al., Annu. Rev. Pathol. Mech. Dis. 2006; 1:151-70; Buxbaum, Curr Opin Rheumatol 2003; 16: 67-75.

A particular advantage of the therapeutic approach of the present invention lies in the fact that antibodies derived from B cells or B memory cells from a healthy preclinical or clinically unusually stable organism are, with a certain probability, capable of preventing a clinically manifest disease, or of diminishing the risk of the occurrence of a clinically manifest disease, or of delaying the moment of the occurrence of a clinically manifest disease. Typically, such antibodies also have already successfully gone through somatic maturation, i.e. the optimization with respect to selectivity and effectiveness in the high affinity binding to the target molecule by means of somatic variation of the variable regions of the antibody.

The knowledge that such cells in vivo, e.g. in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical development of the prophylactic or therapeutic antibody in at least one human subject. It can thus be expected that, with a procedure according to the present invention, both the target structure-specific efficiency of an antibody as therapeutic agent and its decreased probability of side effects significantly increase its clinical probability of success.

From the foregoing, it is evident that the present invention encompasses any use of a disease specific binding molecule comprising at least one CDR of the above described antibody, in particular for diagnosing and/or treatment of a disorder related to Alzheimer's disease and Abeta deposition, respectively. Preferably, said binding molecule is an antibody of the present invention or an immunoglobulin chain thereof. In addition, the present invention relates to anti-idiotypic antibodies of any one of the mentioned antibodies described hereinbefore. These are antibodies or other binding molecules which bind to the unique antigenic peptide sequence located on an antibody's variable region near the antigen binding site.

In another embodiment the present invention relates to a diagnostic composition comprising any one of the above described binding molecules, antibodies, antigen-binding fragments, polynucleotides, vectors or cells of the invention and optionally suitable means for detection such as reagents conventionally used in immuno or nucleic acid based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry and the Western blot assay. The antigens and antibodies of the invention can be bound to many different carriers and used to isolate cells specifically bound thereto. Examples of well known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the binding molecules, in particular antibodies of the present invention may also be used in a method for the diagnosis of a disorder in an individual by obtaining a body fluid sample from the tested individual which may be a blood sample, a lymph sample or any other body fluid sample and contacting the body fluid sample with an antibody of the instant invention under conditions enabling the formation of antibody-antigen complexes. The level of such complexes is then determined by methods known in the art, a level significantly higher than that formed in a control sample indicating the disease in the tested individual. In the same manner, the specific antigen bound by the antibodies of the invention may also be used. Thus, the present invention relates to an in vitro immunoassay comprising the binding molecule, e.g., antibody or antigen binding fragment thereof of the invention.

In this context, the present invention also relates to means specifically designed for this purpose. For example, a protein- or antibody-based array may be used, which is for example loaded with either antigens derived from the mentioned disorder-associated protein and containing the neoepitope in order to detect autoantibodies which may be present in patients suffering from, e.g., a neurological disorder, in particular Alzheimer's disease, or with antibodies or equivalent antigen-binding molecules of the present invention which specifically recognize any one of those proteins. For example, antigen microarray profiling of autoantibodies in rheumatoid arthritis has been reported by Hueber et al., Arthritis Rheum. 52 (2005), 2645-2655. Design of microarray immunoassays is summarized in Kusnezow et al., Mol. Cell Proteomics 5 (2006), 1681-1696. Accordingly, the present invention also relates to microarrays loaded with binding molecules or antigens identified in accordance with the present invention.

The present invention also provides a pharmaceutical and diagnostic, respectively, pack or kit comprising one or more containers filled with one or more of the above described ingredients, e.g. binding molecule, antibody or binding fragment thereof, antigen, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the present invention is of course particularly suitable for the diagnosis, prevention and treatment of a disorder which is accompanied with the presence of a disorder-associated protein as defined above, especially amyloidosis, and in particular applicable for the treatment of Alzheimer's disease (AD).

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, e.g. arresting its development; or (c) relieving the disease, e.g. causing regression of the disease.

Furthermore, the term "subject" or "patient" refers to a mammal, preferably a human, in need of treatment for a condition, disorder or disease.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal ad-ministration may be presented as a suppository with a suitable carrier.

Furthermore, whereas the present invention includes the now standard (though fortunately infrequent) procedure of drilling a small hole in the skull to administer a drug of the present invention, in a preferred aspect, the binding molecule, especially antibody or antibody based drug of the present invention can cross the blood-brain barrier, which allows for intravenous or oral administration.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as dopamine or psychopharmacologic drugs, depending on the intended use of the pharmaceutical composition. Furthermore, the pharmaceutical composition may also be formulated as a vaccine, for example, if the pharmaceutical composition of the invention comprises an anti-Aβ antibody for passive immunization.

In addition, co-administration or sequential administration of other agents may be desirable. A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Preferably, the therapeutic agent in the composition is present in an amount sufficient to restore normal behavior and/or cognitive properties in case of Alzheimer's disease.

The pharmaceutical compositions in accordance with the present invention can preferably be used for the treatment of neurological disorders including but not limited to Alzheimer's disease, Parkinson's disease, Pick's disease, Dementia with Lewy Bodies, Prion diseases including Creutzfeldt-Jakob disease, progressive supranuclear palsy, multiple system atrophy, corticobasal degeneration, frontotemporal degeneration with Parkinsonism liked to chromosome 17 Huntington's disease, frontotemporal dementia, cerebral amyloid angiopathy, mild cognitive impairment, Down's syndrome, hereditary cerebral hemorrhage with amyloidosis Dutch type and Icelandic type, spinocerebellar ataxia, amyotrohic lateral sclerosis, Bell's Palsy, epilepsy, encephalitis, neuromuscular disorders, glaucoma, inclusion body myositis, familial amyloid polyneuropathy, amyloidoses comprising fibrillary proteins derived from at least one of the following precursor proteins SAA (Serum-Amyloid-Protein A), AL (k or l-light chains of Immunoglobulins), AH (g1 Ig-heavy chains), ATTR (Transthyretin, Serum-Prealbumin), AApo-A-1 (Apolipoprotein A1), AApoA2 (Apolipoprotein A2), AGel (Gelsolin), ACys (Cystatin C), ALys (Lysozyme), AFib (Fibrinogen), Beta-amyloid (Amyloid precursor protein), Beta-amyloid2M (beta2-microglobulin), APrP (Prion protein), ACal (Procalcitonin), AIAPP (islet amyloid polypeptide); APro (Prolactin), AIns (Insulin); AMed (Lactadherin); Aker (Kerato-epithelin); ALac (Lactoferrin), Abri (AbriPP), ADan (ADanPP); or AANP (Atrial natriuretical peptide), (Skovronsky at al., Annu. Rev. Pathol. Mech. Dis. 2006; 1:151-70; Buxbaum, Curr Opin Rheumatol 2003; 16: 67-75, neuro-oncology, neuro-immunology, neuro-otology pain, pediatric neurology, phobia, affective disorders, sleep disorders, Tourette Syndrome, other movement disorders and disease of the central nervous system (CNS) in general.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. Detailed descriptions of conventional methods, such as those employed herein can be found in the cited literature; see also "The Merck Manual of Diagnosis and Therapy" Seventeenth Ed. ed by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art. For further elaboration of general techniques useful in the practice of this invention, the practitioner can refer to standard textbooks and reviews in cell biology and tissue culture; see also the references cited in the examples. General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Protein Methods (Bollag et al., John Wiley & Sons 1996); Non-viral Vectors for Gene Therapy (Wagner et al. eds., Academic Press 1999); Viral Vectors (Kaplitt & Loewy eds., Academic Press 1995); Immunology Methods Manual (Lefkovits ed., Academic Press 1997); and Cell and Tissue Culture: Laboratory Procedures in Biotechnology (Doyle & Griffiths, John Wiley & Sons 1998). Reagents, cloning vectors and kits for genetic manipulation referred to in this disclosure are available from commercial vendors such as BioRad, Stratagene, Invitrogen, Sigma-Aldrich, and ClonTech.General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11 (2001), 98-107.

The following experiments are illustrated and described with respect to antibody NI-101.11. However, the other antibodies of the NI 101 series, in particular NI 101.10 are structurally similar and thus may be expected to provide comparable results.

Supplementary Methods

Memory B Cell Display

Clinically carefully selected human subjects who are characterized by unusually positive clinical courses, e.g. absence of clinical signs of disease in the presence of risk factors, or stable courses of mild or prodromal signs with no disease development, or long-term non-progressors are recruited to provide peripheral blood lymphocytes as the starting material for the isolation of memory B cells. The strategy is based upon the concept established in infection immunology that a subject's memory B cell pool preserves the antibody specificities and possibly also antibody frequencies generated during previous antigen encounters (McHeyzer-Williams and Ahmed Curr. Opin. Immunol. 11 (1999), 172-179; Bernasconi et al., Science 298 (2002), 2199-202; Traggiai et al., Nat. Med. 10 (2004), 871-875). This concept was developed to explain adaptive immunity against infectious agents, as well as for the description of antibody-mediated immunity following a primary infection. According to this theory, the entire complement of antibodies against all antigens that had had induced an antibody response in the subject's history, either naturally or upon vaccination, should be fully represented within the memory B cell pool. In accordance with the present invention this theory is applied to endogenous antigens generated as a result of abnormal aggregation or conformation of an otherwise physiological relevant protein, and that, as such, is not subject to the physiological immunologic tolerance, and, thus, can acquire antigenic properties and induce an immune response against the conformational neo-epitopes (neoepitopes).

Memory B cells are isolated with surface markers including the pan B cell marker CD22, combined with negative selection of antigen-inexperienced B cells that expressed IgM, IgD, IgE, and IgA. With this technique, approximately 10.000 to 150.000 memory B cells can be obtained from 30 ml of human blood. These are immortalized, for example with Epstein Barr Virus, and cultured oligo-clonally on irradiated human fibroblast feeder layers (Zubler et al., J Immunol. 134 (1985), 3662-3668; Traggiai et al., Nat. Med. 10 (2004), 871-875). To improve transformation and immortalization efficacy of antibody-secreting memory B cells, CpG 2006 which mimics the activities of bacterial un-methylated CpG-dinucleotides (Hartmann and Krieg J Immunol 164(2) (2000), 944-953) can be used.

Experimental Protocol:

Selection of B cells from the bulk of PBL was performed using the MACS technology and CD22 microbeads (Miltenyi, Bergisch Gladbach, Germany). PBL were labeled with MACS anti human CD22, phycoerythrin-conjugated anti human IgD and APC-conjugated antibodies anti human IgM, IgA, CD3, CD8, CD56 (Becton Dickinson, Basel, Switzerland). CD22-positive cells were isolated using LS columns and the Midi MACS device (Miltenyi) followed by selection of phycoerythrin- and APC-negative cells using a MoFlo cell sorter (Dako, Fort Collins, USA). CD22-positive, IgM-, IgD-, IgA-, and IgE-negative B cells were then incubated with Epstein Barr Virus containing supernatant obtained from B95-8 cells and CpG 2006 (Sigma, Buchs, Switzerland) at a concentration of 2.5 mg/l in B cell medium (RPMI 1640 supplemented with 10% fetal calf serum (Hyclone, Perbio, Lausanne, Switzerland). 5-50 cells were seeded per well in Costar round bottom 96 well plates (Corning, Vitaris, Baar, Switzerland) in B cell medium on 30.000 irradiated human PBL prepared from voluntary donors. Memory B cell cultures were maintained at 37° C. and 5% $CO_2$ in a humidified cell culture incubator for 2-4 weeks after which time the conditioned medium of the cultures was assayed in ELISA and on tissue arrays.

Antibody Screening

Antibodies in conditioned media are screened for binding to pathological epitopes including protein aggregates and abnormal, pathologically relevant structures on tissue sections obtained from human patients with pathologically confirmed diagnoses including, but not restricted to, Alzheimer's disease, or obtained from tissue sections of transgenic mouse models of human disease, or from tissue sections obtained from animal models of human disease including aged non-human primates, or by ELISA of aggregated synthetic peptide preparations. Abnormal, pathologic structures in the sense of this invention include, but are not restricted to, β-amyloid plaques, neurofibrillary tangles, alpha-synuclein aggregates in Lewy bodies, and protein aggregates deposited in dystrophic neurites. Human tissues are also used to exclude cross-reactivities of antibodies with normal cellular or supercellular tissue structures. Selected antibodies are further analyzed for class and light chain subclass determination. Selected pathology-relevant antibody messages from memory B cell cultures are transcribed by using RT-PCR, cloned and combined into expression vectors for recombinant production.

Experimental Protocol:

Screening of B cell conditioned medium using microtiter-compatible tissue microarrays.

Array Production

Paraffin-embedded human post-mortem Alzheimer's disease brain tissues were cut into rods of 1-2 mm in diameter and 10 mm in length. Four rods were embedded vertically in paraffin to form a square fitting the microtiter format of 9 by 9 mm. 5 μm tissue slices were cut from this assembly with a microtome and two slices were mounted adjacent to each other onto glass slides resulting in an assembly of 2 by 4 rods that fit the 96-well microtiter format. Alternatively, tissues from APP transgenic mice were used to prepare the tissue arrays.

B Cell Screening

Conditioned medium from memory B cell cultures was transferred onto the tissue array slides using a multichannel pipette and incubated for 2 h at room temperature. After a washing step the binding of human antibodies to tissue sections was analyzed using Cy 3-conjugated secondary antibodies to human IgG (Jackson ImmunoResearch Europe Ltd., Suffolk, UK). Analysis of fluorescence was performed on an inverted fluorescence microscope (Leica, Heerbrugg, Switzerland).

ELISA 96 well half area Microplates (Corning) were coated with synthetic Abeta-peptide at a standard concentration of 1 μg/ml in coating buffer (15 mM $Na_2CO_3$, 35 mM $NaHCO_3$, pH 9.42) overnight at 4° C. Plates were washed and non-specific binding sites were blocked for 1 h at RT with PBS containing 2% BSA (Sigma, Buchs, Switzerland). B cell conditioned medium was transferred from memory B cell culture plates to ELISA plates and was incubated for 2 h at room temperature. Binding of human antibodies was determined using horse radish peroxidase (HRP)-conjugated donkey anti-human IgG polyclonal antibodies (Jackson ImmunoResearch Europe Ltd., Cambridgeshire, UK) followed by measurement of HRP activity in a standard colorimetric assay.

Molecular Cloning of Antibodies Displaying Specificity of Interest

Living B cells of selected memory B cell cultures are harvested using a cell sorter. mRNA is prepared and immunoglobulin heavy and light chain sequences are obtained using Ig-framework specific primers for all human variable heavy and light chain framework 1 (FR1) families as 5' primers in combination with primers specific for all human J-H segments as 3' primers (Marks et al., Mol. Biol. 222 (1991), 581-597). Alternatively, single-cell RT-PCR of single sorted cells from the memory B cell culture can be used as source of Ig heavy and light chain sequences (Babcook et al., Proc. Natl. Acad. Sci. USA 93 (1996), 7843-7848; Brezinschek et al., J. Immunol. 155 (1995), 190-202; Coronella et al., Nucleic Acids Research 28 (2000); Owens, et al., J. Immunol. 171 (2003), 2725-2733). Single cell sorting preserves the correct pairing of the immunoglobulin heavy and light chains of the antibody clones originally produced in the B cell culture.

Identification of the antibody clone with the desired specificity is performed by re-screening on microtiter compatible tissue microarray and ELISA upon recombinant expression of complete antibodies. Recombinant expression of complete IgG1 antibodies is achieved upon insertion of the variable heavy and light chain sequences "in the correct reading frame" into expression vectors that complement the variable region sequence with a sequence encoding a signal peptide at the 5-prime end and at the 3'-end with a sequence encoding the appropriate constant domain(s). To that end the primers contained restriction sites designed to facilitate cloning of the variable heavy and light chain sequences into antibody expression vectors. Heavy chain immunoglobulin are expressed by inserting the immunoglobulin heavy chain RT-PCR product in frame into a heavy chain expression vector bearing a signal peptide and the constant domains of human immunoglobulin. Kappa light chain immunoglobulin is expressed by inserting the kappa light chain RT-PCR-product in frame into a light chain expression vector providing a signal peptide and the constant domain 1 of human kappa light chain immunoglobulin. Alternatively, lambda light chain immunoglobulin is expressed by inserting the lambda light chain RT-PCR-product in frame into a lambda light chain expression vector providing a signal peptide and the constant domain 1 of human lambda light chain immunoglobulin.

Functional recombinant monoclonal antibodies are obtained upon co-transfection into HEK 293 cells (or any other appropriate recipient cell line) of a Ig-heavy-chain expression vector and a kappa or lambda Ig-light-chain expression vector. Recombinant human monoclonal antibody is subsequently purified from the conditioned medium using a standard Protein A column purification. Recombinant human monoclonal antibody can be produced in unlimited quantities using either transiently or stably transfected cells. Cell lines producing recombinant human monoclonal antibody can be established either by using the Ig-expression vectors directly or by re-cloning of Ig-variable regions into different expression vectors. Derivatives such as F(ab), F(ab)$_2$ and scFv can also be generated from these Ig-variable regions.

Experimental Protocol:
RT-PCR of Bulk B Cells

Living cells as identified by their forward- and sideward light scattering properties of selected memory B cell cultures were sorted in aliquots of 100-2000 cells directly in 0.2 ml PCR tubes filled with 20 µl of RNAlater (Ambion, Huntingdon, UK) using a MoFlo cell sorter. mRNA was prepared using the mRNA-Direct Micro Kit (Dynal, Invitrogen, Basel, Switzerland). cDNA was prepared using the "RT for PCR" Kit (Clontech BectonDickinson, Basel, Switzerland) and PCR of immunoglobulin (Ig) heavy and light chain variable sequences was performed using the Advantage 2 PCR Kit (Clontech) using specific primers for all human variable heavy and light chain frame work 1 (FR1) families as 5' primers in combination with primers specific for the constant domains of human Ig heavy or Ig kappa or Ig lambda light chains as 3' primers. Primers were purchased from Microsynth (Balgach, Switzerland).

A signal peptide that was used in all expression vectors was derived from the human immunoglobulin kappa light chain family 1 L5 sequence (MDMRVPAQLLGLLLLWF-PGSRC; SEQ ID NO: 2) as described at V-Base and designed to provide the restriction site Xba 1 in order to facilitate the cloning of PCR amplified variable regions (ATGGACATGCGGGTGCCCGCCCAGCTGCTGGGCCTGCTGCTGCTGTGG
TTCCCCGGC<u>TCTAGA</u>TGC;

SEQ ID NO: 1). XbaI was introduced by silent mutagenesis. As a 3' restriction site used for the cloning of variable heavy chain regions the restriction site SalI was introduced into C1 of IgG1 provided by the vector. Similarly, the restriction site BsiW1 was introduced into C1 of the kappa light chain and XhoI was introduced into C1 of lambda light chain. Restriction digest of PCR products and ligation into to recipient vectors was performed according to standard procedures. Plasmid DNA was prepared using standard kits (Quiagen, Hombrechtikon, Switzerland). Recipient vectors contained a CMV promoter for the expression of antibody genes in mammalian cells.

Single Cell RT-PCR

For single cell RT-PCR of Ig heavy and light chain variable regions from cultured B cells a modification of the method described by Owens et al. was used (Owens et al., 2003). Single cells were deposited directly into each tube of an array of 0.2 ml PCR tubes using the MoFlo cell sorter. Each tube was prepared to contain 10 µl of RT buffer for Superscript II reverse transcriptase (Invitrogen). PCR tubes were shock frozen on dry ice and thawed immediately prior to RT-PCR. cDNA was prepared using random hexamers (Clontech) and Superscript II reverse transcriptase (Invitrogen). 1 round PCR of immunoglobulin heavy and light chain variable regions was performed using, as 5' primers, a set of primers that primed in all signal peptides conserved among Ig-variable region families. At the 3' position, single primers specific for the constant region of Ig C1 heavy chain or the Ig kappa- or Ig lambda light chain were used. 2nd round PCR was performed on PCR-products obtained during first round PCR using the primers as described for the bulk B cell RT-PCR. Cloning into recipient vectors was performed accordingly.

Alternative Cellular Cloning

Cloning was performed using the standard limited dilution method or by single cell deposition into 96 well culture plates using a cell sorter (MoFlo, Dako, Fort Collins, USA). For limiting dilution, cells of a memory B cell culture were harvested, passed through a 30 µm nylon mesh (Falcon, Becton Dickinson, Basel, Switzerland) resuspended in medium and seeded onto 96 well plates or 384 well plates at a concentration of 0.3 cells per well.

For seeding with the cell sorter, the device was set to deposit one single cell (single 1 mode) per well directly in 96 well plates supplemented with B cell medium. The culture medium was supplemented with medium conditioned by activated T cells. Alternatively, 30.000 irradiated feeder cells were added to the medium.

Sequence Analysis of Immunoglobulin Variable Region Sequences

Sequencing of cloned immunoglobulin variable region sequences was performed using primers specific for the CMV promoter present 5' of the inserted Ig variable region sequences in the expression vector. Alternatively, primers that primed in the constant domains of Ig heavy- and light chains were used. Sequences obtained were analyzed and aligned using Vector NTI software (Informax-Invitrogen). Plasmids containing sequences that encoded complete immunoglobulin variable regions in frame with the leader peptide and the constant domain were used for expression.

Expression of Functional Recombinant Monoclonal Antibodies

The antibodies can be produced in sufficient quantities by recombinant expression using technologies known in the art (Trill et al., Curr. Opin. Biotechnol. 6 (1995), 553-601). Recombinant human monoclonal antibody of up to 1 mg was produced upon transient transfection of 293 HEK cells. Recombinant human monoclonal antibody of up to 100 mg was produced upon stable transduction of 293 HEK cells or the murine NSO cells using recombinant lentivirus vectors.

Small Scale Production of Human Recombinant Antibody by Transient Transfection

Ig-heavy chain vector and Ig-light chain vectors were co-transfected into HEK 293 cells using the standard calcium phosphate co-precipitation method. Recombinant antibodies were purified from the medium conditioned by transfected HEK 293 cells using protein A column purification (GE-Healthcare, Otelfingen, Switzerland).

Large Scale Production of Human Recombinant Antibody by Stable Transduction

Here, a lentivirus-based transfection system was employed to generate stably transduced cell lines producing human recombinant antibody (Zufferey et al., J. Virol. 72 (1998), 9873-9880). HEK 293 cells were co-transduced with two distinct lentivectors one bearing an expression cassette for the Ig heavy chain, the other a cassette for the Ig light chain of a recombinant antibody. This method of transduction can be used in a broad range of mammalian cell lines such as CHO and NSO cells.

Validation in Transgenic Mouse Models of Human Disease

Transgenic mice were generated as previously described (Knobloch et al., Neurobiol. Aging July 28 (2006)) on a hybrid background of C57Bl/6 and DBA2. The test group was backcrossed once to C57Bl/6. Mice were kept under standard housing conditions on a reversed 12 h:12 h light/dark cycle and had free access to food and water. The treatment groups were balanced for age (24 months at first testing, 26 months at 2 testing) and gender. Mice are treated with antibodies (3 mg/kg body weight) by once weekly intraperitoneal injections over a time period of 2 months resulting in 8 injections per animal.

Behavioral Testing in the Y-Maze

The spontaneous alternation rate is assessed using a Y-shaped plastic maze, with 40×20×10 cm arm sizes. During 5 min sessions, the sequences of arm entries are recorded; alternation was defined as successive entries into the three arms, in overlapping triplet sets. The percent alternation was calculated as the ratio of actual to possible alternations. After 2 months of antibody treatment, the mice are retested in the Y-maze. The experimenters are always kept blind for both treatments and genotypes during the whole experiment.

Blood-Brain Barrier Penetration and Binding to Abnormal Structures in the Brain

To assess whether the selected antibodies or fragments thereof can penetrate the blood-brain barrier and bind to their abnormally aggregated or conformationally altered protein targets in the brain, an effective dose of the antibody is administered systemically, intraperitoneally, intravenously, intramuscularly, subcutaneously or intranasally to a transgenic animal that is characterized by unphysiological accumulation of the aggregated or conformationally altered protein target in the brain. Binding of the antibody to the pathology specific structures in the brain is then evaluated by immunostaining with a labeled anti-human Ig secondary antibody followed by standard immunohistochemical detection.

Experimental Protocol:

PS-1/APPswe transgenic model mice for Alzheimer's disease received two peripheral injections of 150 µg NI-101.11 at day 1 and day 3. The mice were sacrificed 24 h after the second injection and perfused with PBS. Brains were frozen and tissue slices were prepared from frozen tissue using a cryotome. Presence of human antibody on cryostat sections was assayed by staining with Cy3-labeled anti human IgG antibody (Jackson ImmunoResearch Europe, Suffolk, UK). Localization of amyloid plaques was performed by co-staining the cryostat sections with the murine Abeta-specific control antibody 6E10 (available from Covance, Catalog Number SIG-39320) followed by FITC-labeled anti mouse IgG antibody. Alternatively, staining with Cy3-labeled anti human IgG antibody was used alone. Analysis of fluorescence was performed on an inverted fluorescence microscope (Leica).

Reduction of Brain Pathology

The effects of antibody treatment on the levels of aggregated or conformationally altered protein targets in the brain is assessed by systemic treatment or targeted brain delivery of the antibody (intracranial, intrathecal or intraventricular) and an unrelated antibody control to transgenic animals with characteristic unphysiological accumulation of the aggregated or conformationally altered protein target in the brain. The treatment effects is evaluated by immunostaining or histochemical staining of the altered or aggregated protein targets and measuring the area covered by such aggregates, aggregate size and aggregate number and biochemical quantification of the concentrations of the protein targets in different brain areas.

Absence of Antibody-Treatment Related Side Effects

Potential target related adverse effects of the antibody-treatment will be assessed by systemic administration or targeted brain delivery of the antibody (intracrainial, intrathecal or intraventricular) and an unrelated antibody control to transgenic animals with characteristic unphysiological accumulation of the aggregated or conformationally altered protein target in the brain. Potential side effects will be evaluated by immunostaining or histochemical staining (e.g. Prussian blue for micorhemorrhages, hematoxilin-eosin, activated white blood cells) and biochemical quantification (e.g. cytokine levels by ELISA).

Immunofluorescence Staining of Living Cells

HEK 293 cells were transiently transfected with a vector that expresses human wild type APP fused at the intracellular C-terminus to the yellow fluorescent protein variant Citrine. 24 hours after transfection the cells were incubated with human recombinant antibodies or control antibodies at 4° C. for 30 minutes. After a washing step the cell were fixed and surface-bound antibody was detected using Cy-3-labeled secondary antibodies to human or mouse IgG (Jackson ImmunoResearch). Analysis of fluorescence was performed on a confocal microscope (Leica).

Preparation of Abeta Fibrils

Abeta peptide was purchased from Bachem (Bubendorf, Switzerland). Lyophylised peptide was reconstituted in TFA and resuspended in PBS immediately prior to its use as monomeric Abeta in the assays. Abeta fibrils were prepared by incubation of monomeric Abeta1-42 peptide at a concentration of 100 µg/ml in PBS at 37° C. for 24 h. Monomeric Abeta peptide and fibril preparations were also used as substrate to coat ELISA plates.

Western Blotting

Monomeric Abeta peptide was mixed with loading dye, heat denatured and 0.2 µg was loaded per lane and separated on a gradient SDS-PAGE. Blots were incubated with primary antibody for 2 h. Binding of primary human monoclonal antibody or mouse control antibody 6E10 was revealed using secondary anti human or anti mouse antibodies conjugated with horse radish peroxidase (HRP). Blots were developed using SuperSignal West Femto Maximum Sensitivity Substrate (Pierce, Fisher Scientific, Wohlen, Switzerland).

Competition of Tissue Amyloid Plaque Binding

Recombinant human NI-101.11 antibody was incubated for 2 h with Abeta peptide preparations. The antibody/Abeta preparations were then used for immunohistochemical staining of brain section obtained from a patient with neuropathologically confirmed Alzheimer's disease. 5 µm cryosections were prepared, blocked with 4% BSA, 5% goat serum and 5% horse serum in PBS for 1 h at RT and stained with NI-101.11/Abeta preparations for 1 h at room temperature. After a washing step the binding of human antibodies to tissue sections was analyzed using Cy3-conjugated secondary antibodies to human IgG (Jackson ImmunoResearch Europe Ltd). Analysis of fluorescence was performed on an inverted fluorescence microscope (Leica, Heerbrugg, Switzerland).

Example 1

Figure 1B:
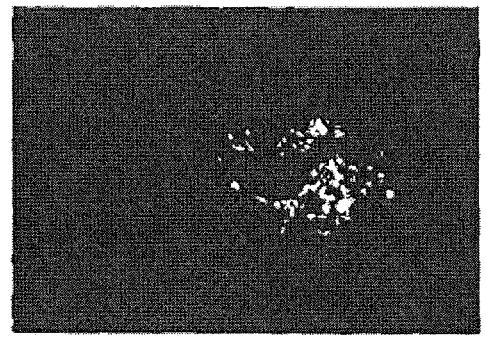
FIG. 1B: provides control staining with known antibody against human beta-amyloid.
Figure 2A:
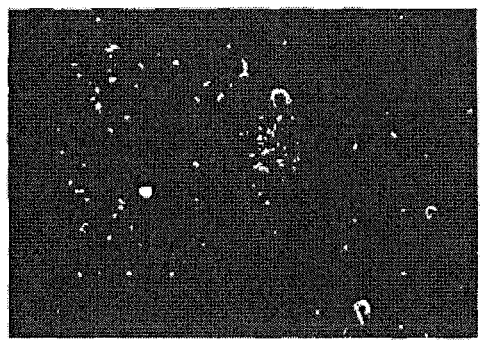
FIG. 2A: provides the results of immunohistochemical staining with human antibodies against neurofibrillary tangles. Healthy human subjects contain antibodies to neurofibrillary tangles. Immunohistochemical staining with antibodies from healthy subjects on brain sections obtained from patients with pathologically confirmed Alzheimer's disease reveals antibodies that bind to neurofibrillary tangles confirmed by a known antibody against human tau.
Figure 2B:
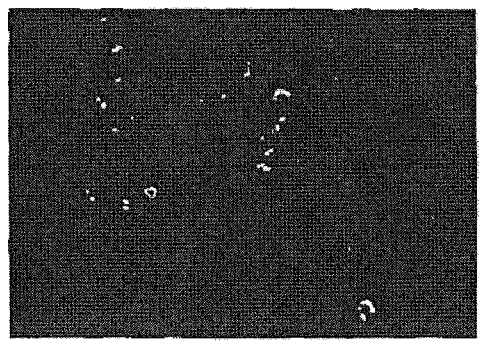
FIG. 2B: provides control staining with known antibody against human tau.
Figure 3A:
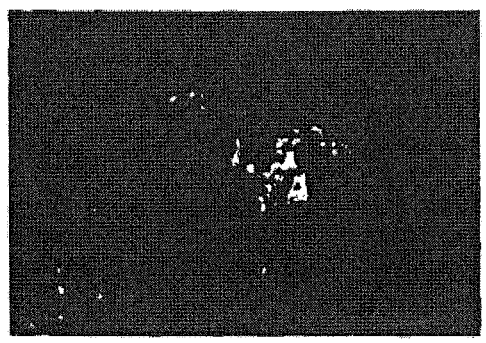
FIG. 3A: provides the results of immunohistochemical staining with human antibodies against dystrophic neurites. Healthy human subjects contain antibodies to dystrophic neurites. Immunohistochemical staining with antibodies from healthy subjects on brain sections obtained from patients with pathologically confirmed Alzheimer's disease reveals antibodies that bind to dystrophic neurites.
Figure 3B:
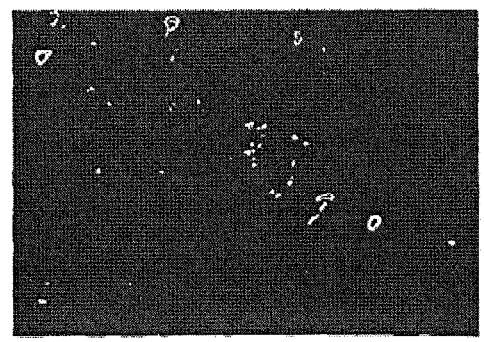
FIG. 3B: provides control staining with known antibody against human tau.

Detection of Human Antibodies Against Abnormal Structures Prevalent in Human Brain Diseases Antibodies from phenotypically healthy subjects, or clinically unusually stable patients with Alzheimer's disease were tested by immunohistochemistry on brain sections obtained from patients with pathologically confirmed Alzheimer's disease. FIG. 1A demonstrates the presence of antibodies in a clinically unusually stable patient that bind to beta-amyloid plaques as was confirmed by co-staining with a known antibody against human beta-amyloid (antibody 4G8; FIG. 1B). The presence in a healthy human subject of antibodies to neurofibrillary tangles in a tissue section obtained from a patient with Alzheimer's disease is shown in FIG. 2A. This result was confirmed by co-staining with a known antibody against human tau (HT7). FIG. 3A reveals the presence in a healthy human subject of antibodies against dystrophic neurites in a tissue section obtained from a patient with Alzheimer's disease. Control staining with known antibody against human tau (HT7) is depicted in FIG. 3B. These results demonstrate the presence in phenotypically healthy, or clinically unusually stable patients of antibodies against identifiable pathological structures in human tissue samples with histopathologically confirmed diagnoses.

Example 2

Recombinant Human Antibodies Maintain Specificity to Abnormal Structure In Vivo and Recognize Conformational Epitope of Disease-Associated Beta-Amyloid Protein in Brain Amyloid Plaques but Not the Physiological Precursor or Non-Pathogenic Derivative Thereof Antibodies NI-101.11, NI-101.12, NI-101.13A and NI-101.13B were obtained from clinically unusually stable Alzheimer's disease patients with a significantly reduced rate of cognitive decline. Antibody isolation and recombinant production was performed as specified in supplementary methods.

NI-101.11

Figure 4:
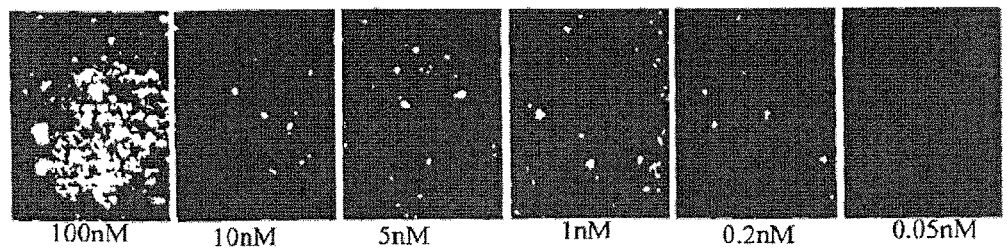
FIG. 4: Antibody against beta-amyloid. The figure shows specific binding of recombinant human NI-101.11 antibody that was isolated from a clinically unusually stable Alzheimer's disease patient to brain beta-amyloid plaques. Brain sections obtained from a patient with neuropathologically confirmed Alzheimer's disease were stained with recombinant human antibody at the indicated concentrations. Antibody binding to beta-amyloid plaques with concentrations of 50 pM suggest high affinity binding.
Figure 5:
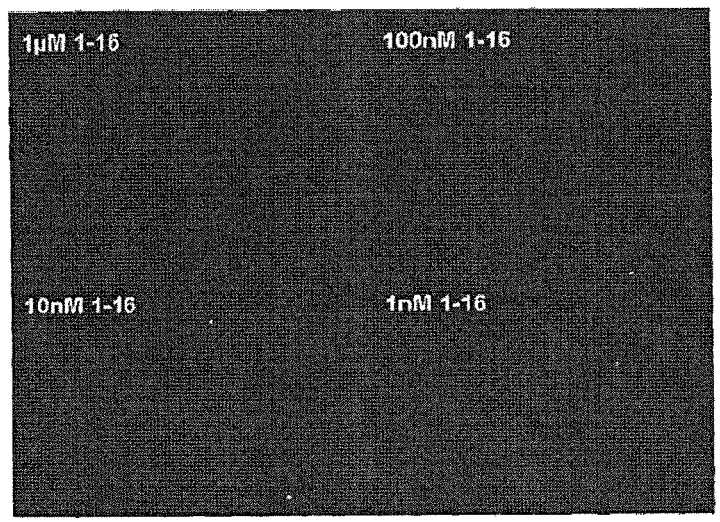
FIG. 5: Binding of recombinant human NI-101.11 antibody to beta-amyloid plaques is not competed by linear synthetic N-terminal Abeta polypeptides. Binding of the recombinant antibody against brain beta-amyloid (0.5 nM) cannot be competed by N-terminal Abeta-derived polypeptide representing positions 1 to 16 at concentrations up to 1 µM.
Figure 6:
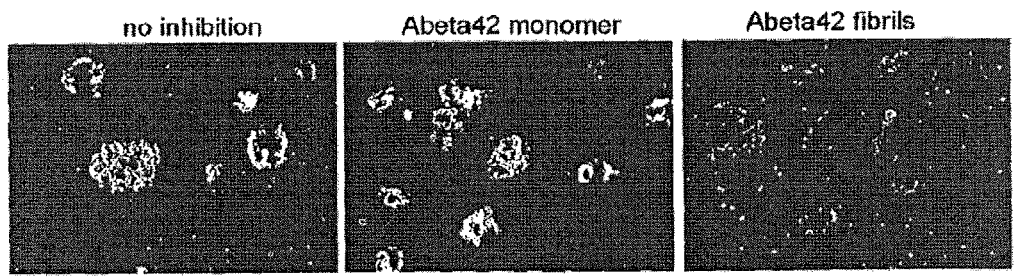
FIG. 6: Recombinant human NI-101.11 antibody recognizes a conformational Abeta epitope that is not present in monomeric Abeta. Binding of NI-101.11 to beta-amyloid plaques on brain sections can be competed by Abeta1-42 fibrils but not linear synthetic Abeta1-42 monomers.

Recombinant NI-101.11 was tested for binding to brain beta-amyloid plaques (FIG. 4). Brain sections obtained from a patient with neuropathologically confirmed Alzheimer's disease were stained at the indicated concentrations. Antibody binding to beta-amyloid plaques with concentrations of 50 pM suggest high affinity binding. The binding of antibody NI-101.11 to beta-amyloid plaques at a concentration of 0.5 nM cannot be competed by addition of excess amounts of linear synthetic N-terminal Abeta-derived polypeptide representing positions 1 to 16 at concentrations of up to 1 µM (FIG. 5). Furthermore, the binding of NI-101.11 to beta-amyloid plaques on brain sections at 8 nM concentration is competed by excess amounts Abeta1-42 fibrils (4 µM) but not of linear synthetic Abeta1-42 monomers at 4 µM concentration, suggesting that NI-101.11 recognizes a conformational epitope that is not present in monomeric Abeta (FIG. 6).

Figure 7:
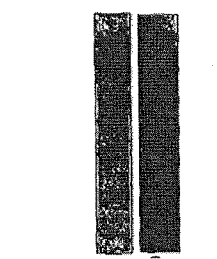
FIG. 7: Recombinant human NI-101.11 antibody does not bind to linear, monomeric synthetic Abeta on Western blots. Preparations of monomeric Abeta were separated by non-denaturing PAGE. Blotted protein was probed with human recombinant antibody against beta-amyloid and control antibodies against N-terminal linear Abeta sequences (6E10). No binding of NI-101.11 to monomeric Abeta was detected. This observation suggests that the antibody recognizes a conformational Abeta epitope.

To further assess binding of human recombinant NI-101.11 antibody to linear, monomeric synthetic Abeta, preparations of monomeric Abeta were separated by non-denaturing PAGE. Blotted protein was probed with human recombinant NI-101.11 antibody and a control antibody against N-terminal linear Abeta sequences (6E10). While 6E10 produced prominent staining of monomeric Abeta peptide, no binding was detected for human NI-101.11 suggesting that NI-101.11 does not bind to the linear monomeric Abeta peptide but recognizes a conformational Abeta epitope. (FIG. 7)

Figure 8:
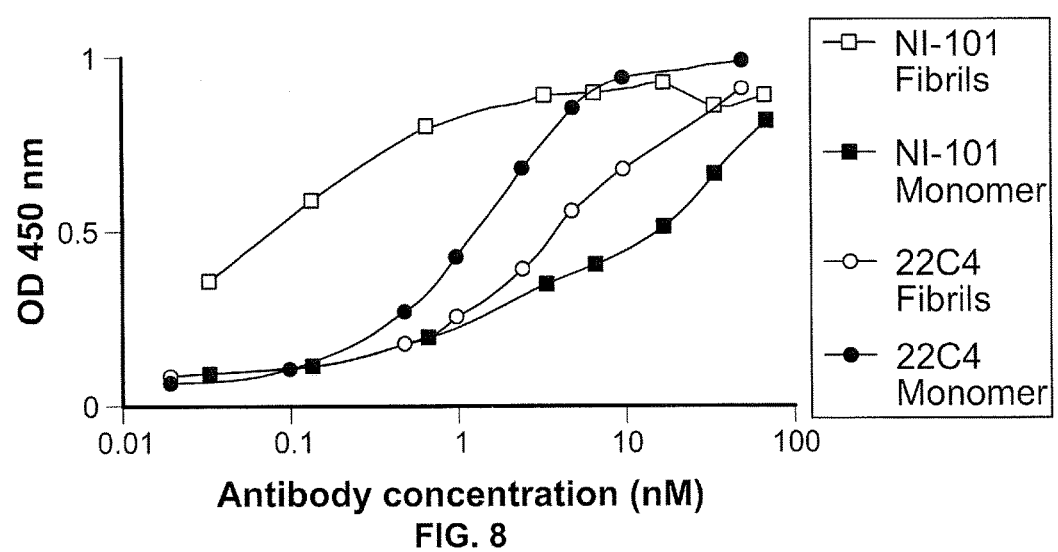
FIG. 8: Human NI-101.11 antibody binds artificial amyloid fibrils prepared from synthetic Abeta1-42 peptides. Synthetic Abeta fibrils or monomeric synthetic Abeta coated onto ELISA plates at equal coating densities were incubated with recombinant human antibodies against brain beta-amyloid at the indicated concentrations. Binding activity of human antibody against brain beta-amyloid to artificial amyloid fibrils (open squares) is more than 100 times higher as compared to monomeric Abeta (filled squares). Control antibody 22C4 preferentially binds to monomeric Abeta (filled circles), and less well to fibrils (open circles). This suggests that NI-101.11 recognizes a conformational epitope which is also present on artificial amyloid fibrils prepared from synthetic Abeta peptides.

The binding of recombinant NI-101.11 to artificial amyloid fibrils prepared from synthetic Abeta1-42 peptides and monomeric Abeta was determined by ELISA (FIG. 8). Synthetic Abeta fibrils or monomeric synthetic Abeta coated onto ELISA plates at equal coating densities were incubated with NI-101.11 at the indicated concentrations. Binding to artificial amyloid fibrils (open squares) is more than 100 times higher as compared to monomeric Abeta (filled squares). Control antibody 22C4 against the C-terminus of Abeta preferentially binds to monomeric Abeta (filled circles), and less well to fibrils (open circles). This suggests that NI-101-10 recognizes a conformational epitope which is also present on artificial amyloid fibrils prepared from synthetic Abeta peptides.

Figure 9:
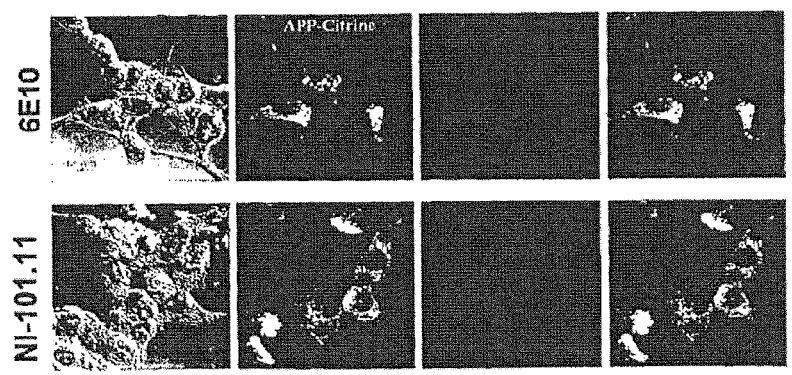
FIG. 9: Absent cross-reactivity of recombinant human NI-101.11 antibody to cellular full-length APP or with any of its physiological derivatives occurring in cultured cells. In contrast to the control antibody (6E10) that binds to cell-surface APP, binding of NI-101.11 to full-length APP present at cellular surfaces is absent. These data demonstrate absent cross-reactivity of NI-101.11 to physiological, cellular full-length APP.

Cross-reactivity of recombinant human NI-101.11 antibody against cellular full-length APP or with any of its physiological derivatives was determined by cell binding assays (FIG. 9).

Live HEK 293 cells stably expressing human APP fused to Citrin as a marker were incubated for 30 min at 4° C., to prevent internalization, with the recombinant human NI-101.11 antibody or the control antibody 6E10 against N-terminal linear Abeta sequence. Citrin-positive signals indicate APP-expressing cells. In contrast to the control antibody (6E10) that binds to cell-surface APP in all cells expressing the fusion construct, no binding of recombinant human NI-101.11 antibody to full-length APP is detected. These data demonstrate absent cross-reactivity of NI-101.11 to physiological, cellular APP.

The lack of binding of NI-101.11 to monomeric Abeta was further demonstrated by size exclusion chromatography: No binding of NI-101.11 or an unrelated control antibody was observed to monomeric FITC-labeled Abeta1-

Figure 10A:
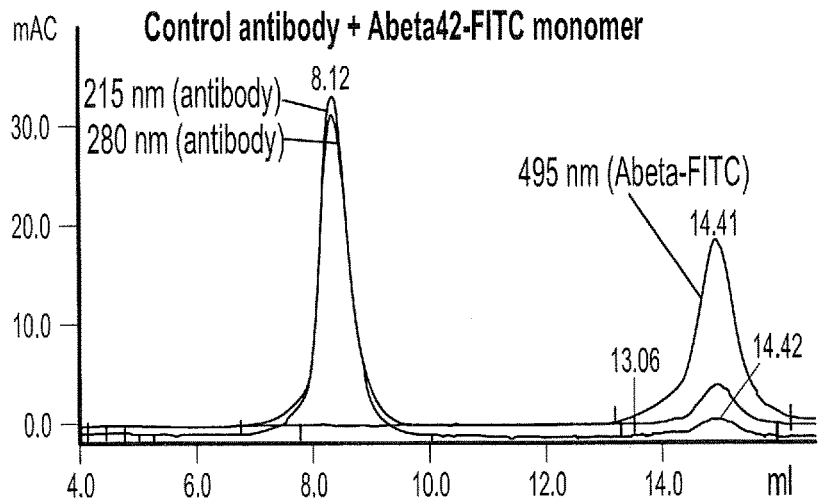
FIG. 10A: is an examination of binding of NI-101.11 to monomeric Abeta via size exclusion chromatography which shows no binding of NI-101.11 or an unrelated control antibody to monomeric FITC-labeled Abeta1-42.
Figure 10B:
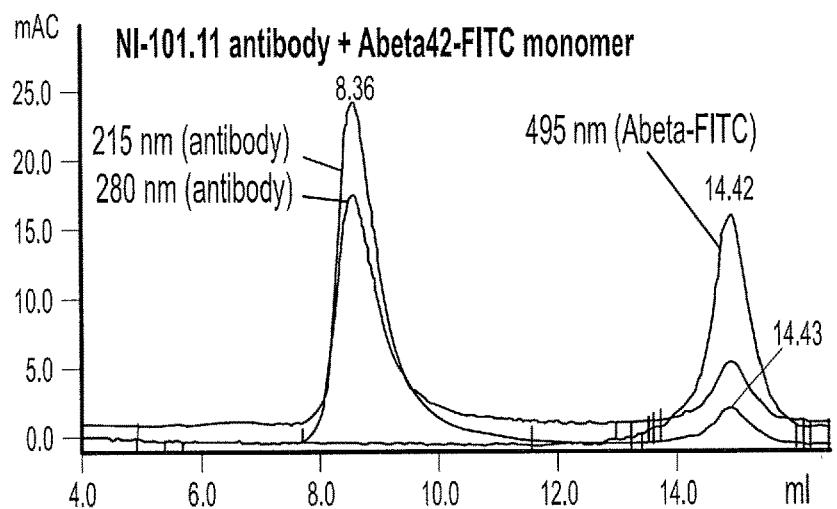
FIG. 10B: is an examination of binding of NI-101.11 to monomeric Abeta via size exclusion chromatography which shows no binding of NI-101.11 or an unrelated control antibody to monomeric FITC-labeled Abeta1-42.
Figure 10C:
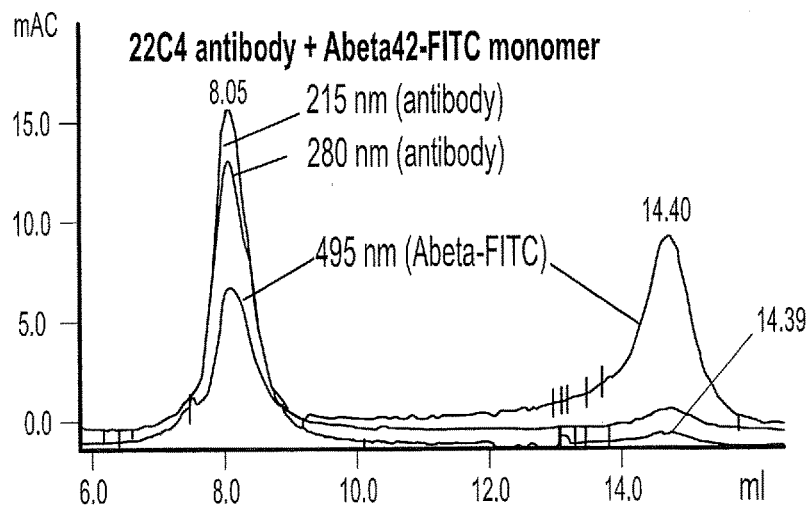
FIG. 10C: shows prominent binding of antibody 22C4 that recognizes a linear epitope present in the C-terminus of Abeta.

42 (FIG. 10A, 10B). In contrast, antibody 22C4 directed against a linear epitope present in the C-terminus of Abeta co-eluted with FITC-Abeta1-42 monomers (FIG. 10C).

Figure 11:
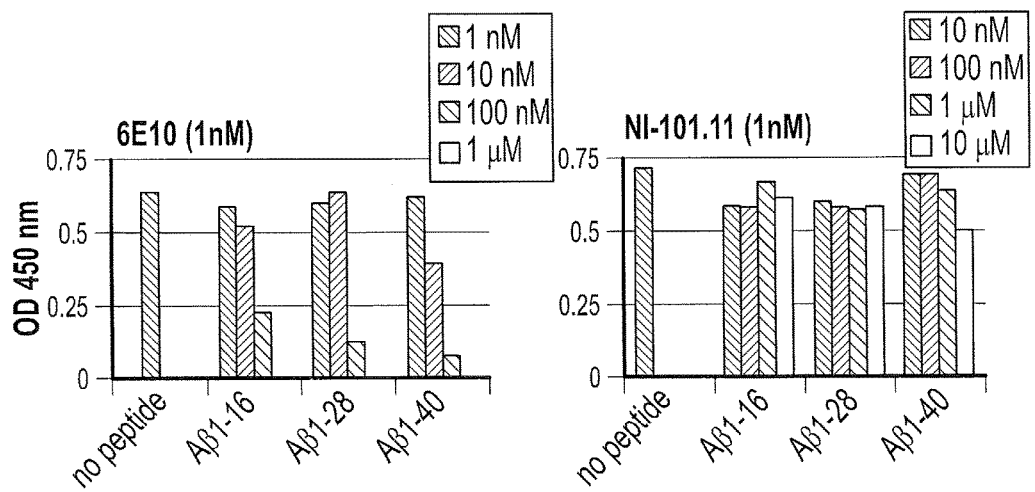
FIG. 11: Competition ELISA showing that binding of antibody 6E10, an antibody directed against a linear epitope at the N-terminus of Abeta could be completely blocked upon pre-incubation with excess concentrations of monomeric Abeta peptides while pre-incubation with excess concentrations of these monomeric Abeta peptide preparations did not abolish NI-101.11 binding.

In a competition ELISA, binding of 6E10, an antibody directed against a linear epitope at the N-terminus of Abeta, could be completely blocked upon pre-incubation with excess concentrations of monomeric Abeta1-16, Abeta1-28 and Abeta1-40 peptides. In contrast, pre-incubation with excess concentrations of linear Abeta peptides did not abolish NI-101.11 binding, suggesting that NI-101.11 requires a conformational epitope (FIG. 11).

NI-101.13A and 13B

Figure 12:
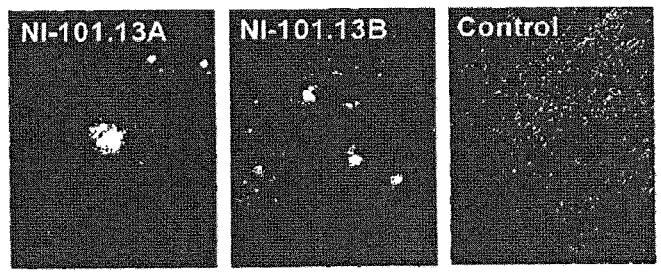
FIG. 12: Binding of NI-101.13A and NI-101.13B to brain sections obtained from Tg2676 transgenic mouse model of Alzheimer's disease.
Figure 13:
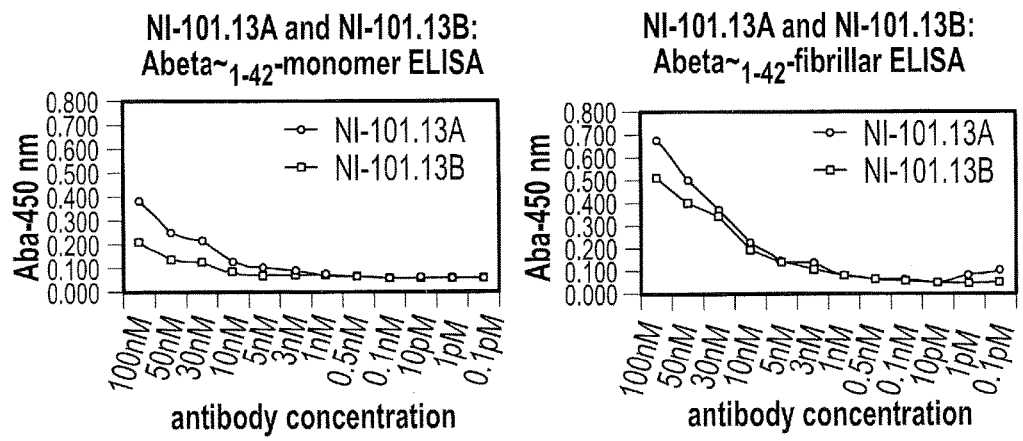
FIG. 13: ELISA showing preferential binding of NI-101.13A and NI-101.13B to artificial amyloid fibrils as compared to monomeric Abeta.

Recombinant human antibodies NI-101.13A and 13B were tested for binding to brain sections obtained from an APP transgenic mouse model of Alzheimer's disease (Tg2576). NI-101.13A and NI-101.13B produced prominent staining of beta-amyloid plaques at 10 nM concentration (FIG. 12). The binding of recombinant NI-101.13A and NI-101.13B to artificial amyloid fibrils prepared from synthetic Abeta1-42 peptides and monomeric Abeta was determined by ELISA. Synthetic Abeta fibrils or monomeric synthetic Abeta coated onto ELISA plates at equal coating densities were incubated with NI-101.13A and NI-101.13B at the indicated concentrations. Preferential binding to artificial amyloid fibrils as compared to monomeric Abeta was observed for both antibodies tested. (FIG. 13)

NI-101.12

The binding of recombinant NI-101.12 to synthetic Abeta1-42 peptide was confirmed by ELISA (FIG. 14A). NI-101.12 binding at 133nM concentration was competed by excess of Abeta1-42 peptide (FIG. 14B).

Example 3

Recombinant Human Antibody Against Brain Beta-Amyloid Crosses the Blood Brain Barrier in a Transgenic Mouse Model of Alzheimer's Disease, and Binds to Brain Beta-Amyloid Plaques In Vivo To determine whether recombinant human NI-101.11 antibody crosses the blood brain barrier and binds to brain beta-amyloid plaques in vivo transgenic PS-1/APPswe Alzheimer's disease model mice received two peripheral injections of 150 µg NI-101.11 at day 1 and day 3. Mice were sacrificed 24 h after the second injection and perfused with PBS. Brains were harvested and brain sections were stained with FITC-labeled antibodies against human IgG or with the mouse monoclonal Abeta antibody 6E10 followed by a FITC-labeled antibody against mouse IgG to confirm the presence of brain beta-amyloid plaques. Intense staining of amyloid plaques with anti-human IgG indicated that the recombinant human NI-101.11 antibody can cross the blood-brain barrier of transgenic mice and bind to brain beta-amyloid plaques in living animals (FIG. 15).

Example 4

Recombinant Human Antibody Against Beta-Amyloid Improves Abnormal Cognitive Behavior and Confers Reduction of Beta-Amyloid Plaque Load, Astrogliosis and Microgliosis in a Transgenic Mouse Model of Alzheimer's Disease without Increasing the Frequency of Microhemorrhages 24 months old arcAbeta mice and age-matched wild type littermates were treated weekly i.p. with 3 mg/kg recombinant human NI-101.11 antibody or an isotype-matched human control antibody for 2 months. To assess the treatment effect on abnormal behavior in the transgenic mice, Y-maze behavioral testing was performed before and after completion of the treatment. The spontaneous rate of alternation was assessed using a Y-shaped plastic maze, with 40×20×10 cm arm sizes. During 5 min sessions, the sequences of arm entries were recorded; alternation was defined as successive entries into the three arms, in overlapping triplet sets. The percent alternation was calculated as the ratio of actual to possible alternations (defined as the total number of arm entries—2) multiplied by 100%. The Y-maze performance of untreated arcAbeta mice and wildtype littermate controls was compared using an unpaired t-test. The nonparametric Kruskal-Wallis test was used to compare the improvement after treatment in all 4 groups. The nonparametric Mann-Whitney U test was chosen for pair-wise comparison of the different groups. Zero-performers (i.e. mice that did not leave the arm they were placed in) were excluded from the analysis.

Figures 16A, 16B:
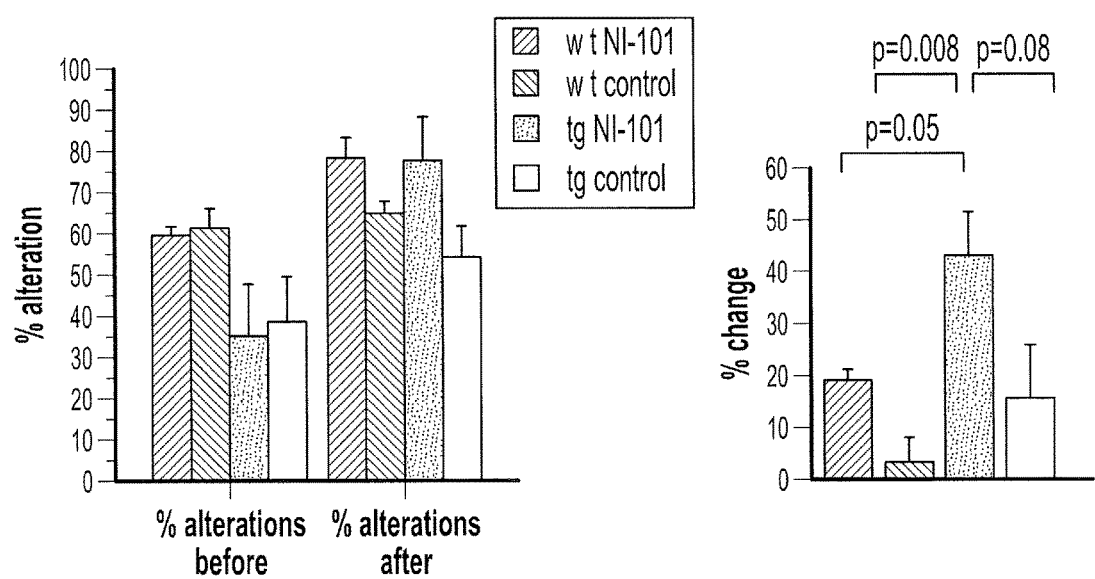
FIG. 16A: is a bar graph depicting the percentage alteration on abnormal behavior of arcAbeta mice following treatment with recombinant human NI-101.11 antibody. 24 months old arcAbeta mice were treated weekly i.p. with 3 mg/kg antibody for 2 months. Y-maze behavioral testing was performed before and after completion of the treatment.
FIG. 16B: is a bar graph providing the analysis of performance in the four tested groups. Recombinant human NI-101.11 antibody improves abnormal cognitive behavior in a transgenic mouse model of Alzheimer's disease.

As was observerd in previous studies, untreated 24-months old arcAbeta mice were significantly impaired compared to their wildtype littermates (FIG. 16A, before treatment; unpaired t-test, p=0.0007).

NI-101.11 treated arcAbeta mice showed clearly enhanced alteration levels, comparable to NI-101.11 treated wildtype control mice after the 2 months treatment. Analysis of the improvement (i.e. performance after treatment minus performance before treatment) showed a significant difference between the four groups (FIG. 16B, Kruskal-Wallis test; p=0.03). A pair-wise post-hoc analysis between all groups showed that NI-101.11 treated arcAbeta mice improved their cognitive performance significantly more than wildtype mice (Mann-Whitney U; p=0.05 NI-101.11 tg vs. NI-101.11 wt; p=0.008 NI-101.11 tg vs. control wt). This group of mice also showed a strong trend towards improved performance compared to the control antibody treated transgenic littermates (Mann-Whitney-U; p=0.08 NI-101.11 tg vs. control tg). All mice showed a ~10% improvement in performance in the re-testing, which was likely due to the familiar environment of the task.

The effects of chronic, 2 months NI-101.11 treatment on amyloid burden, astrogliosis and microgliosis were analyzed by quantitative histochemical and immunohistochemical analysis. To that end, mice were anesthetized after completion of the behavioral testing and perfused transcardially with PBS. One brain hemisphere was fixed in 4% paraformaldehyde and embedded in paraffin. 5 µm sagittal sections were cut with a Leica RM 2135 microtome (Bannockburn, Ill.). Beta-amyloid plaque load in cortex and hippocampus was quantified on brain sections stained with Thioflavin S and Congo Red according to standard protocol. For immunohistochemistry, slices were dewaxed, blocked with 4% BSA, 5% goat serum and 5% horse serum in PBS for 1 h at RT. Antibodies were incubated overnight at 4° C. using the following dilutions: anti GFAP (Advanced Immunochemicals) 1: 500, anti IBA1 (WAKO) 1:500. 2nd fluorophore coupled antibodies were incubated at RT for 2 h. 2-3 sections per mouse brain spaced 75 µm apart were used for each staining. 2 images per section were taken at 10× magnification for cortex analysis (parietal and frontal region). The entire hippocampus area (5× magnification cropped to ROI) was taken for the hippocampus analysis. Automated image analysis was done with the software ImageJ.

Figure 17:
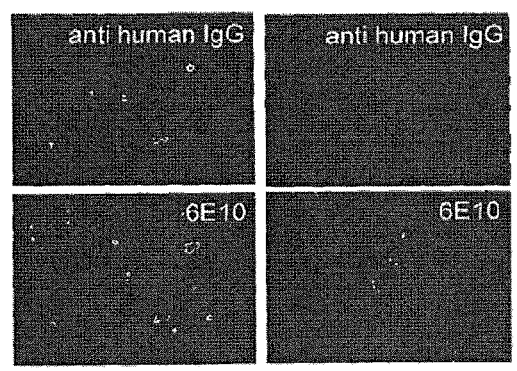
FIG. 17: Blood-brain barrier penetration and decoration of amyloid plaques by peripherally administered NI-101.11. NI-101.11 can cross the blood-brain barrier and bind to beta-amyloid deposits in NI-101.11 treated mice (left panel) whereas no such staining is visible in animals treated with the human control antibody (right panel). Recombinant human NI-101.11 antibody reduces brain beta-amyloid plaque load after systemic treatment for two months.

Double staining of brain sections from immunized arcAbeta mice with 6E10 and anti-human IgG revealed binding of NI-101.11 to Abeta deposits (FIG. 17, left panel), indicating that NI-101.11 can cross the blood brain barrier and bind to brain beta-amyloid plaques. No such binding of human antibody to Abeta deposits was seen in control antibody treated arcAbeta mice (FIG. 17 right panel).

Chronic treatment with with 3 mg/kg of NI-101.11 resulted in a significant reduction of amyloid plaque load as was revealed by Thioflavin S and Congo Red staining. This reduction reached levels of greater than 50% in cortex and hippocampus compared to control antibody-treated arcAbeta mice (FIG. 18A, B). In addition to the plaque area (FIG. 18C), significant reductions were also observed for the number of plaques (FIG. 18D) and the average plaque size (FIG. 18E).

Figure 20:
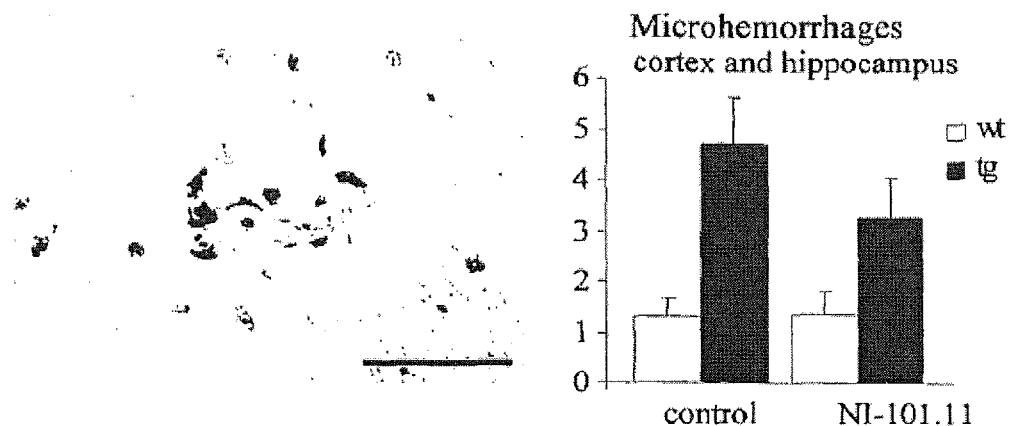
FIG. 20: No increase of brain microhemorrhages after two months of treatment with recombinant human NI-101.11 antibody. 24 months old arcAbeta mice with proven massive congophilic amyloid angiopathy were treated weekly i.p. with 3 mg/kg antibody for 2 months. Representative picture of a brain microhemorrhage in arcAbeta mice revealed by Perl's Prussian blue staining (left). Quantitative analysis demonstrates a significantly elevated frequency of micorhemorrhages in arcAbeta transgenic mice compared to their wildtype littermates. Chronic treatment with NI-101.11 did not result in increased frequency of micorhemorrhages. Scale bar: 20 µm

To test whether chronic treatment with NI-101.11 affects the neuroinflammatory response in arcAbeta mice, reactive astrocytes and microglia were quantified after immunohistological staining. A reduction in the number of reactive astrocytes (anti GFAP-staining) was observed in the cortex of NI-101.11 treated arcAbeta mice compared to control antibody treated animals (FIG. 19A; Mann-Whitney-U; p=0.047). No change was detected in the hippocampus. Staining with an antibody against a marker of microglia and macrophages (anti-Iba1) also revealed a statistical trend towards reduced inflammation (FIG. 19B; Mann-Whitney-U; p=0.075 for both cortex and hippocampus). The decrease in astrocytosis and microgliosis is in line with the reduced beta-amyloid load observed after NI-101.11 treatment Passive immunotherapy with certain monoclonal antibodies directed against Abeta can be associated with increased frequency of microhemorrhages in the brain (Pfeifer et al., Science 298 (2002), 1379; Wilcock et al., J Neuroinflammation 1 (2004), 24). To assess the effects of chronic therapy with NI-101.11, Perl's Prussian blue staining was performed on brain sections from arcAbeta and wild-type mice after chronic NI-101.11 treatment. This staining reveals the presence of hemosiderin, a breakdown product of hemoglobin, and marker of previous microhemorrages (FIG. 20). In aged arcAbeta mice treated with a control antibody, the frequency of Prussian blue positive profiles was significantly elevated compared to wild-type littermates (Mann-Whitney-U; p=0.001). Treatment with the NI-101.11 did not lead to an increase the number of microhemorraghes when compared to control-antibody treated arcAbeta mice (Mann-Whitney-U; p=0.347) indicating that the beneficial therapeutic effects of NI-101.11 treatment occurred in the absence of this frequently observed side effect of passive Abeta immunotherapy.

Example 5

Figure 21:
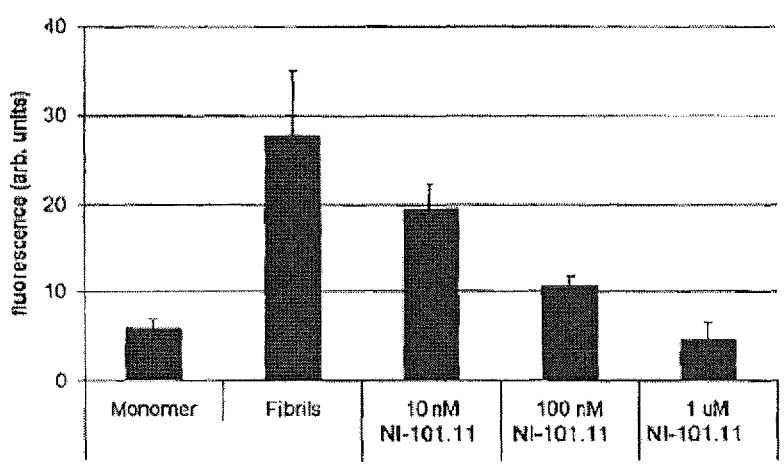
FIG. 21: Recombinant human NI-101.11 antibody inhibits the formation of synthetic Abeta fibrils in vitro. The effect of recombinant human NI-101.11 antibody on the formation of Abeta fibrils was assayed by measuring Thioflavin S bound to aggregated Abeta by fluorescence analysis.

Recombinant Human Antibody Against Brain Beta-Amyloid Inhibits the Formation of Synthetic Abeta Fibrils In Vitro The effect of recombinant human NI-101.11 antibody on the formation of Abeta-fibrils was assayed by measuring Thioflavin S bound to aggregated Abeta by fluorescence analysis. Monomeric Abeta solutions were incubated at 37° C. for 24 h in the presence of absence of increasing concentration of NI-101.11. The formation of synthetic Abeta fibrils in vitro was inhibited by recombinant human NI-101.11 in a concentration dependent manner (FIG. 21).

Example 6

NI-101.11 Effects on Ex-vivo Phagocytosis of Abeta Fibrils by BV-2 Microglial-Derived Cells The effects of NI-101.11 on Fcgamma-receptor mediated phagocytosis of Abeta fibrils were studied in the BV-2 microglial-derived cell line. BV-2 cells were maintained in DMEM supplemented with 5% FBS, Pen/Step and glutamine. Cells were trypsinized and 120,000 BV-2 cells/well were seeded in flat bottom 24-well plates. After 12 h, the medium was replaced with 400 ul DMEM/F12/well supplemented with 20 mM HEPES (pH 7.3), 1% BSA, 10 µg/ml Pen/Step. 100 µg/ml Fucoidan, an inhibitor of the scavenger receptor, was added 30 min prior to experiment. 50 µM FITC-labeled Abeta fibrils were pre-incubated with the indicated concentrations of antibodies for 30 min at 37° C., washed twice followed by centrifugation for 5 min at 14,000×g. This suspension was added to the tissue culture plates. After 30 min BV-2 cells were washed twice with HBSS to remove unassociated fibrillar Abeta.

Cells were treated with 250 µg/ml trypsin/EDTA for 20 min at 4° C. and washed twice by centrifugation at 500×g for 5 min at 4° C. Cells were fixed for 20 min in FACS-Fix (PBS, 2% FA, 2% Glucose, 5 mM NaN) and washed twice with FACS wash (PBS, 5 µM EDTA, 0.2% BSA). Fluorescence (FL-1) of 10,000 cells was determined by FACS analysis (based on Webster S D et al, JI 2001).

Figure 22:
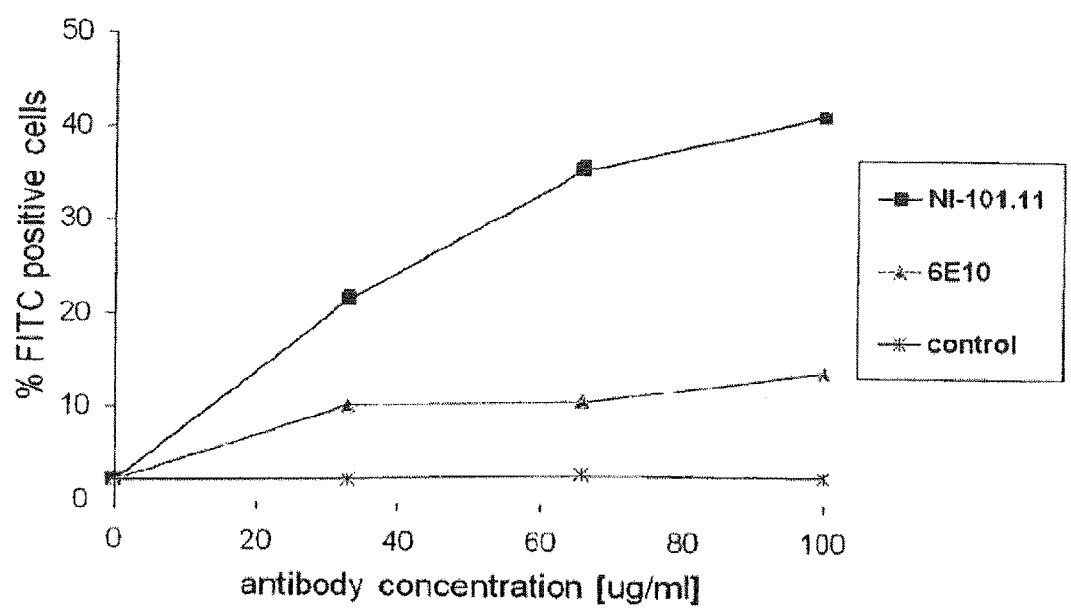
FIG. 22: Antibody-mediated dose-dependent phagocytosis of FITC-Abeta1-42 fibrils by BV-2 microglial cells was measured upon inhibition of the scavenger receptor system. NI-101.11 triggers potent dose-dependent Fcgamma receptor-mediated phagocytosis of Abeta fibrils.

Fcgamma receptor-dependent phagocytosis of FITC-labeled Abeta1-42 fibrils was measured upon inhibition of the scavenger receptor system. Comparative analysis of human NI-101.11 and a commercially available antibody directed to a linear epitope at the N-terminus of the Abeta peptide (6E10) demonstrated dose-dependent induction of phagocytosis of Abeta fibrils. The uptake of fibrils mediated by NI-101.11 is up to 3 fold higher than that observed for the 6E10 antibody (FIG. 22). These data indicate that NI-101.11 triggers potent dose-dependent Fcgamma receptor-mediated phagocytosis of Abeta fibrils by microglial cells.

CONCLUSION

As demonstrated in the above experiments performed in accordance with the present invention it was surprisingly possible to detect protective and therapeutically active antibodies and antibody producing B-cells in phenotypically healthy, asymptomatic human subjects, as well as in patients with unusually stable clinical disease courses despite a diagnosis of cognitive impairment or Alzheimer's disease. More specifically, a new class of human antibodies could be detected and isolated, which discriminate the physiologically functional form of an antigen, thereby minimizing the risk of autoimmunogenic side effects hitherto being a problem in immunotherapy. Thus, antibodies and equivalent binding molecules are provided that specifically recognize a variant of the antigen in a pathophysiologically relevant structure, which the antibody is supposed to bind in order to diminish its toxicity or to reduce its concentration or to promote its degradation, by means of, for example, making the pathogen for FcR-expressing macrophages or microglia cells visible and therefore to render it innocuous. As further demonstrated in the examples such antibodies are therapeutically effective and are capable of both suspending as well as preventing deleterious effects of abnormal pathological proteins and aggregates thereof without increasing the frequency of brain microhemorrhages.

What is claimed is:

1. A method of treating Alzheimer's disease, mild cognitive impairment, or abnormal accumulation or deposition of beta-amyloid in the central nervous system in a human subject in need thereof, the method comprising administering to the human subject a therapeutically effective amount of an antibody or antigen-binding fragment thereof that specifically binds to beta-amyloid, wherein the antibody or antigen-binding fragment thereof comprises:
   a heavy chain variable region (VH) comprising VH complementarity determining regions 1, 2, and 3 with the amino acid sequences set forth in SEQ ID NO:20, SEQ ID NO:21, SEQ ID NO:22, respectively; and
   a light chain variable region (VL) comprising VL complementarity determining regions 1, 2, and 3 with the amino acid sequences set forth in SEQ ID NO:23, SEQ ID NO:24, and SEQ ID NO:25, respectively.

2. The method of claim 1, wherein the antibody or antigen-binding fragment thereof comprises a human IgG1 constant region or a fragment thereof.

3. The method of claim 2, wherein the antibody or antigen-binding fragment thereof binds to beta-amyloid plaques, cerebrovascular amyloid, or diffuse Abeta deposits.

4. The method of claim 3, wherein the antibody or antigen-binding fragment is administered intravenously.

5. The method of claim 2, wherein the antibody or antigen-binding fragment is administered intravenously.

6. The method of claim 1, wherein the antibody or antigen-binding fragment thereof binds to beta-amyloid plaques, cerebrovascular amyloid, or diffuse Abeta deposits.

7. The method of claim 6, wherein the antibody or antigen-binding fragment is administered intravenously.

8. The method of claim 1, wherein the antibody or antigen-binding fragment is administered intravenously.

9. The method of claim 1, wherein the antibody or antigen-binding fragment is a human antibody or fragment thereof.

10. The method of claim 1, wherein the therapeutically effective amount is within the range of 1-10 mg/kg of body weight of the subject.

11. The method of claim 1, wherein the therapeutically effective amount is 1 mg/kg of body weight of the subject.

12. The method of claim 1, wherein the therapeutically effective amount is 2 mg/kg of body weight of the subject.

13. The method of claim 1, wherein the therapeutically effective amount is 3 mg/kg of body weight of the subject.

14. The method of claim 1, wherein the therapeutically effective amount is 5 mg/kg of body weight of the subject.

15. The method of claim 1, wherein the therapeutically effective amount is 10 mg/kg of body weight of the subject.

16. The method of claim 1, wherein the therapeutically effective amount is 15 mg/kg of body weight of the subject.

17. The method of claim 1, wherein the therapeutically effective amount is 30 mg/kg of body weight of the subject.

18. The method of claim 1, wherein the antibody or antigen-binding fragment is administered in multiple doses.

19. The method of claim 1, wherein the antibody or antigen-binding fragment is administered in multiple doses over a period of at least six months.

20. The method of claim 1, further comprising monitoring the subject by periodic assessment for inhibition or regression of symptoms of Alzheimer's disease.

21. A method of treating Alzheimer's disease, mild cognitive impairment, or abnormal accumulation or deposition of beta-amyloid in the central nervous system in a human subject in need thereof, the method comprising administering to the human subject a therapeutically effective amount of an antibody or antigen-binding fragment thereof that specifically binds to beta-amyloid, wherein the antibody or antigen-binding fragment thereof comprises:
   a heavy chain variable region with the amino acid sequence set forth in SEQ ID NO:39; and
   a light chain variable region with the amino acid sequence set forth in SEQ ID NO:41.

22. The method of claim 21, wherein the antibody or antigen-binding fragment thereof comprises a human IgG1 constant region or a fragment thereof.

23. The method of claim 22, wherein the antibody or antigen-binding fragment thereof binds to beta-amyloid plaques, cerebrovascular amyloid, or diffuse Abeta deposits.

24. The method of claim 23, wherein the antibody or antigen-binding fragment is administered intravenously.

25. The method of claim 22, wherein the antibody or antigen-binding fragment is administered intravenously.

26. The method of claim 21, wherein the antibody or antigen-binding fragment thereof binds to beta-amyloid plaques, cerebrovascular amyloid, or diffuse Abeta deposits.

27. The method of claim 26, wherein the antibody or antigen-binding fragment is administered intravenously.

28. The method of claim 21, wherein the antibody or antigen-binding fragment is administered intravenously.

29. The method of claim 21, wherein the antibody or antigen-binding fragment is a human antibody or fragment thereof.

30. The method of claim 21, wherein the therapeutically effective amount is within the range of 1-10 mg/kg of body weight of the subject.

31. The method of claim 21, wherein the therapeutically effective amount is 1 mg/kg of body weight of the subject.

32. The method of claim 21, wherein the therapeutically effective amount is 2 mg/kg of body weight of the subject.

33. The method of claim 21, wherein the therapeutically effective amount is 3 mg/kg of body weight of the subject.

34. The method of claim 21, wherein the therapeutically effective amount is 5 mg/kg of body weight of the subject.

35. The method of claim 21, wherein the therapeutically effective amount is 10 mg/kg of body weight of the subject.

36. The method of claim 21, wherein the therapeutically effective amount is 15 mg/kg of body weight of the subject.

37. The method of claim 21, wherein the therapeutically effective amount is 30 mg/kg of body weight of the subject.

38. The method of claim 21, wherein the antibody or antigen-binding fragment is administered in multiple doses.

39. The method of claim 21, wherein the antibody or antigen-binding fragment is administered in multiple doses over a period of at least six months.

40. The method of claim 21, further comprising monitoring the subject by periodic assessment for inhibition or regression of symptoms of Alzheimer's disease.

41. A method of treating Alzheimer's disease, mild cognitive impairment, or abnormal accumulation or deposition of beta-amyloid in the central nervous system in a human subject in need thereof, the method comprising administering to the human subject a therapeutically effective amount of an antibody that specifically binds to beta-amyloid, wherein the antibody comprises:
   a heavy chain comprising heavy chain variable region complementarity determining regions 1, 2, and 3 with the amino acid sequences set forth in SEQ ID NO:20, SEQ ID NO:21, SEQ ID NO:22, respectively; and
   a light chain comprising light chain variable region complementarity determining regions 1, 2, and 3 with the amino acid sequences set forth in SEQ ID NO:23, SEQ ID NO:24, and SEQ ID NO:25, respectively.

42. The method of claim 41, wherein the heavy chain comprises a human IgG1 heavy chain constant region.

43. The method of claim 42, wherein the antibody binds to beta-amyloid plaques, cerebrovascular amyloid, or diffuse Abeta deposits.

44. The method of claim 43, wherein the antibody is administered intravenously.

45. The method of claim 42, wherein the antibody is administered intravenously.

46. The method of claim 41, wherein the heavy chain comprises a human IgG1 heavy chain constant region and the light chain comprises a human kappa light chain constant region.

47. The method of claim 46, wherein the antibody binds to beta-amyloid plaques, cerebrovascular amyloid, or diffuse Abeta deposits.

48. The method of claim 47, wherein the antibody is administered intravenously.

49. The method of claim 46, wherein the antibody is administered intravenously.

50. The method of claim 41, wherein the antibody binds to beta-amyloid plaques, cerebrovascular amyloid, or diffuse Abeta deposits.

51. The method of claim 50, wherein the antibody is administered intravenously.

52. The method of claim 41, wherein the antibody is administered intravenously.

53. The method of claim 41, wherein the antibody is a human antibody.

54. The method of claim 41, wherein the therapeutically effective amount is within the range of 1-10 mg/kg of body weight of the subject.

55. The method of claim 41, wherein the therapeutically effective amount is 1 mg/kg of body weight of the subject.

56. The method of claim 41, wherein the therapeutically effective amount is 2 mg/kg of body weight of the subject.

57. The method of claim 41, wherein the therapeutically effective amount is 3 mg/kg of body weight of the subject.

58. The method of claim 41, wherein the therapeutically effective amount is 5 mg/kg of body weight of the subject.

59. The method of claim 41, wherein the therapeutically effective amount is 10 mg/kg of body weight of the subject.

60. The method of claim 41, wherein the therapeutically effective amount is 15 mg/kg of body weight of the subject.

61. The method of claim 41, wherein the therapeutically effective amount is 30 mg/kg of body weight of the subject.

62. The method of claim 41, wherein the antibody is administered in multiple doses.

63. The method of claim 41, wherein the antibody is administered in multiple doses over a period of at least six months.

64. The method of claim 41, further comprising monitoring the subject by periodic assessment for inhibition or regression of symptoms of Alzheimer's disease.

65. A method of treating Alzheimer's disease, mild cognitive impairment, or abnormal accumulation or deposition of beta-amyloid in the central nervous system in a human subject in need thereof, the method comprising administering to the human subject a therapeutically effective amount of an antibody that specifically binds to beta-amyloid, wherein the antibody comprises:

a heavy chain comprising a heavy chain variable region with the amino acid sequence set forth in SEQ ID NO:39; and a light chain comprising a light chain variable region with the amino acid sequence set forth in SEQ ID NO:41.

66. The method of claim 65, wherein the heavy chain comprises a human IgG1 heavy chain constant region.

67. The method of claim 66, wherein the antibody binds to beta-amyloid plaques, cerebrovascular amyloid, or diffuse Abeta deposits.

68. The method of claim 67, wherein the antibody is administered intravenously.

69. The method of claim 66, wherein the antibody is administered intravenously.

70. The method of claim 65, wherein the heavy chain comprises a human IgG1 heavy chain constant region and the light chain comprises a human kappa light chain constant region.

71. The method of claim 70, wherein the antibody binds to beta-amyloid plaques, cerebrovascular amyloid, or diffuse Abeta deposits.

72. The method of claim 71, wherein the antibody is administered intravenously.

73. The method of claim 70, wherein the antibody is administered intravenously.

74. The method of claim 65, wherein the antibody binds to beta-amyloid plaques, cerebrovascular amyloid, or diffuse Abeta deposits.

75. The method of claim 74, wherein the antibody is administered intravenously.

76. The method of claim 65, wherein the antibody is administered intravenously.

77. The method of claim 65, wherein the antibody is a human antibody.

78. The method of claim 65, wherein the therapeutically effective amount is within the range of 1-10 mg/kg of body weight of the subject.

79. The method of claim 65, wherein the therapeutically effective amount is 1 mg/kg of body weight of the subject.

80. The method of claim 65, wherein the therapeutically effective amount is 2 mg/kg of body weight of the subject.

81. The method of claim 65, wherein the therapeutically effective amount is 3 mg/kg of body weight of the subject.

82. The method of claim 65, wherein the therapeutically effective amount is 5 mg/kg of body weight of the subject.

83. The method of claim 65, wherein the therapeutically effective amount is 10 mg/kg of body weight of the subject.

84. The method of claim 65, wherein the therapeutically effective amount is 15 mg/kg of body weight of the subject.

85. The method of claim 65, wherein the therapeutically effective amount is 30 mg/kg of body weight of the subject.

86. The method of claim 65, wherein the antibody is administered in multiple doses.

87. The method of claim 65, wherein the antibody is administered in multiple doses over a period of at least six months.

88. The method of claim 65, further comprising monitoring the subject by periodic assessment for inhibition or regression of symptoms of Alzheimer's disease.

* * * * *

SEQUENCE LISTING

<160> NUMBER OF SEQ ID NOS: 56

<210> SEQ ID NO 1
<211> LENGTH: 66
<212> TYPE: DNA
<213> ORGANISM: Homo sapiens
<220> FEATURE:
<221> NAME/KEY: misc_feature
<222> LOCATION: (1)..(66)
<223> OTHER INFORMATION: Leader peptide derived from human Vkappa I L5, restriction site Xba 1 introduced 3' of the sequence
<220> FEATURE:
<221> NAME/KEY: CDS
<222> LOCATION: (1)..(66)

<400> SEQUENCE: 1

```
atg gac atg cgg gtg ccc gcc cag ctg ctg ggc ctg ctg ctg ctg tgg     48
Met Asp Met Arg Val Pro Ala Gln Leu Leu Gly Leu Leu Leu Leu Trp
1               5                   10                  15 ttc ccc ggc tct aga tgc                                              66
Phe Pro Gly Ser Arg Cys
            20
```

<210> SEQ ID NO 2
<211> LENGTH: 22
<212> TYPE: PRT
<213> ORGANISM: Homo sapiens

<400> SEQUENCE: 2

```
Met Asp Met Arg Val Pro Ala Gln Leu Leu Gly Leu Leu Leu Leu Trp
1               5                   10                  15

Phe Pro Gly Ser Arg Cys
            20
```

<210> SEQ ID NO 3
<211> LENGTH: 372
<212> TYPE: DNA
<213> ORGANISM: Homo sapiens
<220> FEATURE:
<221> NAME/KEY: V_region
<222> LOCATION: (1)..(372)
<223> OTHER INFORMATION: NI-101.10-variable heavy (Vh) chain sequence
<220> FEATURE:
<221> NAME/KEY: CDS
<222> LOCATION: (1)..(372)

<400> SEQUENCE: 3

```
gag gtg cag cta gtg cag tct ggg gga ggc gtg gtc cag cct ggg agg     48
Glu Val Gln Leu Val Gln Ser Gly Gly Gly Val Val Gln Pro Gly Arg
1               5                   10                  15 tcc ctg aga ctc tcc tgt gca gcg tct gga ttc gcc ttc agt agc tat     96
Ser Leu Arg Leu Ser Cys Ala Ala Ser Gly Phe Ala Phe Ser Ser Tyr
            20                  25                  30 ggc ata cac tgg gtc cgc cag gct cca ggc aag ggg ctg gag tgg gtg    144
Gly Ile His Trp Val Arg Gln Ala Pro Gly Lys Gly Leu Glu Trp Val
        35                  40                  45 gca gtt ata tgg ttt gat gga act aaa aaa tac tat aca gac tcc gtg    192
Ala Val Ile Trp Phe Asp Gly Thr Lys Lys Tyr Tyr Thr Asp Ser Val
    50                  55                  60 aag ggc aga ttc acc atc tcc aga gac aat tcc aag aac aca ctg tat    240
Lys Gly Arg Phe Thr Ile Ser Arg Asp Asn Ser Lys Asn Thr Leu Tyr
65                  70                  75                  80 ctg caa atg aac acc ctg aga gcc gag gac acg gct gtg tat tac tgt    288
Leu Gln Met Asn Thr Leu Arg Ala Glu Asp Thr Ala Val Tyr Tyr Cys
                85                  90                  95
```

```
gcg aga gat agg ggt ata gga gct cgg cgg ggg ccg tac tac atg gac     336
Ala Arg Asp Arg Gly Ile Gly Ala Arg Arg Gly Pro Tyr Tyr Met Asp
            100                 105                 110 gtc tgg ggc aaa ggg acc acg gtc acc gtc tcc tca                     372
Val Trp Gly Lys Gly Thr Thr Val Thr Val Ser Ser
        115                 120
```

```
<210> SEQ ID NO 4
<211> LENGTH: 124
<212> TYPE: PRT
<213> ORGANISM: Homo sapiens

<400> SEQUENCE: 4

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Ile His Trp Val Arg Gln Ala Pro Gly Lys Gly Leu Glu Trp Val
        35                  40                  45

Ala Val Ile Trp Phe Asp Gly Thr Lys Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Arg Asp Arg Gly Ile Gly Ala Arg Arg Gly Pro Tyr Tyr Met Asp
            100                 105                 110

Val Trp Gly Lys Gly Thr Thr Val Thr Val Ser Ser
        115                 120
```

```
<210> SEQ ID NO 5
<211> LENGTH: 372
<212> TYPE: DNA
<213> ORGANISM: Artificial
<220> FEATURE:
<223> OTHER INFORMATION: Codon optimized
<220> FEATURE:
<221> NAME/KEY: V_region
<222> LOCATION: (1)..(372)
<223> OTHER INFORMATION: NI-101.11-variable heavy (Vh) chain sequence
<220> FEATURE:
<221> NAME/KEY: CDS
<222> LOCATION: (1)..(372)

<400> SEQUENCE: 5 gag gtg cag ctg gtg cag agc ggc ggc ggc gtg gtg cag ccc ggc cgg     48
Glu Val Gln Leu Val Gln Ser Gly Gly Gly Val Val Gln Pro Gly Arg
1               5                   10                  15 agc ctg cgg ctg agc tgc gcc gcc agc ggc ttc gcc ttc agc agc tac     96
Ser Leu Arg Leu Ser Cys Ala Ala Ser Gly Phe Ala Phe Ser Ser Tyr
            20                  25                  30 ggc atg cac tgg gtg cgg cag gcc ccc ggc aag ggc ctg gag tgg gtg    144
Gly Met His Trp Val Arg Gln Ala Pro Gly Lys Gly Leu Glu Trp Val
        35                  40                  45 gcc gtg atc tgg ttc gac ggc acc aag aag tac tac acc gac agc gtg    192
Ala Val Ile Trp Phe Asp Gly Thr Lys Lys Tyr Tyr Thr Asp Ser Val
    50                  55                  60 aag ggc cgg ttc acc atc agc cgg gac aac agc aag aac acc ctg tac    240
Lys Gly Arg Phe Thr Ile Ser Arg Asp Asn Ser Lys Asn Thr Leu Tyr
65                  70                  75                  80 ctg cag atg aac acc ctg cgg gcc gag gac acc gcc gtg tac tac tgc    288
Leu Gln Met Asn Thr Leu Arg Ala Glu Asp Thr Ala Val Tyr Tyr Cys
```

```
                     85                  90                  95
gcc cgg gac cgg ggc atc ggc gcc cgg cgg ggc ccc tac tac atg gac        336
Ala Arg Asp Arg Gly Ile Gly Ala Arg Arg Gly Pro Tyr Tyr Met Asp
                    100                 105                 110 gtg tgg ggc aag ggc acc acc gtg acc gtg agc agc                        372
Val Trp Gly Lys Gly Thr Thr Val Thr Val Ser Ser
        115                 120

<210> SEQ ID NO 6
<211> LENGTH: 124
<212> TYPE: PRT
<213> ORGANISM: Homo sapiens

<400> SEQUENCE: 6

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Ala Phe Ser Ser Tyr
                20                  25                  30

Gly Met His Trp Val Arg Gln Ala Pro Gly Lys Gly Leu Glu Trp Val
            35                  40                  45

Ala Val Ile Trp Phe Asp Gly Thr Lys Lys Tyr Tyr Thr Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Arg Asp Arg Gly Ile Gly Ala Arg Arg Gly Pro Tyr Tyr Met Asp
                100                 105                 110

Val Trp Gly Lys Gly Thr Thr Val Thr Val Ser Ser
            115                 120

<210> SEQ ID NO 7
<211> LENGTH: 327
<212> TYPE: DNA
<213> ORGANISM: Homo sapiens
<220> FEATURE:
<221> NAME/KEY: V_region
<222> LOCATION: (1)..(327)
<223> OTHER INFORMATION: NI-101.10 and NI-101-11-variable kappa (Vkappa)
      light chain sequence
<220> FEATURE:
<221> NAME/KEY: CDS
<222> LOCATION: (1)..(327)

<400> SEQUENCE: 7 gaa att gtg ctg act cag tct cca tcc tcc ctg tct gca tct gta gga         48
Glu Ile Val Leu Thr Gln Ser Pro Ser Ser Leu Ser Ala Ser Val Gly
1               5                   10                  15 gac aga gtc acc atc act tgc cgg gca agt cag agc att agc agc tat         96
Asp Arg Val Thr Ile Thr Cys Arg Ala Ser Gln Ser Ile Ser Ser Tyr
                20                  25                  30 tta aat tgg tat caa cag aaa cca ggg aaa gcc cct aag ctc ctg atc        144
Leu Asn Trp Tyr Gln Gln Lys Pro Gly Lys Ala Pro Lys Leu Leu Ile
            35                  40                  45 tat gct gca tcc agt ttg caa agt ggg gtc cca tca agg ttc agt ggc        192
Tyr Ala Ala Ser Ser Leu Gln Ser Gly Val Pro Ser Arg Phe Ser Gly
        50                  55                  60 agt gga tct ggg aca gat ttc act ctc acc atc agc agt ctg caa cct        240
Ser Gly Ser Gly Thr Asp Phe Thr Leu Thr Ile Ser Ser Leu Gln Pro
65                  70                  75                  80 gaa gat ttt gca act tat tac tgt cag cag agt tac agt acc cct ctc        288
Glu Asp Phe Ala Thr Tyr Tyr Cys Gln Gln Ser Tyr Ser Thr Pro Leu
```

```
Glu Asp Phe Ala Thr Tyr Tyr Cys Gln Gln Ser Tyr Ser Thr Pro Leu
                85                  90                  95 act ttc ggc gga ggg acc aag ctc gag atc aaa cgt acg                327
Thr Phe Gly Gly Gly Thr Lys Leu Glu Ile Lys Arg Thr
            100                 105

<210> SEQ ID NO 8
<211> LENGTH: 109
<212> TYPE: PRT
<213> ORGANISM: Homo sapiens

<400> SEQUENCE: 8

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Leu Glu Ile Lys Arg Thr
            100                 105

<210> SEQ ID NO 9
<211> LENGTH: 381
<212> TYPE: DNA
<213> ORGANISM: Homo sapiens
<220> FEATURE:
<221> NAME/KEY: V_region
<222> LOCATION: (1)..(381)
<223> OTHER INFORMATION: NI-101.12-variable heavy (Vh) chain sequence
<220> FEATURE:
<221> NAME/KEY: CDS
<222> LOCATION: (1)..(381)

<400> SEQUENCE: 9 gag gtg cag ctg gtg gag agc ggc ccc ggc ctg gtg aag ccc gcc gag     48
Glu Val Gln Leu Val Glu Ser Gly Pro Gly Leu Val Lys Pro Ala Glu
1               5                   10                  15 acc ctg agc ctg acc tgc acc gtg agc ggc ggc agc atc cgg agc ggc     96
Thr Leu Ser Leu Thr Cys Thr Val Ser Gly Gly Ser Ile Arg Ser Gly
            20                  25                  30 agc atc tgc tgg tac tgg atc cgg cag ccc ccc ggc aag ggc ctg gag    144
Ser Ile Cys Trp Tyr Trp Ile Arg Gln Pro Pro Gly Lys Gly Leu Glu
        35                  40                  45 tgg atc ggc tac ttc tgc tac agc ggc gcc acc ttc tac acc ccc agc    192
Trp Ile Gly Tyr Phe Cys Tyr Ser Gly Ala Thr Phe Tyr Thr Pro Ser
    50                  55                  60 ctg cgg ggc cgg ctg acc atc agc gtg gac gcc agc aag aac cag ctg    240
Leu Arg Gly Arg Leu Thr Ile Ser Val Asp Ala Ser Lys Asn Gln Leu
65                  70                  75                  80 agc ctg agc ctg agc agc gtg acc gcc gcc gac acc gcc gtg tac tac    288
Ser Leu Ser Leu Ser Ser Val Thr Ala Ala Asp Thr Ala Val Tyr Tyr
                85                  90                  95 tgc gcc cgg cgg gcc ggc gag aac agc ggc ggc atc gag ccc tac tac    336
Cys Ala Arg Arg Ala Gly Glu Asn Ser Gly Gly Ile Glu Pro Tyr Tyr
            100                 105                 110
```

```
ggc atg gac gtg tgg ggc cag ggc acc acc gtg acc gtg agc agc            381
Gly Met Asp Val Trp Gly Gln Gly Thr Thr Val Thr Val Ser Ser
        115                 120                 125

<210> SEQ ID NO 10
<211> LENGTH: 127
<212> TYPE: PRT
<213> ORGANISM: Homo sapiens

<400> SEQUENCE: 10

Glu Val Gln Leu Val Glu Ser Gly Pro Gly Leu Val Lys Pro Ala Glu
1               5                   10                  15

Thr Leu Ser Leu Thr Cys Thr Val Ser Gly Gly Ser Ile Arg Ser Gly
            20                  25                  30

Ser Ile Cys Trp Tyr Trp Ile Arg Gln Pro Pro Gly Lys Gly Leu Glu
        35                  40                  45

Trp Ile Gly Tyr Phe Cys Tyr Ser Gly Ala Thr Phe Tyr Thr Pro Ser
    50                  55                  60

Leu Arg Gly Arg Leu Thr Ile Ser Val Asp Ala Ser Lys Asn Gln Leu
65                  70                  75                  80

Ser Leu Ser Leu Ser Ser Val Thr Ala Ala Asp Thr Ala Val Tyr Tyr
                85                  90                  95

Cys Ala Arg Arg Ala Gly Glu Asn Ser Gly Gly Ile Glu Pro Tyr Tyr
            100                 105                 110

Gly Met Asp Val Trp Gly Gln Gly Thr Thr Val Thr Val Ser Ser
        115                 120                 125

<210> SEQ ID NO 11
<211> LENGTH: 330
<212> TYPE: DNA
<213> ORGANISM: Homo sapiens
<220> FEATURE:
<221> NAME/KEY: V_region
<222> LOCATION: (1)..(330)
<223> OTHER INFORMATION: NI-101.12-variable kappa (Vkappa) light chain
      sequence
<220> FEATURE:
<221> NAME/KEY: CDS
<222> LOCATION: (1)..(330)

<400> SEQUENCE: 11 gac gag atc gtg ctg acc cag agc ccc agc agc ctg agc gcc agc atc       48
Asp Glu Ile Val Leu Thr Gln Ser Pro Ser Ser Leu Ser Ala Ser Ile
1               5                   10                  15 ggc gac cgg gtg acc atc acc tgc cgg gcc agc gag agc atc aac aag       96
Gly Asp Arg Val Thr Ile Thr Cys Arg Ala Ser Glu Ser Ile Asn Lys
            20                  25                  30 tac gtg aac tgg tac cag cag aag ccc ggc aag gcc ccc aag ctg ctg      144
Tyr Val Asn Trp Tyr Gln Gln Lys Pro Gly Lys Ala Pro Lys Leu Leu
        35                  40                  45 atc tac gcc gcc agc agc ctg cag agc ggc gcc ccc agc cgg gtg agc      192
Ile Tyr Ala Ala Ser Ser Leu Gln Ser Gly Ala Pro Ser Arg Val Ser
    50                  55                  60 ggc agc ggc ttc ggc cgg gac ttc agc ctg acc atc agc ggc ctg cag      240
Gly Ser Gly Phe Gly Arg Asp Phe Ser Leu Thr Ile Ser Gly Leu Gln
65                  70                  75                  80 gcc gag gac ttc ggc gcc tac ttc tgc cag cag agc tac agc gcc ccc      288
Ala Glu Asp Phe Gly Ala Tyr Phe Cys Gln Gln Ser Tyr Ser Ala Pro
                85                  90                  95 tac acc ttc ggc cag ggc acc aag gtg gag atc aag cgg acc                330
Tyr Thr Phe Gly Gln Gly Thr Lys Val Glu Ile Lys Arg Thr
            100                 105                 110
```

<210> SEQ ID NO 12
<211> LENGTH: 110
<212> TYPE: PRT
<213> ORGANISM: Homo sapiens

<400> SEQUENCE: 12

```
Asp Glu Ile Val Leu Thr Gln Ser Pro Ser Ser Leu Ser Ala Ser Ile
1               5                   10                  15

Gly Asp Arg Val Thr Ile Thr Cys Arg Ala Ser Glu Ser Ile Asn Lys
            20                  25                  30

Tyr Val Asn Trp Tyr Gln Gln Lys Pro Gly Lys Ala Pro Lys Leu Leu
        35                  40                  45

Ile Tyr Ala Ala Ser Ser Leu Gln Ser Gly Ala Pro Ser Arg Val Ser
50                  55                  60

Gly Ser Gly Phe Gly Arg Asp Phe Ser Leu Thr Ile Ser Gly Leu Gln
65                  70                  75                  80

Ala Glu Asp Phe Gly Ala Tyr Phe Cys Gln Gln Ser Tyr Ser Ala Pro
                85                  90                  95

Tyr Thr Phe Gly Gln Gly Thr Lys Val Glu Ile Lys Arg Thr
            100                 105                 110
```

<210> SEQ ID NO 13
<211> LENGTH: 363
<212> TYPE: DNA
<213> ORGANISM: Homo sapiens
<220> FEATURE:
<221> NAME/KEY: V_region
<222> LOCATION: (1)..(363)
<223> OTHER INFORMATION: NI-101.13-variable heavy (Vh) chain sequence
<220> FEATURE:
<221> NAME/KEY: CDS
<222> LOCATION: (1)..(363)

<400> SEQUENCE: 13

```
cag gta cag ctg cag gag tca ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc agc aga aga      96
Thr Leu Ser Leu Thr Cys Thr Val Ser Gly Gly Ser Ile Ser Arg Arg
            20                  25                  30 agt tac tac tgg ggc tgg atc cgc cag tcc cca ggg aag ggg ctg gag     144
Ser Tyr Tyr Trp Gly Trp Ile Arg Gln Ser Pro Gly Lys Gly Leu Glu
        35                  40                  45 tgg agt gga agt atc cat tat agc ggg agc acc tac tac aac ccg tcc     192
Trp Ser Gly Ser Ile His Tyr Ser Gly Ser Thr Tyr Tyr Asn Pro Ser
50                  55                  60 ctc aag agt cga gtc acc ata tct gta gac acg tcc aag aac cag ttc     240
Leu Lys Ser Arg Val Thr Ile Ser Val Asp Thr Ser Lys Asn Gln Phe
65                  70                  75                  80 tcc ctg aaa ctg agc tct gtt acc gcc gca gac acg gct gtc tat tac     288
Ser Leu Lys Leu Ser Ser Val Thr Ala Ala Asp Thr Ala Val Tyr Tyr
                85                  90                  95 tgt gcg aga tca cgt tgg ggc agc agc tgg gta ttt gac tac tgg ggc     336
Cys Ala Arg Ser Arg Trp Gly Ser Ser Trp Val Phe Asp Tyr Trp Gly
            100                 105                 110 cag ggc aca ctg gtc acc gtc tct tcg                                  363
Gln Gly Thr Leu Val Thr Val Ser Ser
        115                 120
```

<210> SEQ ID NO 14

-continued

```
<211> LENGTH: 121
<212> TYPE: PRT
<213> ORGANISM: Homo sapiens

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Arg
            20                  25                  30

Ser Tyr Tyr Trp Gly Trp Ile Arg Gln Ser Pro Gly Lys Gly Leu Glu
        35                  40                  45

Trp Ser Gly Ser Ile His Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Arg Trp Gly Ser Ser Trp Val Phe Asp Tyr Trp Gly
            100                 105                 110

Gln Gly Thr Leu Val Thr Val Ser Ser
        115                 120

<210> SEQ ID NO 15
<211> LENGTH: 330
<212> TYPE: DNA
<213> ORGANISM: Homo sapiens
<220> FEATURE:
<221> NAME/KEY: V_region
<222> LOCATION: (1)..(330)
<223> OTHER INFORMATION: NI-101.13-variable lambda (Vlambda) light chain
      sequence
<220> FEATURE:
<221> NAME/KEY: CDS
<222> LOCATION: (1)..(330)

<400> SEQUENCE: 15 cag agc gtg ctg acc cag ccg ccg agc gcg agc ggc acc ccg ggc cag        48
Gln Ser Val Leu Thr Gln Pro Pro Ser Ala Ser Gly Thr Pro Gly Gln
1               5                   10                  15 cgc gtg acc att agc tgc agc ggc agc agc aac att ggc agc aac            96
Arg Val Thr Ile Ser Cys Ser Gly Ser Ser Asn Ile Gly Ser Asn
            20                  25                  30 tat gtg tat tgg tat cag cag ccg ccg ggc acc gcg ccg aaa ctg ctg       144
Tyr Val Tyr Trp Tyr Gln Gln Pro Pro Gly Thr Ala Pro Lys Leu Leu
        35                  40                  45 att tat cgc aac aac cag cgc ccg agc ggc gtg ccg gat cgc ttt agc       192
Ile Tyr Arg Asn Asn Gln Arg Pro Ser Gly Val Pro Asp Arg Phe Ser
    50                  55                  60 ggc agc aaa agc ggc acc agc gcg agc ctg gcg att agc ggc ctg cgc       240
Gly Ser Lys Ser Gly Thr Ser Ala Ser Leu Ala Ile Ser Gly Leu Arg
65                  70                  75                  80 agc gaa gat gaa gcg gat tat tat tgc gcg gcg tgg gat gat agc ctg       288
Ser Glu Asp Glu Ala Asp Tyr Tyr Cys Ala Ala Trp Asp Asp Ser Leu
                85                  90                  95 agc ggc tat gtg ttt ggc acc ggc acc aaa gtg acc gtg ctg               330
Ser Gly Tyr Val Phe Gly Thr Gly Thr Lys Val Thr Val Leu
            100                 105                 110

<210> SEQ ID NO 16
<211> LENGTH: 110
<212> TYPE: PRT
<213> ORGANISM: Homo sapiens
```

<400> SEQUENCE: 16

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Tyr Trp Tyr Gln Gln Pro Pro Gly Thr Ala Pro Lys Leu Leu
            35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu
            100                 105                 110

<210> SEQ ID NO 17
<211> LENGTH: 5
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(5)
<223> OTHER INFORMATION: Denomination of CDR protein sequences in Kabat
      Nomenclature of NI-101.10 Vh, CDR1

<400> SEQUENCE: 17

Ser Tyr Gly Ile His
1               5

<210> SEQ ID NO 18
<211> LENGTH: 17
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(17)
<223> OTHER INFORMATION: Denomination of CDR protein sequences in Kabat
      Nomenclature of NI-101.10 Vh, CDR2

<400> SEQUENCE: 18

Val Ile Trp Phe Asp Gly Thr Lys Lys Tyr Tyr Thr Asp Ser Val Lys
1               5                   10                  15

Gly

<210> SEQ ID NO 19
<211> LENGTH: 15
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(15)
<223> OTHER INFORMATION: Denomination of CDR protein sequences in Kabat
      Nomenclature of NI-101.10 Vh, CDR3

<400> SEQUENCE: 19

Asp Arg Gly Ile Gly Ala Arg Arg Gly Pro Tyr Tyr Met Asp Val
1               5                   10                  15

```
<210> SEQ ID NO 20
<211> LENGTH: 5
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(5)
<223> OTHER INFORMATION: Denomination of CDR protein sequences in Kabat
      Nomenclature of NI-101.11 and NI-101.12F6A Vh, CDR1

<400> SEQUENCE: 20

Ser Tyr Gly Met His
1               5

<210> SEQ ID NO 21
<211> LENGTH: 17
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(17)
<223> OTHER INFORMATION: Denomination of CDR protein sequences in Kabat
      Nomenclature of NI-101.11 and NI-101.12F6A Vh, CDR2

<400> SEQUENCE: 21

Val Ile Trp Phe Asp Gly Thr Lys Lys Tyr Tyr Thr Asp Ser Val Lys
1               5                   10                  15

Gly

<210> SEQ ID NO 22
<211> LENGTH: 15
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(15)
<223> OTHER INFORMATION: Denomination of CDR protein sequences in Kabat
      Nomenclature of NI-101.11and NI-101.12F6A Vh, CDR3

<400> SEQUENCE: 22

Asp Arg Gly Ile Gly Ala Arg Arg Gly Pro Tyr Tyr Met Asp Val
1               5                   10                  15

<210> SEQ ID NO 23
<211> LENGTH: 11
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(11)
<223> OTHER INFORMATION: Denomination of CDR protein sequences in Kabat
      Nomenclature of NI-101.10, NI-101.11 and NI-101.12F6A Vkappa, CDR1

<400> SEQUENCE: 23

Arg Ala Ser Gln Ser Ile Ser Ser Tyr Leu Asn
1               5                   10

<210> SEQ ID NO 24
<211> LENGTH: 7
<212> TYPE: PRT
```

```
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(7)
<223> OTHER INFORMATION: Denomination of CDR protein sequences in Kabat
      Nomenclature of NI-101.10, NI-101.11 and NI-101.12F6A Vkappa, CDR2

<400> SEQUENCE: 24

Ala Ala Ser Ser Leu Gln Ser
1               5

<210> SEQ ID NO 25
<211> LENGTH: 9
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(9)
<223> OTHER INFORMATION: Denomination of CDR protein sequences in Kabat
      Nomenclature of NI-101.10, NI-101.11 and NI-101.12F6A Vkappa, CDR3

<400> SEQUENCE: 25

Gln Gln Ser Tyr Ser Thr Pro Leu Thr
1               5

<210> SEQ ID NO 26
<211> LENGTH: 5
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(5)
<223> OTHER INFORMATION: Denomination of CDR protein sequences in Kabat
      Nomenclature of NI-101.12 Vh, CDR1

<400> SEQUENCE: 26

Ser Gly Ser Ile Cys
1               5

<210> SEQ ID NO 27
<211> LENGTH: 19
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(19)
<223> OTHER INFORMATION: Denomination of CDR protein sequences in Kabat
      Nomenclature of NI-101.12 Vh, CDR2

<400> SEQUENCE: 27

Trp Ile Gly Tyr Phe Cys Tyr Ser Gly Ala Thr Phe Tyr Thr Pro Ser
1               5                   10                  15

Leu Arg Gly

<210> SEQ ID NO 28
<211> LENGTH: 17
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
```

```
<222> LOCATION: (1)..(17)
<223> OTHER INFORMATION: Denomination of CDR protein sequences in Kabat
      Nomenclature of NI-101.12 Vh, CDR3

<400> SEQUENCE: 28

Arg Ala Gly Glu Asn Ser Gly Gly Ile Glu Pro Tyr Tyr Gly Met Asp
1               5                   10                  15

Val

<210> SEQ ID NO 29
<211> LENGTH: 11
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(11)
<223> OTHER INFORMATION: Denomination of CDR protein sequences in Kabat
      Nomenclature of NI-101.12 Vkappa, CDR1

<400> SEQUENCE: 29

Arg Ala Ser Glu Ser Ile Asn Lys Tyr Val Asn
1               5                   10

<210> SEQ ID NO 30
<211> LENGTH: 7
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(7)
<223> OTHER INFORMATION: Denomination of CDR protein sequences in Kabat
      Nomenclature of NI-101.12 Vkappa, CDR2

<400> SEQUENCE: 30

Ala Ala Ser Ser Leu Gln Ser
1               5

<210> SEQ ID NO 31
<211> LENGTH: 9
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(9)
<223> OTHER INFORMATION: Denomination of CDR protein sequences in Kabat
      Nomenclature of NI-101.12 Vkappa, CDR3

<400> SEQUENCE: 31

Gln Gln Ser Tyr Ser Ala Pro Tyr Thr
1               5

<210> SEQ ID NO 32
<211> LENGTH: 7
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(7)
<223> OTHER INFORMATION: Denomination of CDR protein sequences in Kabat
      Nomenclature of NI-101.13 Vh, CDR1

<400> SEQUENCE: 32
```

```
Arg Arg Ser Tyr Tyr Trp Gly
1               5

<210> SEQ ID NO 33
<211> LENGTH: 16
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(16)
<223> OTHER INFORMATION: Denomination of CDR protein sequences in Kabat
      Nomenclature of NI-101.13 Vh, CDR2

<400> SEQUENCE: 33

Ser Ile His Tyr Ser Gly Ser Thr Tyr Tyr Asn Pro Ser Leu Lys Ser
1               5                   10                  15

<210> SEQ ID NO 34
<211> LENGTH: 11
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(11)
<223> OTHER INFORMATION: Denomination of CDR protein sequences in Kabat
      Nomenclature of NI-101.13 Vh, CDR3

<400> SEQUENCE: 34

Ser Arg Trp Gly Ser Ser Trp Val Phe Asp Tyr
1               5                   10

<210> SEQ ID NO 35
<211> LENGTH: 13
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(13)
<223> OTHER INFORMATION: Denomination of CDR protein sequences in Kabat
      Nomenclature of NI-101.13 Vlambda, CDR1

<400> SEQUENCE: 35

Ser Gly Ser Ser Ser Asn Ile Gly Ser Asn Tyr Val Tyr
1               5                   10

<210> SEQ ID NO 36
<211> LENGTH: 7
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(7)
<223> OTHER INFORMATION: Denomination of CDR protein sequences in Kabat
      Nomenclature of NI-101.13 Vlambda, CDR2

<400> SEQUENCE: 36

Arg Asn Asn Gln Arg Pro Ser
1               5

<210> SEQ ID NO 37
<211> LENGTH: 11
```

```
<212> TYPE: PRT
<213> ORGANISM: Artificial
<220> FEATURE:
<223> OTHER INFORMATION: complementarity determining region (CDR)
<220> FEATURE:
<221> NAME/KEY: MISC_FEATURE
<222> LOCATION: (1)..(11)
<223> OTHER INFORMATION: Denomination of CDR protein sequences in Kabat
      Nomenclature of NI-101.13 Vlambda, CDR3

<400> SEQUENCE: 37

Ala Ala Trp Asp Asp Ser Leu Ser Gly Tyr Val
1               5                   10

<210> SEQ ID NO 38
<211> LENGTH: 372
<212> TYPE: DNA
<213> ORGANISM: Homo sapiens
<220> FEATURE:
<221> NAME/KEY: V_region
<222> LOCATION: (1)..(372)
<223> OTHER INFORMATION: NI-101.12F6A-variable heavy (Vh) chain sequence
<220> FEATURE:
<221> NAME/KEY: CDS
<222> LOCATION: (1)..(372)

<400> SEQUENCE: 38 cag gtg cag ctg gtg gag tct ggg gga ggc gtg gtc cag cct ggg agg        48
Gln Val Gln Leu Val Glu Ser Gly Gly Gly Val Val Gln Pro Gly Arg
1               5                   10                  15 tcc ctg aga ctc tcc tgt gca gcg tct gga ttc gcc ttc agt agc tat        96
Ser Leu Arg Leu Ser Cys Ala Ala Ser Gly Phe Ala Phe Ser Ser Tyr
                20                  25                  30 ggc atg cac tgg gtc cgc cag gct cca ggc aag ggg ctg gag tgg gtg       144
Gly Met His Trp Val Arg Gln Ala Pro Gly Lys Gly Leu Glu Trp Val
            35                  40                  45 gca gtt ata tgg ttt gat gga act aaa aaa tac tat aca gac tcc gtg       192
Ala Val Ile Trp Phe Asp Gly Thr Lys Lys Tyr Tyr Thr Asp Ser Val
    50                  55                  60 aag ggc aga ttc acc atc tcc aga gac aat tcc aag aac aca ctg tat       240
Lys Gly Arg Phe Thr Ile Ser Arg Asp Asn Ser Lys Asn Thr Leu Tyr
65                  70                  75                  80 ctg caa atg aac acc ctg aga gcc gag gac acg gct gtg tat tac tgt       288
Leu Gln Met Asn Thr Leu Arg Ala Glu Asp Thr Ala Val Tyr Tyr Cys
                85                  90                  95 gcg aga gat agg ggt ata gga gct cgg cgg ggg ccg tac tac atg gac       336
Ala Arg Asp Arg Gly Ile Gly Ala Arg Arg Gly Pro Tyr Tyr Met Asp
                100                 105                 110 gtc tgg ggc aaa ggg acc acg gtc acc gtc tcc tca                       372
Val Trp Gly Lys Gly Thr Thr Val Thr Val Ser Ser
            115                 120

<210> SEQ ID NO 39
<211> LENGTH: 124
<212> TYPE: PRT
<213> ORGANISM: Homo sapiens

<400> SEQUENCE: 39

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
                20                  25                  30

Gly Met His Trp Val Arg Gln Ala Pro Gly Lys Gly Leu Glu Trp Val
            35                  40                  45
```

```
Ala Val Ile Trp Phe Asp Gly Thr Lys Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Arg Asp Arg Gly Ile Gly Ala Arg Arg Gly Pro Tyr Tyr Met Asp
                100                 105                 110

Val Trp Gly Lys Gly Thr Thr Val Thr Val Ser Ser
                115                 120
```

```
<210> SEQ ID NO 40
<211> LENGTH: 324
<212> TYPE: DNA
<213> ORGANISM: Homo sapiens
<220> FEATURE:
<221> NAME/KEY: V_region
<222> LOCATION: (1)..(324)
<223> OTHER INFORMATION: NI-101.12F6A-variable kappa (Vkappa) light
      chain sequence
<220> FEATURE:
<221> NAME/KEY: CDS
<222> LOCATION: (1)..(324)

<400> SEQUENCE: 40
```

```
gac atc cag atg acc cag tct cca tcc tcc ctg tct gca tct gta gga        48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tat        96
Asp Arg Val Thr Ile Thr Cys Arg Ala Ser Gln Ser Ile Ser Ser Tyr
                20                  25                  30 tta aat tgg tat caa cag aaa cca ggg aaa gcc cct aag ctc ctg atc       144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc       192
Tyr Ala Ala Ser Ser Leu Gln Ser Gly Val Pro Ser Arg Phe Ser Gly
    50                  55                  60 agt gga tct ggg aca gat ttc act ctc acc atc agc agt ctg caa cct       240
Ser Gly Ser Gly Thr Asp Phe Thr Leu Thr Ile Ser Ser Leu Gln Pro
65                  70                  75                  80 gaa gat ttt gca act tat tac tgt cag cag agt tac agt acc cct ctc       288
Glu Asp Phe Ala Thr Tyr Tyr Cys Gln Gln Ser Tyr Ser Thr Pro Leu
                85                  90                  95 act ttc ggc gga ggg acc aag gtg gag atc aaa cgt                       324
Thr Phe Gly Gly Gly Thr Lys Val Glu Ile Lys Arg
                100                 105
```

```
<210> SEQ ID NO 41
<211> LENGTH: 108
<212> TYPE: PRT
<213> ORGANISM: Homo sapiens

<400> SEQUENCE: 41
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys Arg
            100                 105
```

<210> SEQ ID NO 42
<211> LENGTH: 121
<212> TYPE: PRT
<213> ORGANISM: Homo sapiens
<220> FEATURE:
<221> NAME/KEY: V_region
<222> LOCATION: (1)..(121)
<223> OTHER INFORMATION: NI-101.13A-variable heavy (Vh) chain sequence

<400> SEQUENCE: 42

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Arg Arg
                 20                  25                  30

Ser Tyr Tyr Trp Gly Trp Ile Arg Gln Ser Pro Gly Lys Gly Leu Glu
             35                  40                  45

Trp Ser Gly Ser Ile His Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ser Arg Trp Gly Ser Ser Trp Val Phe Asp Tyr Trp Gly
            100                 105                 110

Gln Gly Thr Leu Val Thr Val Ser Ser
            115                 120
```

<210> SEQ ID NO 43
<211> LENGTH: 121
<212> TYPE: PRT
<213> ORGANISM: Homo sapiens
<220> FEATURE:
<221> NAME/KEY: V_region
<222> LOCATION: (1)..(121)
<223> OTHER INFORMATION: NI-101.13B-variable heavy (Vh) chain sequence

<400> SEQUENCE: 43

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Arg Arg
                 20                  25                  30

Ser Tyr Tyr Trp Gly Trp Ile Arg Gln Ser Pro Gly Lys Gly Leu Glu
             35                  40                  45

Trp Ser Gly Ser Ile His Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ser Arg Trp Gly Ser Ser Trp Val Phe Asp Tyr Trp Gly
            100                 105                 110

Gln Gly Thr Leu Val Thr Val Ser Ser
```

<210> SEQ ID NO 44
<211> LENGTH: 107
<212> TYPE: PRT
<213> ORGANISM: Homo sapiens
<220> FEATURE:
<221> NAME/KEY: V_region
<222> LOCATION: (1)..(107)
<223> OTHER INFORMATION: NI-101.13A-variable light (Vl) chain sequence

<400> SEQUENCE: 44

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Arg Thr
                85                  90                  95

Phe Gly Gln Gly Thr Lys Val Glu Ile Lys Arg
            100                 105

<210> SEQ ID NO 45
<211> LENGTH: 108
<212> TYPE: PRT
<213> ORGANISM: Homo sapiens
<220> FEATURE:
<221> NAME/KEY: V_region
<222> LOCATION: (1)..(108)
<223> OTHER INFORMATION: NI-101.13B-variable light (Vl) chain sequence

<400> SEQUENCE: 45

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Leu Glu Ile Lys Arg
            100                 105

<210> SEQ ID NO 46
<211> LENGTH: 11
<212> TYPE: PRT
<213> ORGANISM: Homo sapiens
<220> FEATURE:
<223> OTHER INFORMATION: complementarity determining region (CDR)
<220> FEATURE:
<221> NAME/KEY: MISC_FEATURE
<222> LOCATION: (1)..(11)
<223> OTHER INFORMATION: Denomination of CDR protein sequences in Kabat Nomenclature of NI-101.13A-variable light (Vl) chain sequence,
CDR1

<400> SEQUENCE: 46

Arg Ala Ser Gln Ser Ile Ser Ser Tyr Leu Asn
1               5                   10

<210> SEQ ID NO 47
<211> LENGTH: 7
<212> TYPE: PRT
<213> ORGANISM: Homo sapiens
<220> FEATURE:
<223> OTHER INFORMATION: complementarity determining region (CDR)
<220> FEATURE:
<221> NAME/KEY: MISC_FEATURE
<222> LOCATION: (1)..(7)
<223> OTHER INFORMATION: Denomination of CDR protein sequences in Kabat
      Nomenclature of NI-101.13A-variable light (Vl) chain sequence,
      CDR2

<400> SEQUENCE: 47

Ala Ala Ser Ser Leu Gln Ser
1               5

<210> SEQ ID NO 48
<211> LENGTH: 8
<212> TYPE: PRT
<213> ORGANISM: Homo sapiens
<220> FEATURE:
<223> OTHER INFORMATION: complementarity determining region (CDR)
<220> FEATURE:
<221> NAME/KEY: MISC_FEATURE
<222> LOCATION: (1)..(8)
<223> OTHER INFORMATION: Denomination of CDR protein sequences in Kabat
      Nomenclature of NI-101.13A-variable light (Vl) chain sequence,
      CDR3

<400> SEQUENCE: 48

Gln Gln Ser Tyr Ser Thr Arg Thr
1               5

<210> SEQ ID NO 49
<211> LENGTH: 11
<212> TYPE: PRT
<213> ORGANISM: Homo sapiens
<220> FEATURE:
<223> OTHER INFORMATION: complementarity determining region (CDR)
<220> FEATURE:
<221> NAME/KEY: MISC_FEATURE
<222> LOCATION: (1)..(11)
<223> OTHER INFORMATION: Denomination of CDR protein sequences in Kabat
      Nomenclature of NI-101.13B-variable light (Vl) chain sequence,
      CDR1

<400> SEQUENCE: 49

Arg Ala Ser Gln Ser Ile Ser Ser Trp Leu Ala
1               5                   10

<210> SEQ ID NO 50
<211> LENGTH: 7
<212> TYPE: PRT
<213> ORGANISM: Homo sapiens
<220> FEATURE:
<223> OTHER INFORMATION: complementarity determining region (CDR)
<220> FEATURE:
<221> NAME/KEY: MISC_FEATURE
<222> LOCATION: (1)..(7)
<223> OTHER INFORMATION: Denomination of CDR protein sequences in Kabat
      Nomenclature of NI-101.13B-variable light (Vl) chain sequence,
      CDR2

<400> SEQUENCE: 50

Lys Ala Ser Ser Leu Glu Ser
1               5

<210> SEQ ID NO 51
<211> LENGTH: 9
<212> TYPE: PRT
<213> ORGANISM: Homo sapiens
<220> FEATURE:
<223> OTHER INFORMATION: complementarity determining region (CDR)
<220> FEATURE:
<221> NAME/KEY: MISC_FEATURE
<222> LOCATION: (1)..(9)
<223> OTHER INFORMATION: Denomination of CDR protein sequences in Kabat
      Nomenclature of NI-101.13B-variable light (Vl) chain sequence,
      CDR3

<400> SEQUENCE: 51

Gln Gln Tyr Asn Ser Tyr Ser Arg Thr
1               5

<210> SEQ ID NO 52
<211> LENGTH: 363
<212> TYPE: DNA
<213> ORGANISM: Homo sapiens
<220> FEATURE:
<221> NAME/KEY: V_region
<222> LOCATION: (1)..(363)
<223> OTHER INFORMATION: NI-101.13A-variable heavy (Vh) chain sequence

<400> SEQUENCE: 52
caggtgcagc tgcaggagtc gggcccagga ctggtgaagc cttcggagac cctgtccctc      60
acctgcactg tctctggtgg ctccatcagc agaagaagtt actactgggg ctggatccgc     120
cagtccccag ggaaggggct ggagtggagt ggaagtatcc attatagcgg gagcacctac     180
tacaacccgt ccctcaagag tcgagtcacc atatctgtag acacgtccaa gaaccagttc     240
tccctgaaac tgagctctgt taccgccgca gacacggctg tctattactg tgcgagatca     300
cgttggggca gcagctgggt atttgactac tggggccagg gaaccctggt caccgtctcc     360
tcg                                                                   363

<210> SEQ ID NO 53
<211> LENGTH: 363
<212> TYPE: DNA
<213> ORGANISM: Homo sapiens
<220> FEATURE:
<221> NAME/KEY: V_region
<222> LOCATION: (1)..(363)
<223> OTHER INFORMATION: NI-101.13B-variable heavy (Vh) chain sequence

<400> SEQUENCE: 53
caggtgcagc tgcaggagtc gggcccagga ctggtgaagc cttcggagac cctgtccctc      60
acctgcactg tctctggtgg ctccatcagc agaagaagtt actactgggg ctggatccgc     120
cagtccccag ggaaggggct ggagtggagt ggaagtatcc attatagcgg gagcacctac     180
tacaacccgt ccctcaagag tcgagtcacc atatctgtag acacgtccaa gaaccagttc     240
tccctgaaac tgagctctgt taccgccgca gacacggctg tctattactg tgcgagatca     300
cgttggggca gcagctgggt atttgactac tggggccagg gaaccctggt caccgtctcc     360
tcg                                                                   363

<210> SEQ ID NO 54
<211> LENGTH: 324

```
<212> TYPE: DNA
<213> ORGANISM: Homo sapiens
<220> FEATURE:
<221> NAME/KEY: V_region
<222> LOCATION: (1)..(324)
<223> OTHER INFORMATION: NI-101.13A-variable light (Vl) chain sequence

<400> SEQUENCE: 54
gacatccagt tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccagaacgtt cggccaaggg    300
accaaggtgg agatcaaacg tacg                                           324

<210> SEQ ID NO 55
<211> LENGTH: 327
<212> TYPE: DNA
<213> ORGANISM: Homo sapiens
<220> FEATURE:
<221> NAME/KEY: V_region
<222> LOCATION: (1)..(327)
<223> OTHER INFORMATION: NI-101.13B-variable light (Vl) chain sequence

<400> SEQUENCE: 55
gacatccagt tgacccagtc tccttccacc ctgtctgcat ctgtaggaga cagagtcacc      60
atcacttgcc gggccagtca gagtattagt agctggttgg cctggtatca gcagattcca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attctcgaac gttcggccaa    300
gggaccaagc tggagatcaa acgtacg                                        327

<210> SEQ ID NO 56
<211> LENGTH: 372
<212> TYPE: DNA
<213> ORGANISM: Homo sapiens
<220> FEATURE:
<221> NAME/KEY: V_region
<222> LOCATION: (1)..(372)
<223> OTHER INFORMATION: NI-101.11-variable heavy (Vh) chain sequence

<400> SEQUENCE: 56
gaggtgcagc tggtgcagtc tgggggaggc gtggtccagc ctgggaggtc cctgagactc      60
tcctgtgcag cgtctggatt cgccttcagt agctatggca tgcactgggt ccgccaggct    120
ccaggcaagg ggctggagtg ggtggcagtt atatggtttg atggaactaa aaatactat     180 acagactccg tgaagggcag attcaccatc tccagagaca attccaagaa cacactgtat    240
ctgcaaatga acaccctgag agccgaggac acggctgtgt attactgtgc gagagatagg    300
ggtataggag ctcggcgggg gccgtactac atggacgtct ggggcaaagg gaccacggtc    360
accgtctcct ca                                                       372
```